US007785799B2

(12) United States Patent
Barrett et al.

(10) Patent No.: US 7,785,799 B2
(45) Date of Patent: Aug. 31, 2010

(54) COMPOSITIONS AND METHODS RELATED TO FLAVIVIRUS ENVELOPE PROTEIN DOMAIN III ANTIGENS

(75) Inventors: Alan Barrett, Galveston, TX (US); David Beasley, Galveston, TX (US); Michael Holbrook, Oklahoma City, OK (US)

(73) Assignee: The Board of Regents of The University of Texas System, Austin, TX (US)

(*) Notice: Subject to any disclaimer, the term of this patent is extended or adjusted under 35 U.S.C. 154(b) by 925 days.

(21) Appl. No.: 10/524,939

(22) PCT Filed: Aug. 18, 2003

(86) PCT No.: PCT/US03/25681

§ 371 (c)(1), (2), (4) Date: Mar. 4, 2008

(87) PCT Pub. No.: WO2004/016586

PCT Pub. Date: Feb. 26, 2004

(65) Prior Publication Data

US 2008/0268423 A1 Oct. 30, 2008

Related U.S. Application Data

(60) Provisional application No. 60/403,893, filed on Aug. 16, 2002, provisional application No. 60/445,581, filed on Feb. 6, 2003.

(51) Int. Cl.
*G01N 33/53* (2006.01)
*A61K 39/12* (2006.01)

(52) U.S. Cl. .................................... 435/7.1; 424/218.1

(58) Field of Classification Search ....................... None
See application file for complete search history.

(56) References Cited

U.S. PATENT DOCUMENTS 4,447,356 A 5/1984 Oliver et al. ................ 530/327
4,500,512 A 2/1985 Barme ...................... 424/218.1
4,810,492 A 3/1989 Fujita et al.
5,218,088 A 6/1993 Gorenstein et al. ........ 536/25.34
5,220,007 A 6/1993 Pederson et al. .......... 536/523.1
5,270,163 A 12/1993 Gold et al. ...................... 435/6
5,284,760 A 2/1994 Feinstone et al. ......... 435/491.1
5,354,670 A 10/1994 Nickoloff et al. ...... 435/491.53
5,366,878 A 11/1994 Pederson et al. ......... 435/491.3
5,389,514 A 2/1995 Taylor ......................... 435/46
5,397,698 A 3/1995 Goodman et al. .............. 435/6
5,475,096 A 12/1995 Gold et al. ................. 536/23.1
5,514,774 A 5/1996 Olivera et al. ............... 530/324
5,576,302 A 11/1996 Cook et al. ................... 514/44
5,582,981 A 12/1996 Toole et al. ..................... 435/6
5,587,361 A 12/1996 Cook et al. ................... 514/44
5,589,340 A 12/1996 Olivera et al. .................. 435/6
5,591,821 A 1/1997 Olivera et al. ............... 530/324
5,595,972 A 1/1997 Olivera et al. ................. 514/13
5,599,797 A 2/1997 Cook et al. .................... 514/44
5,602,000 A 2/1997 Hyman ...................... 435/91.1
5,607,923 A 3/1997 Cook et al. ................... 514/44
5,620,963 A 4/1997 Cook et al. ................... 514/44
5,633,347 A 5/1997 Olivera et al. ............... 530/324
5,635,377 A 6/1997 Pederson et al. ........... 435/91.3
5,635,488 A 6/1997 Cook et al. ................... 435/44
5,639,603 A 6/1997 Dower et al. ..................... 435/6
5,639,873 A 6/1997 Barascut et al. ............ 536/25.3
5,660,985 A 8/1997 Pieken et al. .................... 435/6
5,661,134 A 8/1997 Cook et al. ................... 514/44
5,663,153 A 9/1997 Hutcherson et al. ........... 514/44
5,668,265 A 9/1997 Nadeau et al. ............. 536/23.1
5,670,622 A 9/1997 Shon et al. .................. 530/324
5,670,637 A 9/1997 Gold et al. ................. 536/22.1
5,672,682 A 9/1997 Terlau et al. ................ 530/324
5,696,249 A 12/1997 Gold et al. ................. 536/23.1
5,705,337 A 1/1998 Gold et al. ..................... 435/6
5,719,264 A 2/1998 Shon et al. .................. 530/324
5,734,041 A 3/1998 Just et al. ................. 536/25.31
5,736,148 A 4/1998 Sumiyoshi et al. ....... 424/218.1
5,739,276 A 4/1998 Shon et al. .................. 530/324
5,744,140 A 4/1998 Paoletti et al.
5,744,141 A 4/1998 Paoletti et al.

(Continued)

FOREIGN PATENT DOCUMENTS

WO WO 01/60847 8/2001

(Continued)

OTHER PUBLICATIONS

Dauphin et al. Vaccine, 2007, 25:5563-5576.*
Chu et al. Journal of Immunology, 2007, 178:2699-2705.*
Amarzguioui et al., "Tolerance for mutations and chemical modification in a siRNA," *Nuc. Acids Res.*, 31:589-595, 2003.
Anderson et al., "A phylogenetic approach to following West Nile virus in Connecticut," *PNAS*, 98:12885-12889, 2001.
Arroyo et al., "ChimeriVax-West Nile Virus Live-Attenuated Vaccine: Preclinical Evaluation of Safety, Immunogenicity, and Efficacy," *J. Virology*, 78:12497-12507, 2004.
Bane et al., "DNA affinity capture and protein profiling by SELDI-TOF mass spectrometry: effect of DNA methylation," *Nucleic Acids Research*, 30:e69, 2002.

(Continued)

*Primary Examiner*—Stacy B Chen
(74) *Attorney, Agent, or Firm*—Fulbright & Jaworski L.L.P.

(57) ABSTRACT

The present invention concerns methods and compositions involving flavivirus envelope protein domain III antigens for the detection of virus and detection of antibodies against the virus. Such methods and compositions may be used to detect TBE serocomplex viruses or West Nile virus infection in a subject, patient, animal or biological fluid. The present invention also concerns kits for implementing such methods. In some embodiments, kits contain a recombinant TBE serocomplex virus or West Nile virus envelope protein domain III antigen.

13 Claims, 16 Drawing Sheets

U.S. PATENT DOCUMENTS

| | | | | |
|---|---|---|---|---|
| 5,756,291 | A | 5/1998 | Griffin et al. | 435/6 |
| 5,763,595 | A | 6/1998 | Gold et al. | 536/22.1 |
| 5,780,221 | A | 7/1998 | Schumacher et al. | 435/5 |
| 5,789,166 | A | 8/1998 | Bauer et al. | 435/46 |
| 5,795,721 | A | 8/1998 | Rabin et al. | 435/6 |
| 5,798,208 | A | 8/1998 | Crea | 435/46 |
| 5,801,154 | A | 9/1998 | Baracchini et al. | 514/44 |
| 5,804,445 | A | 9/1998 | Brasier | 435/375 |
| 5,830,650 | A | 11/1998 | Crea | 435/6 |
| 5,844,106 | A | 12/1998 | Seela et al. | 536/22.1 |
| 5,853,984 | A | 12/1998 | Davis et al. | 435/6 |
| 5,874,219 | A | 2/1999 | Rava | 435/6 |
| 5,885,780 | A | 3/1999 | Olivera et al. | 435/7.1 |
| 5,969,096 | A | 10/1999 | Shon et al. | 530/325 |
| 5,990,295 | A | 11/1999 | Shon et al. | 536/23.5 |
| 6,150,088 | A | 11/2000 | Chan et al. | 435/5 |
| 6,171,792 | B1 | 1/2001 | Brent et al. | 435/6 |
| 6,171,854 | B1 | 1/2001 | Galler et al. | 435/320.1 |
| 6,180,348 | B1 | 1/2001 | Li | 435/6 |
| 6,184,024 | B1 | 2/2001 | Lai et al. | 435/235.1 |
| 6,242,246 | B1 | 6/2001 | Gold et al. | 435/287.1 |
| 6,254,873 | B1 | 7/2001 | Putnak et al. | 424/218.1 |
| 6,258,788 | B1 * | 7/2001 | Schmaljohn | 514/44 |
| 6,265,541 | B1 | 7/2001 | Olivera et al. | 530/326 |
| 6,337,073 | B1 | 1/2002 | Niedrig et al. | 424/218.1 |
| 6,346,611 | B1 | 2/2002 | Pagratis et al. | 536/23.1 |
| 6,369,208 | B1 | 4/2002 | Cole et al. | 536/23.1 |
| 6,372,221 | B2 | 4/2002 | Mannhalter et al. | 424/196.11 |
| 6,423,493 | B1 | 7/2002 | Gorenstein et al. | 435/6 |
| 6,458,543 | B1 | 10/2002 | Gold et al. | 435/6 |
| 6,503,715 | B1 | 1/2003 | Gold et al. | 435/6 |
| 6,506,554 | B1 | 1/2003 | Chan et al. | 435/5 |
| 6,514,948 | B1 | 2/2003 | Raz et al. | 514/44 |
| 6,544,776 | B1 | 4/2003 | Gold et al. | 435/287.2 |
| 6,551,795 | B1 | 4/2003 | Rubenfield et al. | 435/69.1 |
| 6,576,757 | B1 | 6/2003 | Punnonen et al. | 536/23.72 |
| 6,610,504 | B1 | 8/2003 | Yuan | 435/15 |
| 6,713,616 | B2 | 3/2004 | Pagratis et al. | 536/23.1 |
| 6,716,629 | B2 | 4/2004 | Hess et al. | 435/420 |
| 6,725,526 | B2 | 4/2004 | Lille | 29/603.1 |
| 6,734,022 | B2 | 5/2004 | Hutchens et al. | 436/173 |
| 6,844,165 | B2 | 1/2005 | Hutchens et al. | 435/7.92 |
| 6,867,289 | B1 | 3/2005 | Gorenstein et al. | 536/23.1 |
| 7,227,011 | B2 * | 6/2007 | Chang | 536/23.72 |
| 2001/0034330 | A1 | 10/2001 | Kensil | 514/44 |
| 2003/0022849 | A1 * | 1/2003 | Chang | 514/44 |
| 2003/0148261 | A1 | 8/2003 | Fikrig et al. | 435/5 |
| 2003/0162190 | A1 | 8/2003 | Gorenstein et al. | 435/6 |
| 2003/0162216 | A1 | 8/2003 | Gold et al. | 435/6 |
| 2003/0180329 | A1 | 9/2003 | Monath et al. | 424/218.1 |
| 2003/0186906 | A1 | 10/2003 | Schlingensiepen et al. | 514/44 |
| 2003/0228327 | A1 | 12/2003 | Lasher et al. | 424/188.1 |
| 2004/0037848 | A1 | 2/2004 | Audonnet et al. | 424/199.1 |
| 2004/0052818 | A1 | 3/2004 | Heinz et al. | 424/202.1 |
| 2005/0002968 | A1 | 1/2005 | Monath et al. | 424/218.1 |
| 2005/0031641 | A1 | 2/2005 | Loosmore et al. | 424/199.1 |
| 2005/0053624 | A1 | 3/2005 | Arroyo et al. | 424/218.1 |
| 2005/0163804 | A1 | 7/2005 | Chang | 424/218.1 |
| 2005/0164170 | A1 | 7/2005 | Despres et al. | 435/5 |

FOREIGN PATENT DOCUMENTS

| | | | |
|---|---|---|---|
| WO | WO 02/072036 | | 9/2002 |
| WO | WO 02/081621 | | 10/2002 |
| WO | WO 02/083903 | A2 * | 10/2002 |
| WO | WO 03/048184 | | 6/2003 |
| WO | WO 03/061555 | | 7/2003 |
| WO | WO 03/103571 | | 12/2003 |
| WO | WO 2004/016586 | | 2/2004 |
| WO | WO 2004/045529 | | 6/2004 |
| WO | WO 2005/042014 | | 5/2005 |

OTHER PUBLICATIONS

Bartelma et al., "Expression, Purification, and Characterization of the RNA 5'-Triphosphatase Activity of Dengue Virus Type 2 Nonstructural Protein 3," *Virology*, 299: 122-132, 2002.

Beasley and Barrett, "Identification of neutralizing epitopes within structural domain III of the West Nile virus envelope protein." *J. Virol*, 76(24):13097-13100, 2002.

Beasley et al., "Limited evolution of West Nile virus has occurred during its southwesterly spread in the United States," *Virology*, 309: 190-195, 2003.

Beasley et al., "Mouse neuroinvasive phenotype of West Nile virus strains varies depending upon virus genotype." *J. Virol*, 296(1):17-23, 2002.

Berthet et al., "Extensive nucelotide changes and deletions within the envelope glycoprotein gene of Euro-African West Nile viruses," *J. General Virology*, 78: 2293-2297, 1997.

Bhardwaj et al., "Biophysical characterization and vector-specific antagonist activity of domain III of the tick-borne flavivirus envelope protein." *J. Virol*, 75:4002-4007, 2001.

Blitvich et al., "Serologic evidence of West Nile virus infection in horses, Coahuila State, Mexico," *Emerg. Infect. Dis.*, 9: 853-856, 2003.

Braasch et al., "Antisense inhibition of gene expression in cells by oligonucleotides incorporating locked nucleic acids: effect of mRNA target sequence and chimera design," *Nucleic Acids Res.*, 30:5150-7, 2002.

Brinton, "The molecular biology of West Nile Virus: a new invader of the western hemisphere," *Annu. Rev. Microbiol.*, 56:371-402, 2002.

Brown et al., "Tolerance of single, but not multiple, amino acid replacements in antibody VH CDR 2: a means of minimizing B cell wastage from somatic hypermutation?" *J. Immunol*, 156(9):3285-3291, 1996.

Burke and Monath, "Flaviviruses," *In* D. M. Knipe, P. M. Howley, D. E. Griffin, R. A. Lamb, M. A. Martin, B. Roizman, and S. E. Straus (ed.), Fields virology, 4th ed., vol. 1:. Lippincott Williams & Wilkins, Philadelphia, Pa., 1043-1125, 2001.

Burton and Barbas, "Human antibodies from combinatorial libraries." *Adv. Immunol*, 57:191-280, 1994.

Butrapet et al., "Attenuation Markers of a Candidate Dengue Type 2 Vaccine Virus, Strain 16681 (PDK-53), Are Defined by Mutations in the 5' Noncoding Region and Nonstructural Proteins 1 and 3," *J. Virology*, 74:3011-3019, 2000.

Caplen et al., "Specific inhibition of gene expression by small double-stranded RNAs in invertebrate systems," *PNAS*, 98:9742-9747, 2001.

CDC, "Serological and molecular amplification assays for West Nile & other arboviruses," 2001.

Chambers et al., "West Nile virus envelope proteins: nucleotide sequence analysis of strains differing in mouse neuroinvasiveness," *J. General Virology*, 79: 2375-2380, 1998.

Chappell et al., "Site-directed Mutagenesis and Kinetic Studies of the West Nile Virus NS3 Protease Identify Key Enzyme-Substrate Interactions," *J. Biol. Chem.*, 280(4): 2896-2903, 2005.

Charrel et al., "Evolutionary relationship between Old World West Nile virus strains Evidence for viral gene flow between Africa, the Middle East, and Europe," *Virology*, 315: 381-388, 2003.

Chi, "Genomewide view of gene silencing by small interfering RNAs," *PNAS*, 100:6343-6, 2003.

Crill and Roehrig, "Monoclonal antibodies that bind to domain III of dengue virus E glycoprotein are the most efficient blockers of virus adsorption to Vero cells." *J. Virol*, 75(16):7769-7773, 2001.

Davis et al., "Genetic variation among temporally and geographically distinct West Nile virus isolates collected in the Unites States, 2001 and 2002," *Emerg. Infect. Dis.*, 10(1): 160, 2004.

Dobler et al., "Diagnosis of tick-borne encephalitis: evaluation of sera with borderline titers with the TBE-ELISA." *Infection*, 24:405-406, 1996.

Dunster et al., "Attenuation of virulence of flaviviurses following passage in HeLa cells," *J. Gen. Vir.*, 71: 601-607, 1990.

Dupuis et al., "Serological evidence of West Nile virus transmission, Jamaica, West Indies," *Emerg. Infect. Dis.*, 9: 860-863, 2003.
Ebel et al., "Genetic and Phenotypic Variation of West Nile Virus in New York, 2000-2003," *Am. J. Trop. Med. Hyg.*, 71(4): 493-500, 2004.
Egloff et al., "An RNA cap (nucleoside-2'-*O*-)-Methyltransferase in the flavivirus RNA polymerase NS5: crystal structure and functional characterization," *The EMBO Journal,* 21(11): 2757-2768, 2002.
Elbashir et al., "Functional anatomy of siRNAs for medicating efficient RNAi in drosophillia melanogaster embryo lysate," *EMBO Journal,* 20:6877-6888, 2001.
Elbashir et al., "RNA interference is mediated by 21-and 22-nulceotide RNAs," *Genes and Development,* 15:188-200, 2001.
Estrada-Franco et al., "West Nile virus in Mexico: evidence of widespread circulation since Jul. 2002," *Emerg. Infect. Dis.*, 9: 1604-1607, 2003.
Fonseca et al., "Flavivirus type-specific antigens produced from fusions of a portion of the E protein gene with the *Escherichia coli* trpE gene." *Am. J. Trop. Med. Hyg.*, 44(5):500-8, 1991.
Gould et al., "Evolution, epidemiology, and dispersal of flaviviruses revealed by molecular phylogenies." *Adv Virus Res*, 57:71-103, 2001.
Gritsun et al., "Nucleotide and deduced amino acid sequence of the envelope gene of the Vasilchenko strain of TBE virus; comparison with other flaviviruses," *Virus Res*, 27:201-209, 2003.
Hahn et al., "Comparison of the virulent Asibi strain of yellow fever virus with the 17D vaccine strain derived from it." *Proc. Natl. Acad. Sci.*, USA, 84:2019-2023, 1987.
Hanley et al., "Paired charge-to-alanine mutagenesis of dengue virus type 4 NS5 generates mutants with temperature-sensitive, host range, and mouse attenuation phenotypes," *J. Virol.*, 76: 525-531, 2002.
Heinz et al., In: *Virus Taxonomy,* Regenmortel et al. eds., $7^{th}$ International Committee for the Taxonomy of Viruese, p. 859-878, Academic Press, San Diego, 2000.
Hilton et al., "Saturation mutagenesis of the WSXWS motif of the erythropoietin receptor." *J. Biol. Chem.*, 271(9):4699-4708, 1996.
Huang et al., "Chimeric Dengue 2 PDK-53/West Nile NY99 Viruses Retain the Phenotypic Attenuation Markers of the Candidate PDK-53 Vaccine Virus and Protect Mice against Lethal Challenge with West Nile Virus," *J. Virology,* 79: 7300-7310, 2005.
Jackson et al., "Isolation of Arabidopsis mutants altered in the light-regulation of chalcone synthase gene expression using a transgenic screening approach." *Plant J.*, 8:369-380, 1995.
Jayasena, "Aptamers: an emerging class of molecules that rival antibodies in diagnostics," *Clinical Chemistry,* 45:1628-1650, 1999.
Jia et al., "Genetic analysis of West Nile New York 1999 encephalitis virus." *Lancet,* 354:1971-1972, 1999.
Jones et al., "Flavivirus Capsid Is a Dimeric Alpha-Helical Protein," *J. Virology,* 77: 7143-7149, 2003.
Kofler et al., "Mimicking live flavivirus immunization with a noninfectious RNA vaccine," *PNAS,* 101(7): 1951-1956, 2004.
Kunsch et al., "Selection of optimal kappa B/Rel DNA-binding motifs: interaction of both subunits of NF-kappa B with DNA is required for transcriptional activation," *Molecular and Cellular Biology,* 12:4412-4421, 1992.
Lanciotti and Kerst, "Nucleic Acid Sequence-Based Amplification Assays for Rapid Detection of West Nile and St. Louis Encephalitis Viruses," *J. Clinical Microbiology,* 39(12): 4506-4513, 2001.
Lanciotti et al., "Complete Genome Sequences and Phylogenetic Analysis of West Nile Virus Strains Isolated from the United States, Europe, and the Middle East," *Virology,* 298: 96-105, 2002.
Lanctiotti et al., "Origin of the West Nile virus responsible for an outbreak of encephalitis in the northeastern United States." *Science,* 286(5448):2333-2337,1999.
Lee et al., "Common E Protein Determinants for Attenuation of Glycosaminoglycan-Binding Variants of Japanese Encephalitis and West Nile Viruses," *J. Virology,* 78(15): 8271-8280, 2004.
Lescar et al., "The fusion glycoprotein shell of Semliki Forest virus: an icosahedral assembly primed for fusogenic activation at endosomal pH," *Cell,* 105:137-148, 2001.
Lustig et al., "A Live Attenuated West Nile Virus Strain as a Potential Veterinary Vaccine," *Viral Immunology,* 13(4): 401-410, 2000.
Ma et al., "Solution structure of dengue virus capsid protein reveals another fold," *PNAS*, 101(10): 3414-3419, 2004.
Mandl et al., "Attenuation of tick-borne encephalitis virus by structure-based site-specific mutagenesis of a putative flavivirus receptor binding site." *J. Virol*, 74(20):9601-9609, 2000.
Marshall et al., "Inhibition of human immunodeficiency virus activity by phosphorodithioate oligodeoxycytide," *PNAS*, 89:6265-6269, 1992.
Martin et al., "Molecular basis of mitomycin C resistance in streptomyces: structure and function of the MRD protein." *Structure*, 10:933-942, 2002.
Mashimo et al., "A nonsense mutation in the gene encoding 2'-5'-oligoadenylate synthetase/L1 isoform is associated with West Nile virus susceptibility in laboratory mice," *PNAS,* 99(17): 11311-11316, 2002.
McMinn, "The molecular basis of virulence of the encephalitogenic flaviviruses," *J. General Virology,* 78: 2711-2722, 1997.
Miller et al., "Allele-specific siliencing of dominant disease genes," *PNAS*, 100:7195-7200, 2003.
Monath et al., "West Nile Virus Vaccine," *Current Drug Targets,* 1: 37-50, 2001.
*Morbidity and Mortality Weekly Report,* 51(36):805-824, 2002.
*Morbidity and Mortality Weekly Report,* 51(38):862-864, , 2002.
Murgue et al., "The ecology and epidemiology of West Nile virus in Africa, Europe and Asia." *Curr Top Microbiol Immunol,* 267:195-221, 2002.
Murthy et al., "Crystal Structure of Dengue Virus NS3 Protease in Complex with a Bowman-Birk Inhibitor: Implications for Flaviviral Polyprotein Processing and Drug Design," *J. Mol. Biol.*, 301: 759-767, 2000.
Murthy et al., "Dengue Virus NS3 Serine Protease," *J. Biol. Chem.*, 274(9): 5573-5580, 1999.
Mutebi et al., "Phylogenetic and evolutionary relationships among yellow fever virus isolates in Africa." *J. Virol,* 75:6999-7008, 2001.
Nakamaye et al., "Direct sequencing of polymerase chain reaction amplified DNA fragments through the incorporation of deoxynucleoside alpha-thiotriphosphates," *Nucleic Acids Research,* 16: 9947-59, 1988.
Niedrig et al., "Comparison of six different commercial IgG-ELISA kits for the detection of TBEV-antibodies." *J Clinical Virology,* 20:179-182, 2001.
Papin et al., "SYBR green-based real-time quantitative PCR assay for detection of West Nile Virus circumvents false-negative results due to strain variability," *J. Clin. Mircobiol.*, 42:1511-1518, 2004.
Pletnev et al., "West Nile virus/dengue type 4 virus chimeras that are reduced in neurovirulence and peripheral virulence without loss of immunogenicity or protective efficacy," *PNAS*, 99(5): 3036-3041, 2002.
Quirin et al., "West Nile virus, Guadeloupe," *Emerg. Infect. Dis.*, 10: 706-708, 2004.
Rey et al., "Changes in the dengue virus major envelope protein on passaging and their localization on the three-dimensional structure of the protein." *Nature,* 375:291-298, 1995.
Rey et al., "The envelope glycoprotein from tick-borne encephalitis virus at 2 A resolution," *Nature,* 375:291-298, 1995.
Ryan et al., "Virus-encoded proteinases of the *Flaviviridae," J. General Virology,* 79: 947-959, 1998.
Sanchez and Ruiz, "A single nucleotide change in the E protein gene of dengue virus 2 Mexican strain affects neurovirulence in mice." *J Gen Virol*, 77(Pt 10):2541-2545, 1996.
Sazani et al., "Nuclear antisense effects of neutral anionic and cationic oligonucleotide analogs," *Nucleic Acids Research,* 29:3965-3974, 2001.
Scherret et al., "Biological significance of glycosylation of the envelope protein of Kunjin virus." *Ann NY Acad Sci,* 951:361-363, 2001.
Semizarov et al., "Specificity of short interfering RNA determined through gene expression signatures," *PNAS*, 100:6347-52, 2003.
Short et al., "Contribution of antibody heavy chain CDR1 to digoxin binding analyzed by random mutagenesis of phage-displayed Fab 26-10," *J. Biol. Chem.*, 270:28541-50 1995.
Shrestha et al., "Infection and Injury of Neurons by West Nile Encephalitis Virus," *J. Virology,* 77(24): 13203-13213, 2003.
Smith et al., "Sensitivity and specificity of photoaptamer probes," *Molecular & Cellular Proteomics*, 2:11-18, 2003.

Song et al., "Sustained small interfering RNA-mediated human immunodeficiency virus type 1 inhibition in primary macrophages," *J. Virol.,* 77:7174-81, 2003.

Tesh et al., "Experimental yellow fever virus infection in the Golden Hamster (*Mesocricetus auratus*). I. Virologic, biochemical, and immunologic studies." *J. Infect Dis.,* 183:1431-1436, 2001.

Ueda et al., "Phosphorothioate-containing RNAs show mRNA activity in the prokaryotic translation systems in vitro," *Nucleic Acids Research,* 19:547-552, 1991.

van der Meulen et al., "West Nile virus in the vertebrate world," *Arch. Virol.,* 150: 637-657, 2005.

Volk et al., "Solution Structure and Antibody Binding Studies of the Envelope Protein Domain III from the New York strain of West Nile Virus," *JBC Papers in Press,* published on Jun. 9, 2004 as Manuscript M402385200.

Warren et al., "A rapid screen of active site mutants in glycinamide ribonucleotide transformylase." *Biochemistry,* 35(27):8855-8862, 1996.

Whitehead et al., "A live, attenuated dengue virus type 1 vaccine candidate with a 30-nucleotide deletion in the 3' untranslated region is highly attenuated and immunogenic in monkeys," *Journal of Virology*, 77:1653-1657, 2003.

Wong et al., "Directed mutagenesis of the Rhodobacter capsulatus puhA gene and orf 214: pleiotropic effects on photosynthetic reaction center and light-harvesting 1 complexes." *J. Bacteriol,* 178(8):2334-2342, 1996.

Xie et al., "Mutation in NS5 protein attenuates mouse neurovirulence of yellow fever 17D vaccine virus," *J. General Virology,* 79: 1895-1899, 1998.

Yamshchikov et al., "An attenuated West Nile prototype virus is highly immunogenic and protects against the deadly NY99 strain: a candidate for live WN vaccine development," *Virology,* 330: 304-312, 2004.

Yamshchikov et al., "An infectious clone of the West Nile flavivirus," *Virology*, 281: 294-304, 2001.

Yang et al., "Construction and selection of bead-bound combinatorial oligonucleoside phosphorothioate and phosphorodithioate aptamer libraries designed for rapid PCR-based sequencing," *Nucleic Acid Research*, 30:132-140, 2002.

Yang et al., "Immunofluorescence assay and flow-cytometry selection of bead-bound aptamers," *Nucleic Acids Research,* 31:e54, 2003.

Yelton et al., "Affinity maturation of the BR96 anti-carcinoma antibody by codon-based mutagenesis." *J Immunol,* 155(4):1994-2004, 1995.

Yokota et al., "Inhibition of intracellular hepatitis C virus by synthetic and vector-derived small interfereing RNAs," *EMBO Rep.,* 4:602-608, 2003.

Yoshii et al., "Enzyme-linked immunosorbent assay using recombinant antigens expressed in mammalian cells for serodiagnosis of tick-borne encephalitis." *J Virol Methods,* 108:171-179, 2003.

Yu et al., "Solution Structure and Structural Dynamics of Envelope Protein Domain III of Mosquito- and Tick-Borne Flaviviruses," *Biochemistry,* 43: 9168-9176, 2004.

Zanotto et al., "An arbovirus cline across the northern hemisphere." *Virology,* 210:152-159, 1995.

Zeng et al., "ATP-binding site of human brain hexokinase as studied by molecular modeling and site-directed mutagenesis." *Biochemistry,* 35(40):13157-13164, 1996.

* cited by examiner

| | | | |
|---|---|---|---|
| | | `**  *  *    *          * *         *   **  *` | 351 |
| Mosquito | DEN1 | KGVSYVMCT-GSFKLEKEVAETQHGTVLVQVKYEGTDAPCKIPFSSQDEKGVT | |
| | DEN3 | KGMSYAMCL-NTFVLKKEVSETQHGTILIKVEYKGEDAPCKIPFSTEDGQGKA | |
| | DEN2 | KGMSYSMCT-GKFKVVEEIAETQHGTIVIRVQYEGDGSPCKIPLEIMDLDNRH | |
| | DEN4 | KGMSYTMCS-GKFSIDKEMAETQHGTTVVKVKYEGAGAPCKVPIEIRDVNKEK | |
| | JE | KGTTYGMCT-EKFSFAKNPADTGHGTVVIELSYSGSDGPCKIPIVSVASLNDM | |
| | MV | KGTTYGMCT-EKFTFSKNPADTGHGTVVLELQYTGSDGPCKIPISSVASLNDM | |
| | KUN | KGTTYGVCS-KAFRFLGTPADTGHGTVVLELQYTGTDGPCKIPISSVASLNDL | |
| | WN | KGTTYGVCS-KAFKFLGTPADTGHGTVVLELQYTGTDGPCKVPISSVASLNDL | |
| | SLE | KGTTYGMCD-SAFTFSKNPTDTGHGTVIVELQYTGSNGPCRVPISVTANLMDL | |
| | YF | KGTSYKMCT-DKMSFVKNPTDTGHGTAVMQVKVPKG-APCRIPVMVADDLTAS | |
| Tick | TBE | KGLTYTMCDKTKFTWKRAPTDSGHDTVVMEVTFSGT-KPCRIPVRAVAHGSPD | |
| | KFD | KGMTYTVCEGSKFAWKRPPTDSGHDTVVMEVTYTGS-KPCRIPVRAVAHGEPN | |
| | KUM | KGLTYTMCDKTKFTWKRAPTDSGHDTVVMEVTFSGT-KPCRIPVRAVAHGSPD | |
| | LI | KGLTYTMCDKSKFAWKRTPTDSGHDTVVMEVTFSGS-KPCRIPVRAVAHGSPD | |
| | LGT | KGLTYTVCDKTKFTWKRAPTDSGHDTVVMEVGFSGT-RPCRIPVRAVAHGVPE | |
| | OHF | KGLTYTMCDKAKFTWKRAPTDSGHDTVVMEVAFSGT-KPCRIPVRAVAHGSPD | |
| | POW | KGTTYSMCDKAKFKWKRVPVDSGHDTVVMEVSYTGSDKPCRIPVRAVAHGVPA | |

| | | | |
|---|---|---|---|
| | | `* **             *    ** *    *    *       *` | 395 |
| Mosquito | DEN1 | Q-NGRLITANPIVIDKEK--PVNIEAE-PPFGESYIVVGAGEKALKLSWFKK | SEQ ID NO:4 |
| | DEN3 | H-NGRLITANPVVTKKEE--PVNIEAE-PPFGESNIVIGIGDKALKINWYRK | SEQ ID NO:5 |
| | DEN2 | V-LGRLITVNPIVTEKDS--PVNVEAE-PPLGDSYIIIGVEPGQLKLNWFKK | SEQ ID NO:6 |
| | DEN4 | V-VGRIISSTPLAENTNS--VTNIELE-RPL-DSYIVIGVGNSALTLHWFRK | SEQ ID NO:7 |
| | JE | TPVGRLVTVNPFVATSSANSKVLVEME-PPFGDSYIVVGRGDKQINHHWHKA | SEQ ID NO:8 |
| | MV | TPVGRMVTANPYVASSTANAKVLVEIE-PPFGDSYIVVGRGDKQINHHWHKE | SEQ ID NO:9 |
| | KUN | TPVGRLVTVNPFVSVSTANAKVLIELE-PPFGDSYIVVGRGEQQINHHWHKS | SEQ ID NO:10 |
| | WN | TPVGRLVTVNPFVSVATANAKVLIELE-PPFGDSYIVVGRGEQQINHHWHKS | SEQ ID NO:11 |
| | SLE | TPVGRLVTVNPFISTGGANNKVMIEVE-PPFGDSYIVVGRGTTQINYHWHKE | SEQ ID NO:12 |
| | YF | VNKGILVTVNPIASTNED--EVLIEVN-PPFGDSYIIVGTGDSRLTYQWHKE | SEQ ID NO:13 |
| Tick | TBE | VNVAMLITPNPTIENNGG---GFIEMQLPP-GDNIIYVG----ELSYQWFQK | SEQ ID NO:14 |
| | KFD | VNVASLITPNPSMENTGG---GFVELQLPP-GDNIIYVG----ELSHQWFQK | SEQ ID NO:15 |
| | KUM | VNVAMLITPNPTIENNGG---GFIEMQLPP-GDNIIYVG----ELSHQWFQK | SEQ ID NO:16 |
| | LI | VNVAMLITPNPTIENDGG---GFIEMQLPP-GDNIIYVG----ELSHQWFQT | SEQ ID NO:17 |
| | LGT | VNVAMLITPNPTMENNGG---GFIEMQLPP-GDNIIYVG----DLNYQWFQK | SEQ ID NO:18 |
| | OHF | VDVAMLITPNPTIENNGG---GFIEMQLPP-GDNIIYVG----ELKHQWFQK | SEQ ID NO:19 |
| | POW | VNVAMLITPNPTIETNGG---GFIEMQLPP-GDNIIYVG----DLSQQWFQK | SEQ ID NO:20 |

FIG. 1

| | 80% PRNT | | 50% PRNT | |
|---|---|---|---|---|
| Virus | anti LGT | anti-WN | anti LGT | anti-WN |
| DEN2 | <20 | <20 | <20 | <20 |
| DEN4 | nt | nt | nt | nt |
| JE | <20 | <20 | <20 | <20 |
| WN | <20 | **320** | <20 | **>320** |
| YF | <20 | <20 | <20 | <20 |
| LGT | **40** | <20 | **80** | <20 |
| POW | <20 | <20 | **20** | <20 |

Data given as reciprocal of the Ab dilution to give a 80% or 50% reduction in plaque number

FIG. 5

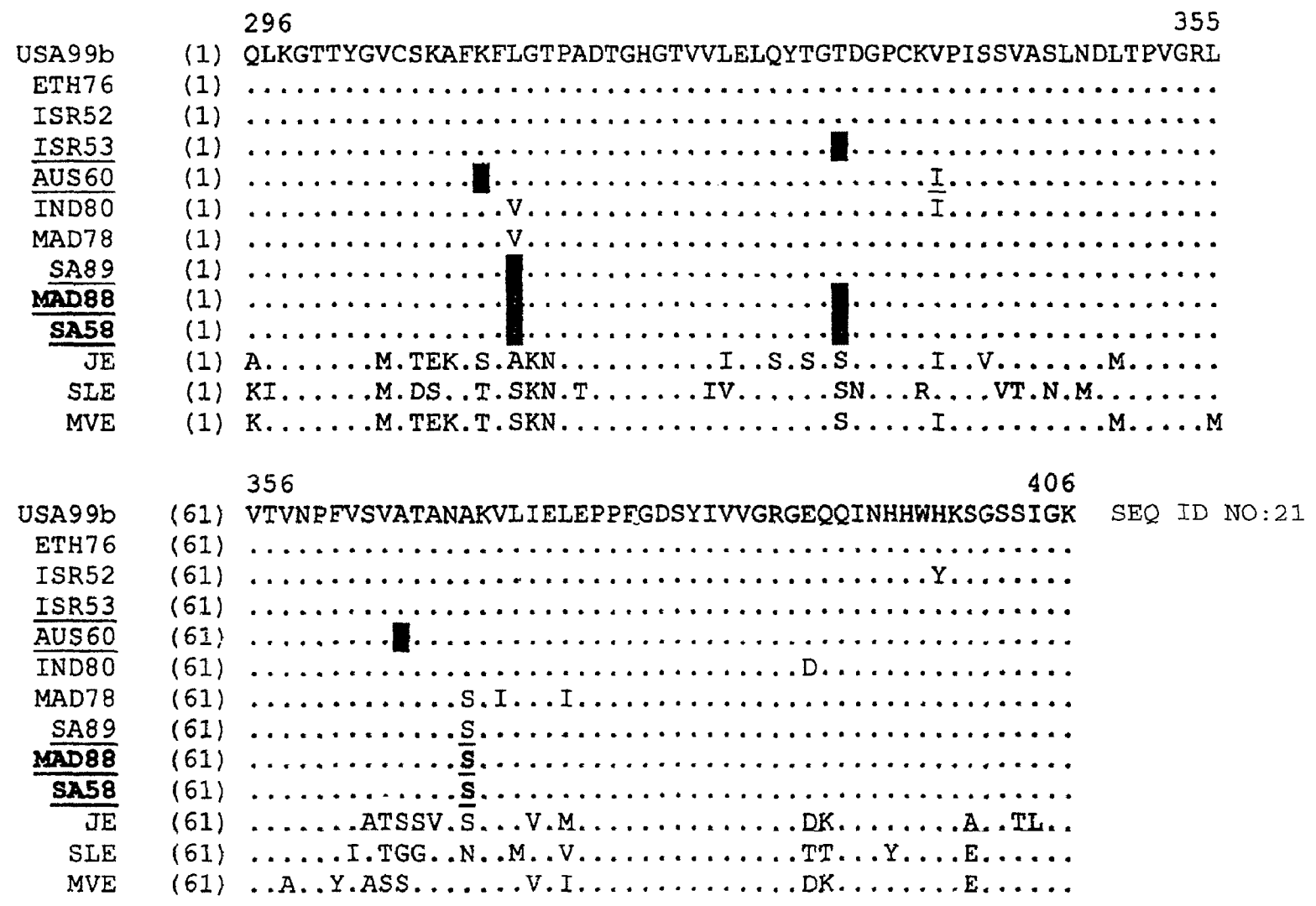

```
                296                                                         355
USA99b    (1)   QLKGTTYGVCSKAFKFLGTPADTGHGTVVLELQYTGTDGPCKVPISSVASLNDLTPVGRL
ETH76     (1)   ............................................................
ISR52     (1)   ............................................................
ISR53     (1)   ....................................■.......................
AUS60     (1)   ..............■...........................I.................
IND80     (1)   ................V.........................I.................
MAD78     (1)   ................V...........................................
SA89      (1)   ................■...........................................
MAD88     (1)   ................■...................■.......................
SA58      (1)   ................■...................■.......................
JE        (1)   A.......M.TEK.S.AKN..........I..S.S.S.....I..V.......M......
SLE       (1)   KI......M.DS..T.SKN.T.......IV......SN...R...VT.N.M.........
MVE       (1)   K.......M.TEK.T.SKN.................S.....I..........M.....M

                356                                                406
USA99b    (61)  VTVNPFVSVATANAKVLIELEPPFGDSYIVVGRGEQQINHHWHKSGSSIGK   SEQ ID NO:21
ETH76     (61)  ...................................................
ISR52     (61)  ..........................................Y........
ISR53     (61)  ...................................................
AUS60     (61)  .........■.........................................
IND80     (61)  ..................................D................
MAD78     (61)  .............S.I...I...............................
SA89      (61)  .............S.....................................
MAD88     (61)  .............S.....................................
SA58      (61)  .............S.....................................
JE        (61)  .......ATSSV.S...V.M..............DK........A.TL...
SLE       (61)  ......I.TGG..N..M..V..............TT...Y....E......
MVE       (61)  ..A..Y.ASS.......V.I..............DK........E......
```

FIG. 6

| | | 300 … 351 |
|---|---|---|
| Mosquito | DEN1 | KGVSYVMCT-GSFKLEKEVAETQHGTVLVQVKYEGTDAPCKIPFSSQDEKGVT |
| | DEN2 | KGMSYSMCY-GKFKVVEEIAETQHGTIVIRVQYEGDGSPCKIPLEIMDLDNRH |
| | DEN3 | KGMSYAMCL-NTFVLKKEVSETQHGTILIKVEYKGEDAPCKIPFSTEDGQGKA |
| | DEN4 | KGMSYTMCS-GKFSIDKEMAETQHGTTVVKVKYEGAGAPCKVPIEIRDVNKEK |
| | JE | KGTTYGMCT-EKFSFAKNPADTGHGTVVIELSYSGSDGPCKIPIVSVASLNDM |
| | WN | KGTTYGVCS-KAFKFLGTPADTGHGTVVLELQYTGTDGPCKVPISSVASLNDL |
| | YF | KGTSYKMCT-DKMSFVKNPTDTGHGTAVMQVKVPKG-APCRIPVMVADDLTAS |
| Tick | RSSE | KGLTYTMCDKTKFTWKRAPTDSGHDTVVMEVTFSGT-KPCRIPVRAVAHGSPD |
| | CEE | KGLTYTMCDKTKFTWKRAPTDSGHDTVVMEVTFSGT-KPCRIPVRAVAGHSPD |
| | LI | KGLTYTMCDKSKFAWKRTPTDSGHDTVVMEVTFSGS-KPCRIPVRAVAHGSPD |
| | LGT | KGLTYTVCDKTKFTWKRAPTDSGHDTVVMEVGFSGT-RPCRIPVRAVAHGVPE |
| | POW | KGTTYSMCDKAKFKWKRVPVDSGHDTVVMEVSYTGSDKPCRIPVRAVAHGVPA |
| | KFD | KGMTYTVCEGSKFAWKRPPTDSGHDTVVMEVTYTGS-KPCRIPVRAVAHGEPN |
| | OHF | KGLTYTMCDKAKFTWKRAPTDSGHDTVVMEVAFSGT-KPCRIPVRAVAHGSPD |

| | | 352 … 395 | |
|---|---|---|---|
| Mosquito | DEN1 | Q-NGRLITANPIVIDKEK--PVNIEAE-PPFGESYIVVGAGEKALKLSWFKK | SEQ ID NO:4 |
| | DEN2 | V-LGRLITVNPIVTEKDS--PVNVEAE-PPLGDSYIIIGVEPGQLKLNWFKK | SEQ ID NO:6 |
| | DEN3 | H-NGRLITANPVVTKKEE--PVNIEAE-PPFGESNIVIGIGDKALKINWYRK | SEQ ID NO:5 |
| | DEN4 | V-VGRIISSTPLAENTNS--VTNIELE-RPL-DSYIVIGVGNSALTLHWFRK | SEQ ID NO:7 |
| | JE | TPVGRLVTVNPFVATSSANSKVLVEME-PPFGDSYIVVGRGDKQINHHWHKA | SEQ ID NO:8 |
| | WN | TPVGRLVTVNPFVSVATANAKVLIELE-PPFGDSYIVVGRGEQQINHHWHKS | SEQ ID NO:11 |
| | YF | VNKGILVTVNPIASTNED--EVLIEVN-PPFGDSYIIVGTGDSRLTYQWHKE | SEQ ID NO:13 |
| Tick | RSSE | VNVAMLITPNPTIENNGG---GFIEMQLPP-GDNIIYVG----ELSYQWFQK | SEQ ID NO:26 |
| | CEE | VNVAMLITPNPTIENNGG---GFIEMQLPP-GDNIIYVG----ELSHQWFQK | SEQ ID NO:27 |
| | LI | VNVAMLITPNPTIENDGG---GFIEMQLPP-GDNIIYVG----ELSHQWFQT | SEQ ID NO:17 |
| | LGT | VNVAMLITPNPTMENNGG---GFIEMQLPP-GDNIIYVG----DLNHQWFQK | SEQ ID NO:18 |
| | POW | VNVAMLITPNPTIETNGG---GFIEMQLPP-GDNIIYVG----DLSQQWFQK | SEQ ID NO:20 |
| | KFD | VNVASLITPNPSMENTGG---GFVELQLPP-GDNIIYVG----ELSHQWFQK | SEQ ID NO:15 |
| | OHF | VDVAMLITPNPTIENNGG---GFIEMQLPP-GDNIIYVG----ELKHQWFQK | SEQ ID NO:19 |

FIG. 16

SEQUENCE LISTING

```
<160> NUMBER OF SEQ ID NOS: 27

<210> SEQ ID NO 1
<211> LENGTH: 10962
<212> TYPE: DNA
<213> ORGANISM: West Nile virus
<220> FEATURE:
<221> NAME/KEY: CDS
<222> LOCATION: (97)..(10389)

<400> SEQUENCE: 1
```

-continued

```
agtagttcgc ctgtgtgagc tgacaaactt agtagtgttt gtgaggatta acaacaatta      60

acacagtgcg agctgtttct tggcacgaag atctcg atg tct aag aaa cca gga      114
                                        Met Ser Lys Lys Pro Gly
                                          1               5

ggg ccc ggt aaa aac cgg gct gtc aat atg cta aaa cgc ggt atg ccc      162
Gly Pro Gly Lys Asn Arg Ala Val Asn Met Leu Lys Arg Gly Met Pro
                 10                  15                  20

cgc gga ttg tcc ttg ata gga cta aag agg gct atg ctg agt ctg att      210
Arg Gly Leu Ser Leu Ile Gly Leu Lys Arg Ala Met Leu Ser Leu Ile
             25                  30                  35

gac ggg aag ggc cca ata cgt ttc gtg ttg gct ctt ttg gcg ttt ttc      258
Asp Gly Lys Gly Pro Ile Arg Phe Val Leu Ala Leu Leu Ala Phe Phe
         40                  45                  50

aga ttc act gca atc gct ccg act cgt gcg gtg ctg gac aga tgg aga      306
Arg Phe Thr Ala Ile Ala Pro Thr Arg Ala Val Leu Asp Arg Trp Arg
 55                  60                  65                  70

ggc gtc aac aaa caa aca gca atg aag cat ctc ttg agt ttc aag aaa      354
Gly Val Asn Lys Gln Thr Ala Met Lys His Leu Leu Ser Phe Lys Lys
                 75                  80                  85

gaa cta gga act ctg acc agt gcc atc aac cgc cgg agc aca aaa caa      402
Glu Leu Gly Thr Leu Thr Ser Ala Ile Asn Arg Arg Ser Thr Lys Gln
             90                  95                 100

aag aaa aga gga ggc aca gcg ggc ttt act atc ttg ctt ggg ctg atc      450
Lys Lys Arg Gly Gly Thr Ala Gly Phe Thr Ile Leu Leu Gly Leu Ile
        105                 110                 115

gcc tgt gct gga gct gtg acc ctc tcg aac ttc cag ggc aaa gtg atg      498
Ala Cys Ala Gly Ala Val Thr Leu Ser Asn Phe Gln Gly Lys Val Met
    120                 125                 130

atg aca gtc aat gca acc gat gtc act gac gtg att acc att cca aca      546
Met Thr Val Asn Ala Thr Asp Val Thr Asp Val Ile Thr Ile Pro Thr
135                 140                 145                 150

gct gct ggg aaa aac ctg tgc atc gta agg gct atg gac gta gga tac      594
Ala Ala Gly Lys Asn Leu Cys Ile Val Arg Ala Met Asp Val Gly Tyr
                155                 160                 165

ctt tgt gag gat act atc act tat gaa tgt ccg gtc cta gct gct gga      642
Leu Cys Glu Asp Thr Ile Thr Tyr Glu Cys Pro Val Leu Ala Ala Gly
            170                 175                 180

aat gac cct gaa gac att gac tgc tgg tgc acg aaa tca tct gtt tac      690
Asn Asp Pro Glu Asp Ile Asp Cys Trp Cys Thr Lys Ser Ser Val Tyr
        185                 190                 195

gtg cgc tat gga aga tgc aca aaa act cgg cat tcc cgt cga agc aga      738
Val Arg Tyr Gly Arg Cys Thr Lys Thr Arg His Ser Arg Arg Ser Arg
    200                 205                 210

agg tct ctg aca gtc cag aca cat gga gaa agt aca ctg gcc aac aag      786
Arg Ser Leu Thr Val Gln Thr His Gly Glu Ser Thr Leu Ala Asn Lys
215                 220                 225                 230

aaa gga gct tgg ttg gac agc aca aaa gcc acg aga tat ctg gtg aag      834
Lys Gly Ala Trp Leu Asp Ser Thr Lys Ala Thr Arg Tyr Leu Val Lys
                235                 240                 245

aca gaa tca tgg ata ctg aga aac ccg ggc tac gcc ctc gtt gca gct      882
Thr Glu Ser Trp Ile Leu Arg Asn Pro Gly Tyr Ala Leu Val Ala Ala
            250                 255                 260

gtc att gga tgg atg cta gga agc aac aca atg caa cgc gtc gtg ttt      930
Val Ile Gly Trp Met Leu Gly Ser Asn Thr Met Gln Arg Val Val Phe
        265                 270                 275

gcc att cta ttg ctc ctg gtg gca cca gca tac agc ttc aac tgt tta      978
Ala Ile Leu Leu Leu Leu Val Ala Pro Ala Tyr Ser Phe Asn Cys Leu
    280                 285                 290
```

-continued

```
gga atg agt aac aga gac ttc ctg gag gga gtg tct gga gct aca tgg      1026
Gly Met Ser Asn Arg Asp Phe Leu Glu Gly Val Ser Gly Ala Thr Trp
295                 300                 305                 310

gtt gat ctg gta ctg gaa ggc gat agt tgt gtg acc ata atg tca aaa      1074
Val Asp Leu Val Leu Glu Gly Asp Ser Cys Val Thr Ile Met Ser Lys
                315                 320                 325

gac aag cca acc att gat gtc aaa atg atg aac atg gaa gca gcc aac      1122
Asp Lys Pro Thr Ile Asp Val Lys Met Met Asn Met Glu Ala Ala Asn
            330                 335                 340

ctc gca gat gtg cgc agt tac tgt tac cta gct tcg gtc agt gac ttg      1170
Leu Ala Asp Val Arg Ser Tyr Cys Tyr Leu Ala Ser Val Ser Asp Leu
        345                 350                 355

tca aca aga gct gcg tgt cca acc atg ggt gaa gcc cac aac gag aaa      1218
Ser Thr Arg Ala Ala Cys Pro Thr Met Gly Glu Ala His Asn Glu Lys
    360                 365                 370

aga gct gac ccc gcc ttc gtt tgc aag caa ggc gtt gtg gac aga gga      1266
Arg Ala Asp Pro Ala Phe Val Cys Lys Gln Gly Val Val Asp Arg Gly
375                 380                 385                 390

tgg gga aat ggc tgc gga ctg ttt gga aag ggg agc att gac aca tgt      1314
Trp Gly Asn Gly Cys Gly Leu Phe Gly Lys Gly Ser Ile Asp Thr Cys
                395                 400                 405

gcg aag ttt gcc tgt aca acc aaa gca act gga tgg atc atc cag aag      1362
Ala Lys Phe Ala Cys Thr Thr Lys Ala Thr Gly Trp Ile Ile Gln Lys
            410                 415                 420

gaa aac atc aag tat gag gtt gcc ata ttt gtg cat ggc ccg acg acc      1410
Glu Asn Ile Lys Tyr Glu Val Ala Ile Phe Val His Gly Pro Thr Thr
        425                 430                 435

gtt gaa tct cat ggc aag ata ggg gcc acc cag gct gga aga ttc agt      1458
Val Glu Ser His Gly Lys Ile Gly Ala Thr Gln Ala Gly Arg Phe Ser
    440                 445                 450

ata act cca tcg gcg cca tct tac acg cta aag ttg ggt gag tat ggt      1506
Ile Thr Pro Ser Ala Pro Ser Tyr Thr Leu Lys Leu Gly Glu Tyr Gly
455                 460                 465                 470

gag gtt acg gtt gat tgt gag cca cgg tca gga ata gac acc agc gcc      1554
Glu Val Thr Val Asp Cys Glu Pro Arg Ser Gly Ile Asp Thr Ser Ala
                475                 480                 485

tat tac gtt atg tca gtt ggt gag aag tcc ttc ctg gtt cac cga gaa      1602
Tyr Tyr Val Met Ser Val Gly Glu Lys Ser Phe Leu Val His Arg Glu
            490                 495                 500

tgg ttt atg gat ctg aac ctg cca tgg agc agt gct gga agc acc acg      1650
Trp Phe Met Asp Leu Asn Leu Pro Trp Ser Ser Ala Gly Ser Thr Thr
        505                 510                 515

tgg agg aac cgg gaa aca ctg atg gag ttt gaa gaa cct cat gcc acc      1698
Trp Arg Asn Arg Glu Thr Leu Met Glu Phe Glu Glu Pro His Ala Thr
    520                 525                 530

aaa caa tct gtt gtg gct cta ggg tcg cag gaa ggt gcg ttg cac caa      1746
Lys Gln Ser Val Val Ala Leu Gly Ser Gln Glu Gly Ala Leu His Gln
535                 540                 545                 550

gct ctg gcc gga gcg att cct gtt gag ttc tca agc aac act gtg aag      1794
Ala Leu Ala Gly Ala Ile Pro Val Glu Phe Ser Ser Asn Thr Val Lys
                555                 560                 565

ttg aca tca gga cat ctg aag tgt cgg gtg aag atg gag aag ttg cag      1842
Leu Thr Ser Gly His Leu Lys Cys Arg Val Lys Met Glu Lys Leu Gln
            570                 575                 580

ctg aag gga aca aca tat gga gta tgt tca aaa gcg ttc aaa ttc gct      1890
Leu Lys Gly Thr Thr Tyr Gly Val Cys Ser Lys Ala Phe Lys Phe Ala
        585                 590                 595

agg act ccc gct gac act ggc cac gga acg gtg gtg ttg gaa ctg caa      1938
Arg Thr Pro Ala Asp Thr Gly His Gly Thr Val Val Leu Glu Leu Gln
    600                 605                 610
```

-continued

```
tat acc gga aca gac ggt ccc tgc aaa gtg ccc att tct tcc gta gct      1986
Tyr Thr Gly Thr Asp Gly Pro Cys Lys Val Pro Ile Ser Ser Val Ala
615                 620                 625                 630

tcc ctg aat gac ctc aca cct gtt gga aga ctg gtg acc gtg aat cca      2034
Ser Leu Asn Asp Leu Thr Pro Val Gly Arg Leu Val Thr Val Asn Pro
                635                 640                 645

ttt gtg tct gtg gcc aca gcc aac tcg aag gtt ttg att gaa ctc gaa      2082
Phe Val Ser Val Ala Thr Ala Asn Ser Lys Val Leu Ile Glu Leu Glu
            650                 655                 660

ccc ccg ttt ggt gac tct tac atc gtg gtg gga aga gga gaa cag cag      2130
Pro Pro Phe Gly Asp Ser Tyr Ile Val Val Gly Arg Gly Glu Gln Gln
        665                 670                 675

ata aac cat cac tgg cac aaa tct ggg agc agc att gga aag gcc ttt      2178
Ile Asn His His Trp His Lys Ser Gly Ser Ser Ile Gly Lys Ala Phe
    680                 685                 690

acc acc aca ctc aga gga gct caa cga ctc gca gct ctt gga gat act      2226
Thr Thr Thr Leu Arg Gly Ala Gln Arg Leu Ala Ala Leu Gly Asp Thr
695                 700                 705                 710

gct tgg gat ttt gga tca gtt gga ggg gtt ttc acc tca gtg ggg aaa      2274
Ala Trp Asp Phe Gly Ser Val Gly Gly Val Phe Thr Ser Val Gly Lys
                715                 720                 725

gcc ata cac caa gtc ttt gga gga gct ttt aga tca ctc ttt gga ggg      2322
Ala Ile His Gln Val Phe Gly Gly Ala Phe Arg Ser Leu Phe Gly Gly
            730                 735                 740

atg tcc tgg atc aca cag gga ctt ctg gga gct ctt ctg ttg tgg atg      2370
Met Ser Trp Ile Thr Gln Gly Leu Leu Gly Ala Leu Leu Leu Trp Met
        745                 750                 755

gga atc aat gcc cgt gac agg tca att gct atg acg ttt ctt gcg gtt      2418
Gly Ile Asn Ala Arg Asp Arg Ser Ile Ala Met Thr Phe Leu Ala Val
    760                 765                 770

gga gga gtt ttg ctc ttc ctt tcg gtc aac gtc cat gct gac aca ggc      2466
Gly Gly Val Leu Leu Phe Leu Ser Val Asn Val His Ala Asp Thr Gly
775                 780                 785                 790

tgt gcc att gat att ggc agg caa gag ctc cgg tgc gga agt gga gtg      2514
Cys Ala Ile Asp Ile Gly Arg Gln Glu Leu Arg Cys Gly Ser Gly Val
                795                 800                 805

ttt atc cac aac gat gtg gaa gcc tgg atg gat cgt tac aag ttc tac      2562
Phe Ile His Asn Asp Val Glu Ala Trp Met Asp Arg Tyr Lys Phe Tyr
            810                 815                 820

ccg gag acg cca cag ggc cta gca aaa att atc cag aaa gca cat gca      2610
Pro Glu Thr Pro Gln Gly Leu Ala Lys Ile Ile Gln Lys Ala His Ala
        825                 830                 835

gaa gga gtc tgc ggc ttg cgt tcc gtt tcc aga ctc gag cac caa atg      2658
Glu Gly Val Cys Gly Leu Arg Ser Val Ser Arg Leu Glu His Gln Met
    840                 845                 850

tgg gaa gcc att aag gat gag ctg aac acc ctg ttg aaa gag aat gga      2706
Trp Glu Ala Ile Lys Asp Glu Leu Asn Thr Leu Leu Lys Glu Asn Gly
855                 860                 865                 870

gtc gac ttg agt gtc gtg gtg gaa aaa cag aat ggg atg tac aaa gca      2754
Val Asp Leu Ser Val Val Val Glu Lys Gln Asn Gly Met Tyr Lys Ala
                875                 880                 885

gca cca aaa cgt ttg gct gcc acc acc gaa aaa ctg gag atg ggt tgg      2802
Ala Pro Lys Arg Leu Ala Ala Thr Thr Glu Lys Leu Glu Met Gly Trp
            890                 895                 900

aag gct tgg ggc aag agt atc atc ttt gcg cca gaa cta gct aac aac      2850
Lys Ala Trp Gly Lys Ser Ile Ile Phe Ala Pro Glu Leu Ala Asn Asn
        905                 910                 915

acc ttt gtc atc gac ggt cct gag act gag gaa tgc cca acg gcc aac      2898
Thr Phe Val Ile Asp Gly Pro Glu Thr Glu Glu Cys Pro Thr Ala Asn
```

-continued

```
920                 925                 930

cga gca tgg aac agt atg gag gta gag gac ttt gga ttt gga ctg aca     2946
Arg Ala Trp Asn Ser Met Glu Val Glu Asp Phe Gly Phe Gly Leu Thr
935                 940                 945                 950

agc act cgc atg ttc ctg agg att cgg gaa acg aac aca acg gaa tgc     2994
Ser Thr Arg Met Phe Leu Arg Ile Arg Glu Thr Asn Thr Thr Glu Cys
            955                 960                 965

gac tcg aag atc ata gga acc gcc gtc aag aac aac atg gct gtg cat     3042
Asp Ser Lys Ile Ile Gly Thr Ala Val Lys Asn Asn Met Ala Val His
            970                 975                 980

agt gat cta tca tac tgg ata gag agc gga ctc aac gac acc tgg aag     3090
Ser Asp Leu Ser Tyr Trp Ile Glu Ser Gly Leu Asn Asp Thr Trp Lys
        985                 990                 995

ctt gag agg gcg gtt cta gga gaa gtc aaa tca tgc acc tgg cca gaa     3138
Leu Glu Arg Ala Val Leu Gly Glu Val Lys Ser Cys Thr Trp Pro Glu
   1000                1005                1010

acc cac act ctg tgg ggt gat gga gtt ctg gaa agt gat ctc atc ata     3186
Thr His Thr Leu Trp Gly Asp Gly Val Leu Glu Ser Asp Leu Ile Ile
1015                1020                1025                1030

ccc atc acc ttg gca gga ccc aga agc aac cac aac agg aga cca ggg     3234
Pro Ile Thr Leu Ala Gly Pro Arg Ser Asn His Asn Arg Arg Pro Gly
               1035                1040                1045

tac aaa act cag aac caa ggc cca tgg gat gag ggg cgc gtc gag att     3282
Tyr Lys Thr Gln Asn Gln Gly Pro Trp Asp Glu Gly Arg Val Glu Ile
           1050                1055                1060

gac ttt gac tat tgc cca gga aca aca gta act ata agt gac agt tgc     3330
Asp Phe Asp Tyr Cys Pro Gly Thr Thr Val Thr Ile Ser Asp Ser Cys
       1065                1070                1075

gaa cac cgt gga cct gcg gca cgc aca acc act gag agt ggg aag ctc     3378
Glu His Arg Gly Pro Ala Ala Arg Thr Thr Thr Glu Ser Gly Lys Leu
   1080                1085                1090

atc aca gac tgg tgc tgc aga agt tgc acc ctc cct cca ctg cgc ttc     3426
Ile Thr Asp Trp Cys Cys Arg Ser Cys Thr Leu Pro Pro Leu Arg Phe
1095                1100                1105                1110

cag act gag aat ggc tgt tgg tat gga atg gaa att cga cct acg cgg     3474
Gln Thr Glu Asn Gly Cys Trp Tyr Gly Met Glu Ile Arg Pro Thr Arg
               1115                1120                1125

cac gac gaa aag acc ctc gtg caa tcg aga gtg aat gca tac aac gcc     3522
His Asp Glu Lys Thr Leu Val Gln Ser Arg Val Asn Ala Tyr Asn Ala
           1130                1135                1140

gac atg att gat cct ttt cag ttg ggc ctt atg gtc gtg ttc ttg gcc     3570
Asp Met Ile Asp Pro Phe Gln Leu Gly Leu Met Val Val Phe Leu Ala
       1145                1150                1155

acc cag gag gtc ctt cgc aag agg tgg acg gcc aag atc agc att cca     3618
Thr Gln Glu Val Leu Arg Lys Arg Trp Thr Ala Lys Ile Ser Ile Pro
   1160                1165                1170

gct atc atg ctt gca ctc cta gtc cta gtg ttt ggg ggt att acg tac     3666
Ala Ile Met Leu Ala Leu Leu Val Leu Val Phe Gly Gly Ile Thr Tyr
1175                1180                1185                1190

act gat gtc ctg cga tat gtc att ctc gtc ggc gcc gcg ttt gct gaa     3714
Thr Asp Val Leu Arg Tyr Val Ile Leu Val Gly Ala Ala Phe Ala Glu
               1195                1200                1205

gca aac tca gga gga gac gtc gtg cac ttg gca ctt atg gct aca ttc     3762
Ala Asn Ser Gly Gly Asp Val Val His Leu Ala Leu Met Ala Thr Phe
           1210                1215                1220

aag att caa cca gtc ttt ctg gtg gct tcc ttt ttg aag gca agg tgg     3810
Lys Ile Gln Pro Val Phe Leu Val Ala Ser Phe Leu Lys Ala Arg Trp
       1225                1230                1235

acc aac caa gag agt att ttg ctc atg ctt gca gct gct ttc ttc caa     3858
```

-continued

```
Thr Asn Gln Glu Ser Ile Leu Leu Met Leu Ala Ala Ala Phe Phe Gln
   1240                1245                1250

atg gct tac tat gac gcc aag aat gtt ctg tca tgg gaa gtg cct gac      3906
Met Ala Tyr Tyr Asp Ala Lys Asn Val Leu Ser Trp Glu Val Pro Asp
1255                1260                1265                1270

gtt ttg aac tct ctc tcc gtt gcg tgg atg att ctc aga gct ata agc      3954
Val Leu Asn Ser Leu Ser Val Ala Trp Met Ile Leu Arg Ala Ile Ser
               1275                1280                1285

ttc acc aac act tca aat gtg gtg gtg ccg ctg ctg gcc ctt ttg aca      4002
Phe Thr Asn Thr Ser Asn Val Val Val Pro Leu Leu Ala Leu Leu Thr
           1290                1295                1300

cct gga ttg aaa tgc tta aac ctt gat gtg tac aga att ttg cta ctc      4050
Pro Gly Leu Lys Cys Leu Asn Leu Asp Val Tyr Arg Ile Leu Leu Leu
       1305                1310                1315

atg gtt gga gtt gga agc ctc atc aaa gaa aaa agg agc tct gca gca      4098
Met Val Gly Val Gly Ser Leu Ile Lys Glu Lys Arg Ser Ser Ala Ala
   1320                1325                1330

aaa aag aaa gga gct tgc ctc atc tgc cta gcg ctg gcg tct aca gga      4146
Lys Lys Lys Gly Ala Cys Leu Ile Cys Leu Ala Leu Ala Ser Thr Gly
1335                1340                1345                1350

gtg ttc aat cca atg ata ctt gca gct ggg cta atg gct tgc gac ccc      4194
Val Phe Asn Pro Met Ile Leu Ala Ala Gly Leu Met Ala Cys Asp Pro
               1355                1360                1365

aac cgc aag cgg ggc tgg cct gct aca gaa gtg atg act gca gtt gga      4242
Asn Arg Lys Arg Gly Trp Pro Ala Thr Glu Val Met Thr Ala Val Gly
           1370                1375                1380

ctc atg ttt gcc atc gtt ggg ggt ctg gca gaa ctt gac ata gat tct      4290
Leu Met Phe Ala Ile Val Gly Gly Leu Ala Glu Leu Asp Ile Asp Ser
       1385                1390                1395

atg gct atc ccc atg acc atc gcc gga ctt atg ttc gcg gca ttt gtc      4338
Met Ala Ile Pro Met Thr Ile Ala Gly Leu Met Phe Ala Ala Phe Val
   1400                1405                1410

atc tct gga aag tca aca gac atg tgg att gag agg acg gct gac att      4386
Ile Ser Gly Lys Ser Thr Asp Met Trp Ile Glu Arg Thr Ala Asp Ile
1415                1420                1425                1430

act tgg gag agt gat gct gaa atc aca ggc tct agc gaa aga gta gat      4434
Thr Trp Glu Ser Asp Ala Glu Ile Thr Gly Ser Ser Glu Arg Val Asp
               1435                1440                1445

gtg agg ctg gat gat gat gga aat ttt caa ctg atg aat gac ccc ggg      4482
Val Arg Leu Asp Asp Asp Gly Asn Phe Gln Leu Met Asn Asp Pro Gly
           1450                1455                1460

gca cca tgg aaa att tgg atg ctt agg atg gcc tgc ctg gcg ata agt      4530
Ala Pro Trp Lys Ile Trp Met Leu Arg Met Ala Cys Leu Ala Ile Ser
       1465                1470                1475

gcc tac aca cct tgg gca att ctc ccc tcg gtc atc gga ttc tgg ata      4578
Ala Tyr Thr Pro Trp Ala Ile Leu Pro Ser Val Ile Gly Phe Trp Ile
   1480                1485                1490

acc ctt cag tac aca aag aga gga ggt gtt ctt tgg gac aca cca tca      4626
Thr Leu Gln Tyr Thr Lys Arg Gly Gly Val Leu Trp Asp Thr Pro Ser
1495                1500                1505                1510

ccc aag gag tac aag aag ggt gat acc acc act ggc gtt tac aga atc      4674
Pro Lys Glu Tyr Lys Lys Gly Asp Thr Thr Thr Gly Val Tyr Arg Ile
               1515                1520                1525

atg act cga ggt ctg ctt ggc agt tac caa gct gga gcc gga gtg atg      4722
Met Thr Arg Gly Leu Leu Gly Ser Tyr Gln Ala Gly Ala Gly Val Met
           1530                1535                1540

gta gag ggg gtg ttc cac aca cta tgg cac acc act aag gga gct gct      4770
Val Glu Gly Val Phe His Thr Leu Trp His Thr Thr Lys Gly Ala Ala
       1545                1550                1555
```

-continued

```
ctc atg agt ggt gag gga cgt ctg gat ccc tac tgg ggg agc gtg aaa      4818
Leu Met Ser Gly Glu Gly Arg Leu Asp Pro Tyr Trp Gly Ser Val Lys
   1560                1565                1570

gag gac cga ctt tgc tat ggg ggg cca tgg aaa ctc caa cat aaa tgg      4866
Glu Asp Arg Leu Cys Tyr Gly Gly Pro Trp Lys Leu Gln His Lys Trp
1575                1580                1585                1590

aat gga cat gat gag gtc caa atg att gtc gtg gag cca ggg aaa aat      4914
Asn Gly His Asp Glu Val Gln Met Ile Val Val Glu Pro Gly Lys Asn
               1595                1600                1605

gtg aaa aac gtc cag acc aag ccc gga gtg ttt aag aca cca gaa gga      4962
Val Lys Asn Val Gln Thr Lys Pro Gly Val Phe Lys Thr Pro Glu Gly
           1610                1615                1620

gaa att ggg gca gtt acg cta gac tat cct acc gga acg tca ggt tcc      5010
Glu Ile Gly Ala Val Thr Leu Asp Tyr Pro Thr Gly Thr Ser Gly Ser
       1625                1630                1635

ccc att gta gac aaa aat gga gat gtg att gga ttg tat ggg aac ggc      5058
Pro Ile Val Asp Lys Asn Gly Asp Val Ile Gly Leu Tyr Gly Asn Gly
   1640                1645                1650

gtc atc atg cct aat ggt tca tac ata agc gcc att gtg caa gga gag      5106
Val Ile Met Pro Asn Gly Ser Tyr Ile Ser Ala Ile Val Gln Gly Glu
1655                1660                1665                1670

aga atg gaa gaa ccg gca cca gct ggc ttc gaa cct gaa atg ttg agg      5154
Arg Met Glu Glu Pro Ala Pro Ala Gly Phe Glu Pro Glu Met Leu Arg
               1675                1680                1685

aag aaa cag atc act gtc ctt gat ctg cac ccc gga gca gga aag aca      5202
Lys Lys Gln Ile Thr Val Leu Asp Leu His Pro Gly Ala Gly Lys Thr
           1690                1695                1700

cgc aag ata ctt ccc caa atc atc aag gag gcc atc aac aaa aga ttg      5250
Arg Lys Ile Leu Pro Gln Ile Ile Lys Glu Ala Ile Asn Lys Arg Leu
       1705                1710                1715

agg acg gct gtg ctg gca ccc acc agg gtc gtt gct gct gag atg tct      5298
Arg Thr Ala Val Leu Ala Pro Thr Arg Val Val Ala Ala Glu Met Ser
   1720                1725                1730

gag gcc ctg aga gga ctt ccc att cgg tac caa acc tca gca gtg cac      5346
Glu Ala Leu Arg Gly Leu Pro Ile Arg Tyr Gln Thr Ser Ala Val His
1735                1740                1745                1750

aga gag cac agt gga aat gag atc gtt gat gtc atg tgc cat gcc acc      5394
Arg Glu His Ser Gly Asn Glu Ile Val Asp Val Met Cys His Ala Thr
               1755                1760                1765

ctc aca cac agg ctg atg tct cca cac aga gtc ccc aac tac aac ctg      5442
Leu Thr His Arg Leu Met Ser Pro His Arg Val Pro Asn Tyr Asn Leu
           1770                1775                1780

ttc ata atg gat gaa gcc cat ttc acg gat cca gcg agc atc gca gcc      5490
Phe Ile Met Asp Glu Ala His Phe Thr Asp Pro Ala Ser Ile Ala Ala
       1785                1790                1795

aga gga tac ata gca acc aag gtt gaa ttg ggc gaa gcc gcc gcg att      5538
Arg Gly Tyr Ile Ala Thr Lys Val Glu Leu Gly Glu Ala Ala Ala Ile
   1800                1805                1810

ttc atg acg gca acg cca ccc ggg act tct gac ccc ttt cca gag tct      5586
Phe Met Thr Ala Thr Pro Pro Gly Thr Ser Asp Pro Phe Pro Glu Ser
1815                1820                1825                1830

aat gct cct atc tcg gac atg caa aca gag atc cca gac aga gcc tgg      5634
Asn Ala Pro Ile Ser Asp Met Gln Thr Glu Ile Pro Asp Arg Ala Trp
               1835                1840                1845

aac act gga tat gaa tgg ata act gag tat gtt gga aag acc gtt tgg      5682
Asn Thr Gly Tyr Glu Trp Ile Thr Glu Tyr Val Gly Lys Thr Val Trp
           1850                1855                1860

ttt gtt cca agt gtg aaa atg gga aat gag att gcc ctc tgt ctg caa      5730
Phe Val Pro Ser Val Lys Met Gly Asn Glu Ile Ala Leu Cys Leu Gln
       1865                1870                1875
```

-continued

```
cgg gcg ggg aag aag gtt atc cag ctg aac aga aag tcc tat gag aca      5778
Arg Ala Gly Lys Lys Val Ile Gln Leu Asn Arg Lys Ser Tyr Glu Thr
   1880                1885                1890

gag tac ccc aag tgt aag aac gat gat tgg gat ttt gtc atc acc aca      5826
Glu Tyr Pro Lys Cys Lys Asn Asp Asp Trp Asp Phe Val Ile Thr Thr
1895                1900                1905                1910

gac ata tca gaa atg gga gcc aac ttc aag gcg agc aga gtg atc gac      5874
Asp Ile Ser Glu Met Gly Ala Asn Phe Lys Ala Ser Arg Val Ile Asp
                1915                1920                1925

agc cgc aaa agc gtg aaa ccc acc atc att gag gaa ggt gat gga aga      5922
Ser Arg Lys Ser Val Lys Pro Thr Ile Ile Glu Glu Gly Asp Gly Arg
            1930                1935                1940

gtc atc ctg ggg gaa ccc tca gcc atc acg gct gcc agc gct gct cag      5970
Val Ile Leu Gly Glu Pro Ser Ala Ile Thr Ala Ala Ser Ala Ala Gln
        1945                1950                1955

cgg aga gga cgc ata gga aga aac cca tca caa gtt ggt gat gag tat      6018
Arg Arg Gly Arg Ile Gly Arg Asn Pro Ser Gln Val Gly Asp Glu Tyr
   1960                1965                1970

tgc tat gga ggg cac aca aat gag gat gat tcc aac ttt gct cac tgg      6066
Cys Tyr Gly Gly His Thr Asn Glu Asp Asp Ser Asn Phe Ala His Trp
1975                1980                1985                1990

aca gag gct cgc atc atg cta gac aac atc aac atg ccg aat ggt ctg      6114
Thr Glu Ala Arg Ile Met Leu Asp Asn Ile Asn Met Pro Asn Gly Leu
                1995                2000                2005

gtg gct caa cta tat cag cct gag cgc gag aag gtg tac acc atg gac      6162
Val Ala Gln Leu Tyr Gln Pro Glu Arg Glu Lys Val Tyr Thr Met Asp
            2010                2015                2020

ggg gaa tac agg ctc aga ggg gaa gaa cgg aag aac ttc ctt gaa ttc      6210
Gly Glu Tyr Arg Leu Arg Gly Glu Glu Arg Lys Asn Phe Leu Glu Phe
        2025                2030                2035

ctg aga aca gct gat tta cca gtc tgg ctc gct tac aaa gtg gca gca      6258
Leu Arg Thr Ala Asp Leu Pro Val Trp Leu Ala Tyr Lys Val Ala Ala
   2040                2045                2050

gca gga ata tca tac cat gac cgg aaa tgg tgc ttt gat gga cct cga      6306
Ala Gly Ile Ser Tyr His Asp Arg Lys Trp Cys Phe Asp Gly Pro Arg
2055                2060                2065                2070

acc aac acg att ctt gaa gac aac aat gaa gtt gaa gtc atc acg aag      6354
Thr Asn Thr Ile Leu Glu Asp Asn Asn Glu Val Glu Val Ile Thr Lys
                2075                2080                2085

ttg ggt gag aga aag atc cta aga ccc agg tgg gca gat gct aga gtg      6402
Leu Gly Glu Arg Lys Ile Leu Arg Pro Arg Trp Ala Asp Ala Arg Val
            2090                2095                2100

tac tca gac cat caa gct cta aag tcc ttc aaa gat ttt gca tcg ggg      6450
Tyr Ser Asp His Gln Ala Leu Lys Ser Phe Lys Asp Phe Ala Ser Gly
        2105                2110                2115

aaa cga tca caa atc ggg ctc gtt gag gtg ctc ggg aga atg cct gaa      6498
Lys Arg Ser Gln Ile Gly Leu Val Glu Val Leu Gly Arg Met Pro Glu
   2120                2125                2130

cac ttc atg gtg aaa act tgg gag gca ttg gac acg atg tat gtg gtg      6546
His Phe Met Val Lys Thr Trp Glu Ala Leu Asp Thr Met Tyr Val Val
2135                2140                2145                2150

gcg acc gct gaa aaa gga ggc cga gct cac agg atg gct ctt gag gag      6594
Ala Thr Ala Glu Lys Gly Gly Arg Ala His Arg Met Ala Leu Glu Glu
                2155                2160                2165

cta ccg gac gcc ctt cag aca ata gtt ttg att gca cta ttg agt gtg      6642
Leu Pro Asp Ala Leu Gln Thr Ile Val Leu Ile Ala Leu Leu Ser Val
            2170                2175                2180

atg tcc tta ggt gtg ttt ttt cta ctc atg caa agg aag ggc att ggt      6690
Met Ser Leu Gly Val Phe Phe Leu Leu Met Gln Arg Lys Gly Ile Gly
```

-continued

```
        2185                2190                2195

aag att ggc ttg gga gga gta atc tta gga gct gcc aca ttc ttc tgc      6738
Lys Ile Gly Leu Gly Gly Val Ile Leu Gly Ala Ala Thr Phe Phe Cys
    2200                2205                2210

tgg atg gct gaa gtc cca gga acg aaa ata gca ggc atg ctc ctg ctt      6786
Trp Met Ala Glu Val Pro Gly Thr Lys Ile Ala Gly Met Leu Leu Leu
2215                2220                2225                2230

tcc ctg ctg ctc atg att gtt ttg att ccg gag ccg gaa aag cag cgc      6834
Ser Leu Leu Leu Met Ile Val Leu Ile Pro Glu Pro Glu Lys Gln Arg
                2235                2240                2245

tca cag act gat aac cag ctc gcc gtg ttc ttg atc tgt gtg ctc aca      6882
Ser Gln Thr Asp Asn Gln Leu Ala Val Phe Leu Ile Cys Val Leu Thr
            2250                2255                2260

ctg gtc ggc gcc gtg gct gcc aat gaa atg ggc tgg ctg gac aag acc      6930
Leu Val Gly Ala Val Ala Ala Asn Glu Met Gly Trp Leu Asp Lys Thr
        2265                2270                2275

aag aat gac att ggc agc ctg ttg ggg cac agg cca gaa gct aga gag      6978
Lys Asn Asp Ile Gly Ser Leu Leu Gly His Arg Pro Glu Ala Arg Glu
    2280                2285                2290

acg acc ctg gga gtt gag agc ttc tta ctt gat ctg cgg ccg gcc acg      7026
Thr Thr Leu Gly Val Glu Ser Phe Leu Leu Asp Leu Arg Pro Ala Thr
2295                2300                2305                2310

gca tgg tcg ctc tat gcc gta acg aca gcc gtt ctc acc cct ttg ctg      7074
Ala Trp Ser Leu Tyr Ala Val Thr Thr Ala Val Leu Thr Pro Leu Leu
                2315                2320                2325

aag cat cta atc acg tca gac tac atc aac act tcg ttg acc tca ata      7122
Lys His Leu Ile Thr Ser Asp Tyr Ile Asn Thr Ser Leu Thr Ser Ile
            2330                2335                2340

aac gtc caa gcc agc gcg ttg ttc act ttg gcc aga ggc ttc cct ttt      7170
Asn Val Gln Ala Ser Ala Leu Phe Thr Leu Ala Arg Gly Phe Pro Phe
        2345                2350                2355

gtg gac gtt ggt gtg tca gct ctc ttg ctg gcg gtc ggg tgc tgg ggt      7218
Val Asp Val Gly Val Ser Ala Leu Leu Leu Ala Val Gly Cys Trp Gly
    2360                2365                2370

cag gtg act ctg act gtg act gtg act gca gct gct ctg ctc ttt tgc      7266
Gln Val Thr Leu Thr Val Thr Val Thr Ala Ala Ala Leu Leu Phe Cys
2375                2380                2385                2390

cac tat gct tac atg gtg cca ggc tgg caa gcg gaa gcc atg cga tct      7314
His Tyr Ala Tyr Met Val Pro Gly Trp Gln Ala Glu Ala Met Arg Ser
                2395                2400                2405

gcc cag cgg cgg aca gct gct ggc atc atg aaa aat gta gtg gtg gat      7362
Ala Gln Arg Arg Thr Ala Ala Gly Ile Met Lys Asn Val Val Val Asp
            2410                2415                2420

ggg atc gtg gcc act gat gta cct gaa ctt gaa cga aca act cca gtc      7410
Gly Ile Val Ala Thr Asp Val Pro Glu Leu Glu Arg Thr Thr Pro Val
        2425                2430                2435

atg cag aaa aaa gtt gga cag atc ata ttg atc ttg gta tca atg gcc      7458
Met Gln Lys Lys Val Gly Gln Ile Ile Leu Ile Leu Val Ser Met Ala
    2440                2445                2450

gcg gtg gtc gtc aat cca tca gtg aga acc gtc aga gag gcc gga att      7506
Ala Val Val Val Asn Pro Ser Val Arg Thr Val Arg Glu Ala Gly Ile
2455                2460                2465                2470

ctg act aca gca gca gca gtc acc cta tgg gag aat ggt gct agt tca      7554
Leu Thr Thr Ala Ala Ala Val Thr Leu Trp Glu Asn Gly Ala Ser Ser
                2475                2480                2485

gtg tgg aat gca acg aca gct att ggc ctt tgt cac atc atg cga gga      7602
Val Trp Asn Ala Thr Thr Ala Ile Gly Leu Cys His Ile Met Arg Gly
            2490                2495                2500

gga tgg ctc tcg tgt ctc tcc atc atg tgg act ctc atc aaa aac atg      7650
```

-continued

```
Gly Trp Leu Ser Cys Leu Ser Ile Met Trp Thr Leu Ile Lys Asn Met
       2505                2510                2515

gag aaa cca ggc ctc aag agg ggt gga gcc aaa gga cgc acg cta ggg     7698
Glu Lys Pro Gly Leu Lys Arg Gly Gly Ala Lys Gly Arg Thr Leu Gly
   2520                2525                2530

gaa gtt tgg aag gag aga ctc aac cac atg acg aag gaa gaa ttt acc     7746
Glu Val Trp Lys Glu Arg Leu Asn His Met Thr Lys Glu Glu Phe Thr
2535                2540                2545                2550

aga tac aga aaa gaa gcc atc act gaa gtt gac cgc tcc gca gca aaa     7794
Arg Tyr Arg Lys Glu Ala Ile Thr Glu Val Asp Arg Ser Ala Ala Lys
               2555                2560                2565

cat gct agg aga gag gga aac atc act gga ggc cac cca gtc tca cgg     7842
His Ala Arg Arg Glu Gly Asn Ile Thr Gly Gly His Pro Val Ser Arg
           2570                2575                2580

gga acc gcg aaa tta cgg tgg tta gtg gaa agg cgt ttc ctc gag cca     7890
Gly Thr Ala Lys Leu Arg Trp Leu Val Glu Arg Arg Phe Leu Glu Pro
       2585                2590                2595

gtg gga aag gtt gtg gat ctc ggg tgt ggt aga ggc ggc tgg tgc tat     7938
Val Gly Lys Val Val Asp Leu Gly Cys Gly Arg Gly Gly Trp Cys Tyr
   2600                2605                2610

tac atg gct acc cag aag agg gta cag gaa gtg aaa ggg tac acg aaa     7986
Tyr Met Ala Thr Gln Lys Arg Val Gln Glu Val Lys Gly Tyr Thr Lys
2615                2620                2625                2630

gga gga cct ggc cat gaa gaa cca caa ctg gtg cag agc tat ggt tgg     8034
Gly Gly Pro Gly His Glu Glu Pro Gln Leu Val Gln Ser Tyr Gly Trp
               2635                2640                2645

aat att gtt acc atg aag agt gga gtc gac gtc ttc tac aga cca tca     8082
Asn Ile Val Thr Met Lys Ser Gly Val Asp Val Phe Tyr Arg Pro Ser
           2650                2655                2660

gaa gcg agc gac aca ctg ctc tgt gac att gga gag tca tcg tca agt     8130
Glu Ala Ser Asp Thr Leu Leu Cys Asp Ile Gly Glu Ser Ser Ser Ser
       2665                2670                2675

gcc gag gta gaa gaa cac cgc acc gtc cgt gtc ctg gag atg gtg gaa     8178
Ala Glu Val Glu Glu His Arg Thr Val Arg Val Leu Glu Met Val Glu
   2680                2685                2690

gat tgg ttg cac aga gga ccg aag gaa ttc tgc atc aaa gtg cta tgc     8226
Asp Trp Leu His Arg Gly Pro Lys Glu Phe Cys Ile Lys Val Leu Cys
2695                2700                2705                2710

cct tac atg ccc aaa gtg att gag aag atg gaa aca ctc caa agg cga     8274
Pro Tyr Met Pro Lys Val Ile Glu Lys Met Glu Thr Leu Gln Arg Arg
               2715                2720                2725

tat gga ggt ggc ctt ata aga aac ccc ctt tca cgc aac tct acc cat     8322
Tyr Gly Gly Gly Leu Ile Arg Asn Pro Leu Ser Arg Asn Ser Thr His
           2730                2735                2740

gag atg tac tgg gtg agc cac gct tca ggc aat atc gtc cac tcc gtc     8370
Glu Met Tyr Trp Val Ser His Ala Ser Gly Asn Ile Val His Ser Val
       2745                2750                2755

aac atg aca agc cag gtg ctt ctg ggg agg atg gaa aag aaa aca tgg     8418
Asn Met Thr Ser Gln Val Leu Leu Gly Arg Met Glu Lys Lys Thr Trp
   2760                2765                2770

aag gga ccc cag ttt gag gaa gat gtc aac ttg gga agt gga acg cgg     8466
Lys Gly Pro Gln Phe Glu Glu Asp Val Asn Leu Gly Ser Gly Thr Arg
2775                2780                2785                2790

gca gta ggg aag cct ctc ctc aat tct gat act agc aag atc aag aac     8514
Ala Val Gly Lys Pro Leu Leu Asn Ser Asp Thr Ser Lys Ile Lys Asn
               2795                2800                2805

cga att gag agg ctg aag aaa gaa tac agc tcc aca tgg cac cag gat     8562
Arg Ile Glu Arg Leu Lys Lys Glu Tyr Ser Ser Thr Trp His Gln Asp
           2810                2815                2820
```

-continued

```
gcg aac cac ccc tac agg acc tgg aac tac cac gga agc tat gaa gtg      8610
Ala Asn His Pro Tyr Arg Thr Trp Asn Tyr His Gly Ser Tyr Glu Val
       2825                2830                2835

aaa cca acc ggc tca gcc agc tcc ctt gtg aat ggg gta gtc aga tta      8658
Lys Pro Thr Gly Ser Ala Ser Ser Leu Val Asn Gly Val Val Arg Leu
   2840                2845                2850

ctc tca aaa cca tgg gac act atc acc aat gtg acc acg atg gcc atg      8706
Leu Ser Lys Pro Trp Asp Thr Ile Thr Asn Val Thr Thr Met Ala Met
2855                2860                2865                2870

aca gac acc act cct ttc ggt caa caa cga gtg ttc aag gaa aag gtg      8754
Thr Asp Thr Thr Pro Phe Gly Gln Gln Arg Val Phe Lys Glu Lys Val
               2875                2880                2885

gac aca aag gct cca gag cct cca gaa gga gtc aaa tac gtc ctc aat      8802
Asp Thr Lys Ala Pro Glu Pro Pro Glu Gly Val Lys Tyr Val Leu Asn
           2890                2895                2900

gag acc acg aac tgg ctg tgg gct ttt tta gcc cgc gat aag aaa ccc      8850
Glu Thr Thr Asn Trp Leu Trp Ala Phe Leu Ala Arg Asp Lys Lys Pro
       2905                2910                2915

agg atg tgt tcc cgg gag gaa ttt att gga aaa gtc aac agt aat gcc      8898
Arg Met Cys Ser Arg Glu Glu Phe Ile Gly Lys Val Asn Ser Asn Ala
   2920                2925                2930

gcc cta gga gcg atg ttt gaa gaa cag aac caa tgg aag aac gcc cgg      8946
Ala Leu Gly Ala Met Phe Glu Glu Gln Asn Gln Trp Lys Asn Ala Arg
2935                2940                2945                2950

gaa gct gta gag gat cca aag ttt tgg gag atg gtg gat gag gag cgt      8994
Glu Ala Val Glu Asp Pro Lys Phe Trp Glu Met Val Asp Glu Glu Arg
               2955                2960                2965

gaa gcg cat ctc cgt gga gaa tgc aac acc tgc atc tac aac atg atg      9042
Glu Ala His Leu Arg Gly Glu Cys Asn Thr Cys Ile Tyr Asn Met Met
           2970                2975                2980

gga aag aga gag aag aag cct gga gag ttc ggc aaa gct aaa ggc agc      9090
Gly Lys Arg Glu Lys Lys Pro Gly Glu Phe Gly Lys Ala Lys Gly Ser
       2985                2990                2995

aga gcc atc tgg ttc atg tgg ctg ggg gcc cgc ttc ctg gag ttt gaa      9138
Arg Ala Ile Trp Phe Met Trp Leu Gly Ala Arg Phe Leu Glu Phe Glu
   3000                3005                3010

gct ctc gga ttc ctc aat gaa gac cac tgg ctg ggt agg aag aac tca      9186
Ala Leu Gly Phe Leu Asn Glu Asp His Trp Leu Gly Arg Lys Asn Ser
3015                3020                3025                3030

gga gga gga gtt gaa ggc tta gga ctg cag aag ctc ggg tac atc ttg      9234
Gly Gly Gly Val Glu Gly Leu Gly Leu Gln Lys Leu Gly Tyr Ile Leu
               3035                3040                3045

aag gaa gtt gga aca aag cct gga gga aag gtt tac gct gat gat acc      9282
Lys Glu Val Gly Thr Lys Pro Gly Gly Lys Val Tyr Ala Asp Asp Thr
           3050                3055                3060

gca ggc tgg gac aca cgc atc acc aaa gct gac ctc gag aat gaa gcg      9330
Ala Gly Trp Asp Thr Arg Ile Thr Lys Ala Asp Leu Glu Asn Glu Ala
       3065                3070                3075

aag gtt ctt gaa ctg ctg gat gga gaa cat cga cgt tta gcg cgg tcc      9378
Lys Val Leu Glu Leu Leu Asp Gly Glu His Arg Arg Leu Ala Arg Ser
   3080                3085                3090

atc atc gag ctc aca tac cga cac aaa gtc gtg aaa gtg atg agg cca      9426
Ile Ile Glu Leu Thr Tyr Arg His Lys Val Val Lys Val Met Arg Pro
3095                3100                3105                3110

gcg gcc gac ggg aaa act gtg atg gac gtc atc tct aga gag gat cag      9474
Ala Ala Asp Gly Lys Thr Val Met Asp Val Ile Ser Arg Glu Asp Gln
               3115                3120                3125

aga gga agc ggt cag gta gtg act tac gcc ctg aac acc ttc acc aat      9522
Arg Gly Ser Gly Gln Val Val Thr Tyr Ala Leu Asn Thr Phe Thr Asn
           3130                3135                3140
```

-continued

```
cta gca gtt cag ctg gtc aga atg atg gag ggg gag ggg gtc att gga      9570
Leu Ala Val Gln Leu Val Arg Met Met Glu Gly Glu Gly Val Ile Gly
       3145                3150                3155

ccc gat gat gtt gaa aaa ctg gga aaa gga aaa ggc cct aag gtc aga      9618
Pro Asp Asp Val Glu Lys Leu Gly Lys Gly Lys Gly Pro Lys Val Arg
   3160                3165                3170

acc tgg ctg ttt gag aat ggc gag gag cgt ctc agt cgc atg gcc gtc      9666
Thr Trp Leu Phe Glu Asn Gly Glu Glu Arg Leu Ser Arg Met Ala Val
3175               3180                3185                3190

agc ggt gat gac tgc gtg gtg aaa cct ttg gac gac cgc ttc gcc aca      9714
Ser Gly Asp Asp Cys Val Val Lys Pro Leu Asp Asp Arg Phe Ala Thr
               3195                3200                3205

tca cta cac ttc cta aat gct atg tca aag gtc cgc aaa gac atc cag      9762
Ser Leu His Phe Leu Asn Ala Met Ser Lys Val Arg Lys Asp Ile Gln
           3210                3215                3220

gaa tgg aaa ccc tcg acg ggg tgg tat gac tgg cag cag gtt cca ttc      9810
Glu Trp Lys Pro Ser Thr Gly Trp Tyr Asp Trp Gln Gln Val Pro Phe
       3225                3230                3235

tgt tca aac cat ttc acg gaa ctg atc atg aag gac ggc agg acg ctg      9858
Cys Ser Asn His Phe Thr Glu Leu Ile Met Lys Asp Gly Arg Thr Leu
   3240                3245                3250

gtg gtc ccg tgt cgt gga caa gac gag ttg att gga cgt gcc agg atc      9906
Val Val Pro Cys Arg Gly Gln Asp Glu Leu Ile Gly Arg Ala Arg Ile
3255               3260                3265                3270

tct cca ggg gct gga tgg aat gtg cgc gac acc gcc tgc ctg gcg aag      9954
Ser Pro Gly Ala Gly Trp Asn Val Arg Asp Thr Ala Cys Leu Ala Lys
               3275                3280                3285

tca tac gcg cag atg tgg ctg ctg ctt tat ttc cac cgt aga gac ctg     10002
Ser Tyr Ala Gln Met Trp Leu Leu Leu Tyr Phe His Arg Arg Asp Leu
           3290                3295                3300

aga ttg atg gcc aat gcc atc tgt tcc gct gtg cct gcc aac tgg gtt     10050
Arg Leu Met Ala Asn Ala Ile Cys Ser Ala Val Pro Ala Asn Trp Val
       3305                3310                3315

ccc aca ggg cgt acc act tgg tcg atc cac gca aaa gga gaa tgg atg     10098
Pro Thr Gly Arg Thr Thr Trp Ser Ile His Ala Lys Gly Glu Trp Met
   3320                3325                3330

acg acg gaa gac atg ctc gca gtc tgg aac aga gtg tgg att gag gag     10146
Thr Thr Glu Asp Met Leu Ala Val Trp Asn Arg Val Trp Ile Glu Glu
3335               3340                3345                3350

aat gag tgg atg gaa gac aaa aca cca gtt gag agg tgg agt gat gtt     10194
Asn Glu Trp Met Glu Asp Lys Thr Pro Val Glu Arg Trp Ser Asp Val
               3355                3360                3365

cca tac tct gga aag aga gag gac att tgg tgt ggc agt ttg atc ggc     10242
Pro Tyr Ser Gly Lys Arg Glu Asp Ile Trp Cys Gly Ser Leu Ile Gly
           3370                3375                3380

aca cga acc cgc gcc act tgg gct gaa aat atc cat gtg gca atc aat     10290
Thr Arg Thr Arg Ala Thr Trp Ala Glu Asn Ile His Val Ala Ile Asn
       3385                3390                3395

cag gtc cgt tca gtg att gga gaa gag aag tat gtg gat tac atg agc     10338
Gln Val Arg Ser Val Ile Gly Glu Glu Lys Tyr Val Asp Tyr Met Ser
   3400                3405                3410

tcc ttg agg agg tat gaa gac acc att gta gtg gag gac act gtt ttg     10386
Ser Leu Arg Arg Tyr Glu Asp Thr Ile Val Val Glu Asp Thr Val Leu
3415               3420                3425                3430

taa aagatagtat tatagttagt ttagtgtaaa taggatttat tgagaatgga          10439

agtcaggcca gattaatgct gccaccggaa gttgagtaga cggtgctgcc tgcggctcaa   10499

ccccaggagg actgggtgac caaagctgcg aggtgatcca cgtaagccct cagaaccgtc   10559
```

-continued

```
tcggaaggag gaccccacgt gctttagcct caaagcccag tgtcagacca cactttaatg  10619

tgccactctg cggagagtgc agtctgcgat agtgccccag gtggactggg ttaacaaagg  10679

caaaacatcg ccccacgcgg ccataaccct ggctatggtg ttaaccaggg agaagggact  10739

agaggttaga ggagaccccg cgtaaaaaag tgcacggccc aacttggctg aagctgtaag  10799

ccaagggaag gactagaggt tagaggagac cccgtgccaa aaacaccaaa agaaacagca  10859

tattgacacc tgggatagac taggggatct tctgctctgc acaaccagcc acacggcaca  10919

gtgcgccgac ataggtggct ggtggtgcta gaacacagga tct                    10962


<210> SEQ ID NO 2
<211> LENGTH: 3430
<212> TYPE: PRT
<213> ORGANISM: West Nile virus

<400> SEQUENCE: 2

Met Ser Lys Lys Pro Gly Gly Pro Gly Lys Asn Arg Ala Val Asn Met
1               5                   10                  15

Leu Lys Arg Gly Met Pro Arg Gly Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Thr Lys Gln Lys Lys Arg Gly Gly Thr Ala Gly Phe Thr
            100                 105                 110

Ile Leu Leu Gly Leu Ile Ala Cys Ala Gly Ala Val Thr Leu Ser Asn
        115                 120                 125

Phe Gln Gly Lys Val Met Met Thr Val Asn Ala Thr Asp Val Thr Asp
    130                 135                 140

Val Ile Thr Ile Pro Thr Ala Ala Gly Lys Asn Leu Cys Ile Val Arg
145                 150                 155                 160

Ala Met Asp Val Gly Tyr Leu Cys Glu Asp Thr Ile Thr Tyr Glu Cys
                165                 170                 175

Pro Val Leu Ala Ala Gly Asn Asp Pro Glu Asp Ile Asp Cys Trp Cys
            180                 185                 190

Thr Lys Ser Ser Val Tyr Val Arg Tyr Gly Arg Cys Thr Lys Thr Arg
        195                 200                 205

His Ser Arg Arg Ser Arg Arg Ser Leu Thr Val Gln Thr His Gly Glu
    210                 215                 220

Ser Thr Leu Ala Asn Lys Lys Gly Ala Trp Leu Asp Ser Thr Lys Ala
225                 230                 235                 240

Thr Arg Tyr Leu Val Lys Thr Glu Ser Trp Ile Leu Arg Asn Pro Gly
                245                 250                 255

Tyr Ala Leu Val Ala Ala Val Ile Gly Trp Met Leu Gly Ser Asn Thr
            260                 265                 270

Met Gln Arg Val Val Phe Ala Ile Leu Leu Leu Leu Val Ala Pro Ala
        275                 280                 285

Tyr Ser Phe Asn Cys Leu Gly Met Ser Asn Arg Asp Phe Leu Glu Gly
    290                 295                 300
```

-continued

```
Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                325                 330                 335

Asn Met Glu Ala Ala Asn Leu Ala Asp Val Arg Ser Tyr Cys Tyr Leu
            340                 345                 350

Ala Ser Val Ser Asp Leu Ser Thr Arg Ala Ala Cys Pro Thr Met Gly
        355                 360                 365

Glu Ala His Asn Glu Lys Arg Ala Asp Pro Ala Phe Val Cys Lys Gln
    370                 375                 380

Gly Val Val Asp Arg Gly Trp Gly Asn Gly Cys Gly Leu Phe Gly Lys
385                 390                 395                 400

Gly Ser Ile Asp Thr Cys Ala Lys Phe Ala Cys Thr Thr Lys Ala Thr
                405                 410                 415

Gly Trp Ile Ile Gln Lys Glu Asn Ile Lys Tyr Glu Val Ala Ile Phe
            420                 425                 430

Val His Gly Pro Thr Thr Val Glu Ser His Gly Lys Ile Gly Ala Thr
        435                 440                 445

Gln Ala Gly Arg Phe Ser Ile Thr Pro Ser Ala Pro Ser Tyr Thr Leu
    450                 455                 460

Lys Leu Gly Glu Tyr Gly Glu Val Thr Val Asp Cys Glu Pro Arg Ser
465                 470                 475                 480

Gly Ile Asp Thr Ser Ala Tyr Tyr Val Met Ser Val Gly Glu Lys Ser
                485                 490                 495

Phe Leu Val His Arg Glu Trp Phe Met Asp Leu Asn Leu Pro Trp Ser
            500                 505                 510

Ser Ala Gly Ser Thr Thr Trp Arg Asn Arg Glu Thr Leu Met Glu Phe
        515                 520                 525

Glu Glu Pro His Ala Thr Lys Gln Ser Val Val Ala Leu Gly Ser Gln
    530                 535                 540

Glu Gly Ala Leu His Gln Ala Leu Ala Gly Ala Ile Pro Val Glu Phe
545                 550                 555                 560

Ser Ser Asn Thr Val Lys Leu Thr Ser Gly His Leu Lys Cys Arg Val
                565                 570                 575

Lys Met Glu Lys Leu Gln Leu Lys Gly Thr Thr Tyr Gly Val Cys Ser
            580                 585                 590

Lys Ala Phe Lys Phe Ala Arg Thr Pro Ala Asp Thr Gly His Gly Thr
        595                 600                 605

Val Val Leu Glu Leu Gln Tyr Thr Gly Thr Asp Gly Pro Cys Lys Val
    610                 615                 620

Pro Ile Ser Ser Val Ala Ser Leu Asn Asp Leu Thr Pro Val Gly Arg
625                 630                 635                 640

Leu Val Thr Val Asn Pro Phe Val Ser Val Ala Thr Ala Asn Ser Lys
                645                 650                 655

Val Leu Ile Glu Leu Glu Pro Pro Phe Gly Asp Ser Tyr Ile Val Val
            660                 665                 670

Gly Arg Gly Glu Gln Gln Ile Asn His His Trp His Lys Ser Gly Ser
        675                 680                 685

Ser Ile Gly Lys Ala Phe Thr Thr Thr Leu Arg Gly Ala Gln Arg Leu
    690                 695                 700

Ala Ala Leu Gly Asp Thr Ala Trp Asp Phe Gly Ser Val Gly Gly Val
705                 710                 715                 720

Phe Thr Ser Val Gly Lys Ala Ile His Gln Val Phe Gly Gly Ala Phe
```

-continued

```
                725                 730                 735

Arg Ser Leu Phe Gly Gly Met Ser Trp Ile Thr Gln Gly Leu Leu Gly
            740                 745                 750

Ala Leu Leu Leu Trp Met Gly Ile Asn Ala Arg Asp Arg Ser Ile Ala
        755                 760                 765

Met Thr Phe Leu Ala Val Gly Gly Val Leu Leu Phe Leu Ser Val Asn
    770                 775                 780

Val His Ala Asp Thr Gly Cys Ala Ile Asp Ile Gly Arg Gln Glu Leu
785                 790                 795                 800

Arg Cys Gly Ser Gly Val Phe Ile His Asn Asp Val Glu Ala Trp Met
                805                 810                 815

Asp Arg Tyr Lys Phe Tyr Pro Glu Thr Pro Gln Gly Leu Ala Lys Ile
            820                 825                 830

Ile Gln Lys Ala His Ala Glu Gly Val Cys Gly Leu Arg Ser Val Ser
        835                 840                 845

Arg Leu Glu His Gln Met Trp Glu Ala Ile Lys Asp Glu Leu Asn Thr
    850                 855                 860

Leu Leu Lys Glu Asn Gly Val Asp Leu Ser Val Val Val Glu Lys Gln
865                 870                 875                 880

Asn Gly Met Tyr Lys Ala Ala Pro Lys Arg Leu Ala Ala Thr Thr Glu
                885                 890                 895

Lys Leu Glu Met Gly Trp Lys Ala Trp Gly Lys Ser Ile Ile Phe Ala
            900                 905                 910

Pro Glu Leu Ala Asn Asn Thr Phe Val Ile Asp Gly Pro Glu Thr Glu
        915                 920                 925

Glu Cys Pro Thr Ala Asn Arg Ala Trp Asn Ser Met Glu Val Glu Asp
    930                 935                 940

Phe Gly Phe Gly Leu Thr Ser Thr Arg Met Phe Leu Arg Ile Arg Glu
945                 950                 955                 960

Thr Asn Thr Thr Glu Cys Asp Ser Lys Ile Ile Gly Thr Ala Val Lys
                965                 970                 975

Asn Asn Met Ala Val His Ser Asp Leu Ser Tyr Trp Ile Glu Ser Gly
            980                 985                 990

Leu Asn Asp Thr Trp Lys Leu Glu Arg Ala Val Leu Gly Glu Val Lys
        995                 1000                1005

Ser Cys Thr Trp Pro Glu Thr His Thr Leu Trp Gly Asp Gly Val Leu
   1010                 1015                1020

Glu Ser Asp Leu Ile Ile Pro Ile Thr Leu Ala Gly Pro Arg Ser Asn
1025                1030                1035                1040

His Asn Arg Arg Pro Gly Tyr Lys Thr Gln Asn Gln Gly Pro Trp Asp
               1045                1050                1055

Glu Gly Arg Val Glu Ile Asp Phe Asp Tyr Cys Pro Gly Thr Thr Val
           1060                1065                1070

Thr Ile Ser Asp Ser Cys Glu His Arg Gly Pro Ala Ala Arg Thr Thr
       1075                1080                1085

Thr Glu Ser Gly Lys Leu Ile Thr Asp Trp Cys Cys Arg Ser Cys Thr
   1090                1095                1100

Leu Pro Pro Leu Arg Phe Gln Thr Glu Asn Gly Cys Trp Tyr Gly Met
1105                1110                1115                1120

Glu Ile Arg Pro Thr Arg His Asp Glu Lys Thr Leu Val Gln Ser Arg
               1125                1130                1135

Val Asn Ala Tyr Asn Ala Asp Met Ile Asp Pro Phe Gln Leu Gly Leu
           1140                1145                1150
```

-continued

```
Met Val Val Phe Leu Ala Thr Gln Glu Val Leu Arg Lys Arg Trp Thr
       1155                1160                1165

Ala Lys Ile Ser Ile Pro Ala Ile Met Leu Ala Leu Leu Val Leu Val
   1170                1175                1180

Phe Gly Gly Ile Thr Tyr Thr Asp Val Leu Arg Tyr Val Ile Leu Val
1185                1190                1195                1200

Gly Ala Ala Phe Ala Glu Ala Asn Ser Gly Gly Asp Val Val His Leu
               1205                1210                1215

Ala Leu Met Ala Thr Phe Lys Ile Gln Pro Val Phe Leu Val Ala Ser
           1220                1225                1230

Phe Leu Lys Ala Arg Trp Thr Asn Gln Glu Ser Ile Leu Leu Met Leu
       1235                1240                1245

Ala Ala Ala Phe Phe Gln Met Ala Tyr Tyr Asp Ala Lys Asn Val Leu
   1250                1255                1260

Ser Trp Glu Val Pro Asp Val Leu Asn Ser Leu Ser Val Ala Trp Met
1265                1270                1275                1280

Ile Leu Arg Ala Ile Ser Phe Thr Asn Thr Ser Asn Val Val Val Pro
               1285                1290                1295

Leu Leu Ala Leu Leu Thr Pro Gly Leu Lys Cys Leu Asn Leu Asp Val
           1300                1305                1310

Tyr Arg Ile Leu Leu Leu Met Val Gly Val Gly Ser Leu Ile Lys Glu
       1315                1320                1325

Lys Arg Ser Ser Ala Ala Lys Lys Lys Gly Ala Cys Leu Ile Cys Leu
   1330                1335                1340

Ala Leu Ala Ser Thr Gly Val Phe Asn Pro Met Ile Leu Ala Ala Gly
1345                1350                1355                1360

Leu Met Ala Cys Asp Pro Asn Arg Lys Arg Gly Trp Pro Ala Thr Glu
               1365                1370                1375

Val Met Thr Ala Val Gly Leu Met Phe Ala Ile Val Gly Gly Leu Ala
           1380                1385                1390

Glu Leu Asp Ile Asp Ser Met Ala Ile Pro Met Thr Ile Ala Gly Leu
       1395                1400                1405

Met Phe Ala Ala Phe Val Ile Ser Gly Lys Ser Thr Asp Met Trp Ile
   1410                1415                1420

Glu Arg Thr Ala Asp Ile Thr Trp Glu Ser Asp Ala Glu Ile Thr Gly
1425                1430                1435                1440

Ser Ser Glu Arg Val Asp Val Arg Leu Asp Asp Asp Gly Asn Phe Gln
               1445                1450                1455

Leu Met Asn Asp Pro Gly Ala Pro Trp Lys Ile Trp Met Leu Arg Met
           1460                1465                1470

Ala Cys Leu Ala Ile Ser Ala Tyr Thr Pro Trp Ala Ile Leu Pro Ser
       1475                1480                1485

Val Ile Gly Phe Trp Ile Thr Leu Gln Tyr Thr Lys Arg Gly Gly Val
   1490                1495                1500

Leu Trp Asp Thr Pro Ser Pro Lys Glu Tyr Lys Lys Gly Asp Thr Thr
1505                1510                1515                1520

Thr Gly Val Tyr Arg Ile Met Thr Arg Gly Leu Leu Gly Ser Tyr Gln
               1525                1530                1535

Ala Gly Ala Gly Val Met Val Glu Gly Val Phe His Thr Leu Trp His
           1540                1545                1550

Thr Thr Lys Gly Ala Ala Leu Met Ser Gly Glu Gly Arg Leu Asp Pro
       1555                1560                1565
```

-continued

```
Tyr Trp Gly Ser Val Lys Glu Asp Arg Leu Cys Tyr Gly Gly Pro Trp
   1570                1575                1580

Lys Leu Gln His Lys Trp Asn Gly His Asp Glu Val Gln Met Ile Val
1585                1590                1595                1600

Val Glu Pro Gly Lys Asn Val Lys Asn Val Gln Thr Lys Pro Gly Val
               1605                1610                1615

Phe Lys Thr Pro Glu Gly Glu Ile Gly Ala Val Thr Leu Asp Tyr Pro
           1620                1625                1630

Thr Gly Thr Ser Gly Ser Pro Ile Val Asp Lys Asn Gly Asp Val Ile
       1635                1640                1645

Gly Leu Tyr Gly Asn Gly Val Ile Met Pro Asn Gly Ser Tyr Ile Ser
   1650                1655                1660

Ala Ile Val Gln Gly Glu Arg Met Glu Glu Pro Ala Pro Ala Gly Phe
1665                1670                1675                1680

Glu Pro Glu Met Leu Arg Lys Lys Gln Ile Thr Val Leu Asp Leu His
               1685                1690                1695

Pro Gly Ala Gly Lys Thr Arg Lys Ile Leu Pro Gln Ile Ile Lys Glu
           1700                1705                1710

Ala Ile Asn Lys Arg Leu Arg Thr Ala Val Leu Ala Pro Thr Arg Val
       1715                1720                1725

Val Ala Ala Glu Met Ser Glu Ala Leu Arg Gly Leu Pro Ile Arg Tyr
   1730                1735                1740

Gln Thr Ser Ala Val His Arg Glu His Ser Gly Asn Glu Ile Val Asp
1745                1750                1755                1760

Val Met Cys His Ala Thr Leu Thr His Arg Leu Met Ser Pro His Arg
               1765                1770                1775

Val Pro Asn Tyr Asn Leu Phe Ile Met Asp Glu Ala His Phe Thr Asp
           1780                1785                1790

Pro Ala Ser Ile Ala Ala Arg Gly Tyr Ile Ala Thr Lys Val Glu Leu
       1795                1800                1805

Gly Glu Ala Ala Ala Ile Phe Met Thr Ala Thr Pro Pro Gly Thr Ser
   1810                1815                1820

Asp Pro Phe Pro Glu Ser Asn Ala Pro Ile Ser Asp Met Gln Thr Glu
1825                1830                1835                1840

Ile Pro Asp Arg Ala Trp Asn Thr Gly Tyr Glu Trp Ile Thr Glu Tyr
               1845                1850                1855

Val Gly Lys Thr Val Trp Phe Val Pro Ser Val Lys Met Gly Asn Glu
           1860                1865                1870

Ile Ala Leu Cys Leu Gln Arg Ala Gly Lys Lys Val Ile Gln Leu Asn
       1875                1880                1885

Arg Lys Ser Tyr Glu Thr Glu Tyr Pro Lys Cys Lys Asn Asp Asp Trp
   1890                1895                1900

Asp Phe Val Ile Thr Thr Asp Ile Ser Glu Met Gly Ala Asn Phe Lys
1905                1910                1915                1920

Ala Ser Arg Val Ile Asp Ser Arg Lys Ser Val Lys Pro Thr Ile Ile
               1925                1930                1935

Glu Glu Gly Asp Gly Arg Val Ile Leu Gly Glu Pro Ser Ala Ile Thr
           1940                1945                1950

Ala Ala Ser Ala Ala Gln Arg Arg Gly Arg Ile Gly Arg Asn Pro Ser
       1955                1960                1965

Gln Val Gly Asp Glu Tyr Cys Tyr Gly Gly His Thr Asn Glu Asp Asp
   1970                1975                1980

Ser Asn Phe Ala His Trp Thr Glu Ala Arg Ile Met Leu Asp Asn Ile
```

-continued

```
1985                1990                1995                2000

Asn Met Pro Asn Gly Leu Val Ala Gln Leu Tyr Gln Pro Glu Arg Glu
                2005                2010                2015

Lys Val Tyr Thr Met Asp Gly Glu Tyr Arg Leu Arg Gly Glu Glu Arg
            2020                2025                2030

Lys Asn Phe Leu Glu Phe Leu Arg Thr Ala Asp Leu Pro Val Trp Leu
        2035                2040                2045

Ala Tyr Lys Val Ala Ala Ala Gly Ile Ser Tyr His Asp Arg Lys Trp
    2050                2055                2060

Cys Phe Asp Gly Pro Arg Thr Asn Thr Ile Leu Glu Asp Asn Asn Glu
2065                2070                2075                2080

Val Glu Val Ile Thr Lys Leu Gly Glu Arg Lys Ile Leu Arg Pro Arg
                2085                2090                2095

Trp Ala Asp Ala Arg Val Tyr Ser Asp His Gln Ala Leu Lys Ser Phe
            2100                2105                2110

Lys Asp Phe Ala Ser Gly Lys Arg Ser Gln Ile Gly Leu Val Glu Val
        2115                2120                2125

Leu Gly Arg Met Pro Glu His Phe Met Val Lys Thr Trp Glu Ala Leu
    2130                2135                2140

Asp Thr Met Tyr Val Val Ala Thr Ala Glu Lys Gly Gly Arg Ala His
2145                2150                2155                2160

Arg Met Ala Leu Glu Glu Leu Pro Asp Ala Leu Gln Thr Ile Val Leu
                2165                2170                2175

Ile Ala Leu Leu Ser Val Met Ser Leu Gly Val Phe Phe Leu Leu Met
            2180                2185                2190

Gln Arg Lys Gly Ile Gly Lys Ile Gly Leu Gly Gly Val Ile Leu Gly
        2195                2200                2205

Ala Ala Thr Phe Phe Cys Trp Met Ala Glu Val Pro Gly Thr Lys Ile
    2210                2215                2220

Ala Gly Met Leu Leu Leu Ser Leu Leu Leu Met Ile Val Leu Ile Pro
2225                2230                2235                2240

Glu Pro Glu Lys Gln Arg Ser Gln Thr Asp Asn Gln Leu Ala Val Phe
                2245                2250                2255

Leu Ile Cys Val Leu Thr Leu Val Gly Ala Val Ala Ala Asn Glu Met
            2260                2265                2270

Gly Trp Leu Asp Lys Thr Lys Asn Asp Ile Gly Ser Leu Leu Gly His
        2275                2280                2285

Arg Pro Glu Ala Arg Glu Thr Thr Leu Gly Val Glu Ser Phe Leu Leu
    2290                2295                2300

Asp Leu Arg Pro Ala Thr Ala Trp Ser Leu Tyr Ala Val Thr Thr Ala
2305                2310                2315                2320

Val Leu Thr Pro Leu Leu Lys His Leu Ile Thr Ser Asp Tyr Ile Asn
                2325                2330                2335

Thr Ser Leu Thr Ser Ile Asn Val Gln Ala Ser Ala Leu Phe Thr Leu
            2340                2345                2350

Ala Arg Gly Phe Pro Phe Val Asp Val Gly Val Ser Ala Leu Leu Leu
        2355                2360                2365

Ala Val Gly Cys Trp Gly Gln Val Thr Leu Thr Val Thr Val Thr Ala
    2370                2375                2380

Ala Ala Leu Leu Phe Cys His Tyr Ala Tyr Met Val Pro Gly Trp Gln
2385                2390                2395                2400

Ala Glu Ala Met Arg Ser Ala Gln Arg Arg Thr Ala Ala Gly Ile Met
                2405                2410                2415
```

-continued

```
Lys Asn Val Val Val Asp Gly Ile Val Ala Thr Asp Val Pro Glu Leu
          2420                2425                2430

Glu Arg Thr Thr Pro Val Met Gln Lys Lys Val Gly Gln Ile Ile Leu
      2435                2440                2445

Ile Leu Val Ser Met Ala Ala Val Val Val Asn Pro Ser Val Arg Thr
   2450                2455                2460

Val Arg Glu Ala Gly Ile Leu Thr Thr Ala Ala Ala Val Thr Leu Trp
2465                2470                2475                2480

Glu Asn Gly Ala Ser Ser Val Trp Asn Ala Thr Thr Ala Ile Gly Leu
              2485                2490                2495

Cys His Ile Met Arg Gly Gly Trp Leu Ser Cys Leu Ser Ile Met Trp
          2500                2505                2510

Thr Leu Ile Lys Asn Met Glu Lys Pro Gly Leu Lys Arg Gly Gly Ala
      2515                2520                2525

Lys Gly Arg Thr Leu Gly Glu Val Trp Lys Glu Arg Leu Asn His Met
   2530                2535                2540

Thr Lys Glu Glu Phe Thr Arg Tyr Arg Lys Glu Ala Ile Thr Glu Val
2545                2550                2555                2560

Asp Arg Ser Ala Ala Lys His Ala Arg Arg Glu Gly Asn Ile Thr Gly
              2565                2570                2575

Gly His Pro Val Ser Arg Gly Thr Ala Lys Leu Arg Trp Leu Val Glu
          2580                2585                2590

Arg Arg Phe Leu Glu Pro Val Gly Lys Val Val Asp Leu Gly Cys Gly
      2595                2600                2605

Arg Gly Gly Trp Cys Tyr Tyr Met Ala Thr Gln Lys Arg Val Gln Glu
   2610                2615                2620

Val Lys Gly Tyr Thr Lys Gly Gly Pro Gly His Glu Glu Pro Gln Leu
2625                2630                2635                2640

Val Gln Ser Tyr Gly Trp Asn Ile Val Thr Met Lys Ser Gly Val Asp
              2645                2650                2655

Val Phe Tyr Arg Pro Ser Glu Ala Ser Asp Thr Leu Leu Cys Asp Ile
          2660                2665                2670

Gly Glu Ser Ser Ser Ser Ala Glu Val Glu Glu His Arg Thr Val Arg
      2675                2680                2685

Val Leu Glu Met Val Glu Asp Trp Leu His Arg Gly Pro Lys Glu Phe
   2690                2695                2700

Cys Ile Lys Val Leu Cys Pro Tyr Met Pro Lys Val Ile Glu Lys Met
2705                2710                2715                2720

Glu Thr Leu Gln Arg Arg Tyr Gly Gly Gly Leu Ile Arg Asn Pro Leu
              2725                2730                2735

Ser Arg Asn Ser Thr His Glu Met Tyr Trp Val Ser His Ala Ser Gly
          2740                2745                2750

Asn Ile Val His Ser Val Asn Met Thr Ser Gln Val Leu Leu Gly Arg
      2755                2760                2765

Met Glu Lys Lys Thr Trp Lys Gly Pro Gln Phe Glu Glu Asp Val Asn
   2770                2775                2780

Leu Gly Ser Gly Thr Arg Ala Val Gly Lys Pro Leu Leu Asn Ser Asp
2785                2790                2795                2800

Thr Ser Lys Ile Lys Asn Arg Ile Glu Arg Leu Lys Lys Glu Tyr Ser
              2805                2810                2815

Ser Thr Trp His Gln Asp Ala Asn His Pro Tyr Arg Thr Trp Asn Tyr
          2820                2825                2830
```

-continued

```
His Gly Ser Tyr Glu Val Lys Pro Thr Gly Ser Ala Ser Ser Leu Val
       2835                2840                2845

Asn Gly Val Val Arg Leu Leu Ser Lys Pro Trp Asp Thr Ile Thr Asn
   2850                2855                2860

Val Thr Thr Met Ala Met Thr Asp Thr Thr Pro Phe Gly Gln Gln Arg
2865                2870                2875                2880

Val Phe Lys Glu Lys Val Asp Thr Lys Ala Pro Glu Pro Pro Glu Gly
               2885                2890                2895

Val Lys Tyr Val Leu Asn Glu Thr Thr Asn Trp Leu Trp Ala Phe Leu
           2900                2905                2910

Ala Arg Asp Lys Lys Pro Arg Met Cys Ser Arg Glu Glu Phe Ile Gly
       2915                2920                2925

Lys Val Asn Ser Asn Ala Ala Leu Gly Ala Met Phe Glu Glu Gln Asn
   2930                2935                2940

Gln Trp Lys Asn Ala Arg Glu Ala Val Glu Asp Pro Lys Phe Trp Glu
2945                2950                2955                2960

Met Val Asp Glu Glu Arg Glu Ala His Leu Arg Gly Glu Cys Asn Thr
               2965                2970                2975

Cys Ile Tyr Asn Met Met Gly Lys Arg Glu Lys Lys Pro Gly Glu Phe
           2980                2985                2990

Gly Lys Ala Lys Gly Ser Arg Ala Ile Trp Phe Met Trp Leu Gly Ala
       2995                3000                3005

Arg Phe Leu Glu Phe Glu Ala Leu Gly Phe Leu Asn Glu Asp His Trp
   3010                3015                3020

Leu Gly Arg Lys Asn Ser Gly Gly Gly Val Glu Gly Leu Gly Leu Gln
3025                3030                3035                3040

Lys Leu Gly Tyr Ile Leu Lys Glu Val Gly Thr Lys Pro Gly Gly Lys
               3045                3050                3055

Val Tyr Ala Asp Asp Thr Ala Gly Trp Asp Thr Arg Ile Thr Lys Ala
           3060                3065                3070

Asp Leu Glu Asn Glu Ala Lys Val Leu Glu Leu Leu Asp Gly Glu His
       3075                3080                3085

Arg Arg Leu Ala Arg Ser Ile Ile Glu Leu Thr Tyr Arg His Lys Val
   3090                3095                3100

Val Lys Val Met Arg Pro Ala Ala Asp Gly Lys Thr Val Met Asp Val
3105                3110                3115                3120

Ile Ser Arg Glu Asp Gln Arg Gly Ser Gly Gln Val Val Thr Tyr Ala
               3125                3130                3135

Leu Asn Thr Phe Thr Asn Leu Ala Val Gln Leu Val Arg Met Met Glu
           3140                3145                3150

Gly Glu Gly Val Ile Gly Pro Asp Asp Val Glu Lys Leu Gly Lys Gly
       3155                3160                3165

Lys Gly Pro Lys Val Arg Thr Trp Leu Phe Glu Asn Gly Glu Glu Arg
   3170                3175                3180

Leu Ser Arg Met Ala Val Ser Gly Asp Asp Cys Val Val Lys Pro Leu
3185                3190                3195                3200

Asp Asp Arg Phe Ala Thr Ser Leu His Phe Leu Asn Ala Met Ser Lys
               3205                3210                3215

Val Arg Lys Asp Ile Gln Glu Trp Lys Pro Ser Thr Gly Trp Tyr Asp
           3220                3225                3230

Trp Gln Gln Val Pro Phe Cys Ser Asn His Phe Thr Glu Leu Ile Met
       3235                3240                3245

Lys Asp Gly Arg Thr Leu Val Val Pro Cys Arg Gly Gln Asp Glu Leu
```

-continued

```
3250                3255                3260

Ile Gly Arg Ala Arg Ile Ser Pro Gly Ala Gly Trp Asn Val Arg Asp
3265                3270                3275                3280

Thr Ala Cys Leu Ala Lys Ser Tyr Ala Gln Met Trp Leu Leu Leu Tyr
                3285                3290                3295

Phe His Arg Arg Asp Leu Arg Leu Met Ala Asn Ala Ile Cys Ser Ala
            3300                3305                3310

Val Pro Ala Asn Trp Val Pro Thr Gly Arg Thr Thr Trp Ser Ile His
        3315                3320                3325

Ala Lys Gly Glu Trp Met Thr Thr Glu Asp Met Leu Ala Val Trp Asn
    3330                3335                3340

Arg Val Trp Ile Glu Glu Asn Glu Trp Met Glu Asp Lys Thr Pro Val
3345                3350                3355                3360

Glu Arg Trp Ser Asp Val Pro Tyr Ser Gly Lys Arg Glu Asp Ile Trp
                3365                3370                3375

Cys Gly Ser Leu Ile Gly Thr Arg Thr Arg Ala Thr Trp Ala Glu Asn
            3380                3385                3390

Ile His Val Ala Ile Asn Gln Val Arg Ser Val Ile Gly Glu Glu Lys
        3395                3400                3405

Tyr Val Asp Tyr Met Ser Ser Leu Arg Arg Tyr Glu Asp Thr Ile Val
    3410                3415                3420

Val Glu Asp Thr Val Leu
3425                3430


<210> SEQ ID NO 3
<211> LENGTH: 497
<212> TYPE: PRT
<213> ORGANISM: West Nile virus

<400> SEQUENCE: 3

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Asp Val Arg Ser Tyr Cys Tyr Leu Ala Ser
    50                  55                  60

Val Ser Asp Leu Ser Thr Arg Ala Ala Cys Pro Thr Met Gly Glu Ala
65                  70                  75                  80

His Asn Glu Lys Arg Ala Asp Pro Ala Phe Val Cys Lys Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Thr Thr Lys Ala Thr Gly Trp
        115                 120                 125

Ile Ile Gln Lys Glu Asn Ile Lys Tyr Glu Val Ala Ile Phe Val His
    130                 135                 140

Gly Pro Thr Thr Val Glu Ser His Gly Lys Ile Gly Ala Thr Gln Ala
145                 150                 155                 160

Gly Arg Phe Ser Ile Thr Pro Ser Ala Pro Ser Tyr Thr Leu Lys Leu
                165                 170                 175

Gly Glu Tyr Gly Glu Val Thr Val Asp Cys Glu Pro Arg Ser Gly Ile
            180                 185                 190
```

-continued

```
Asp Thr Ser Ala Tyr Tyr Val Met Ser Val Gly Glu Lys Ser Phe Leu
        195                 200                 205

Val His Arg Glu Trp Phe Met Asp Leu Asn Leu Pro Trp Ser Ser Ala
    210                 215                 220

Gly Ser Thr Thr Trp Arg Asn Arg Glu Thr Leu Met Glu Phe Glu Glu
225                 230                 235                 240

Pro His Ala Thr Lys Gln Ser Val Val Ala Leu Gly Ser Gln Glu Gly
                245                 250                 255

Ala Leu His Gln Ala Leu Ala Gly Ala Ile Pro Val Glu Phe Ser Ser
            260                 265                 270

Asn Thr Val Lys Leu Thr Ser Gly His Leu Lys Cys Arg Val Lys Met
        275                 280                 285

Glu Lys Leu Gln Leu Lys Gly Thr Thr Tyr Gly Val Cys Ser Lys Ala
    290                 295                 300

Phe Lys Phe Ala Arg Thr Pro Ala Asp Thr Gly His Gly Thr Val Val
305                 310                 315                 320

Leu Glu Leu Gln Tyr Thr Gly Thr Asp Gly Pro Cys Lys Val Pro Ile
                325                 330                 335

Ser Ser Val Ala Ser Leu Asn Asp Leu Thr Pro Val Gly Arg Leu Val
            340                 345                 350

Thr Val Asn Pro Phe Val Ser Val Ala Thr Ala Asn Ser Lys Val Leu
        355                 360                 365

Ile Glu Leu Glu Pro Pro Phe Gly Asp Ser Tyr Ile Val Val Gly Arg
    370                 375                 380

Gly Glu Gln Gln Ile Asn His His Trp His Lys Ser Gly Ser Ser Ile
385                 390                 395                 400

Gly Lys Ala Phe Thr Thr Thr Leu Arg Gly Ala Gln Arg Leu Ala Ala
                405                 410                 415

Leu Gly Asp Thr Ala Trp Asp Phe Gly Ser Val Gly Gly Val Phe Thr
            420                 425                 430

Ser Val Gly Lys Ala Ile His Gln Val Phe Gly Gly Ala Phe Arg Ser
        435                 440                 445

Leu Phe Gly Gly Met Ser Trp Ile Thr Gln Gly Leu Leu Gly Ala Leu
    450                 455                 460

Leu Leu Trp Met Gly Ile Asn Ala Arg Asp Arg Ser Ile Ala Met Thr
465                 470                 475                 480

Phe Leu Ala Val Gly Gly Val Leu Leu Phe Leu Ser Val Asn Val His
                485                 490                 495

Ala


<210> SEQ ID NO 4
<211> LENGTH: 100
<212> TYPE: PRT
<213> ORGANISM: Flavivirus sp.

<400> SEQUENCE: 4

Lys Gly Val Ser Tyr Val Met Cys Thr Gly Ser Phe Lys Leu Glu Lys
  1               5                  10                  15

Glu Val Ala Glu Thr Gln His Gly Thr Val Leu Val Gln Val Lys Tyr
             20                  25                  30

Glu Gly Thr Asp Ala Pro Cys Lys Ile Pro Phe Ser Ser Gln Asp Glu
         35                  40                  45

Lys Gly Val Thr Gln Asn Gly Arg Leu Ile Thr Ala Asn Pro Ile Val
     50                  55                  60
```

-continued

```
Ile Asp Lys Glu Lys Pro Val Asn Ile Glu Ala Glu Pro Pro Phe Gly
 65                  70                  75                  80

Glu Ser Tyr Ile Val Val Gly Ala Gly Glu Lys Ala Leu Lys Leu Ser
                 85                  90                  95

Trp Phe Lys Lys
            100


<210> SEQ ID NO 5
<211> LENGTH: 100
<212> TYPE: PRT
<213> ORGANISM: Flavivirus sp.

<400> SEQUENCE: 5

Lys Gly Met Ser Tyr Ala Met Cys Leu Asn Thr Phe Val Leu Lys Lys
  1               5                  10                  15

Glu Val Ser Glu Thr Gln His Gly Thr Ile Leu Ile Lys Val Glu Tyr
            20                  25                  30

Lys Gly Glu Asp Ala Pro Cys Lys Ile Pro Phe Ser Thr Glu Asp Gly
        35                  40                  45

Gln Gly Lys Ala His Asn Gly Arg Leu Ile Thr Ala Asn Pro Val Val
     50                  55                  60

Thr Lys Lys Glu Glu Pro Val Asn Ile Glu Ala Glu Pro Pro Phe Gly
 65                  70                  75                  80

Glu Ser Asn Ile Val Ile Gly Ile Gly Asp Lys Ala Leu Lys Ile Asn
                 85                  90                  95

Trp Tyr Arg Lys
            100


<210> SEQ ID NO 6
<211> LENGTH: 100
<212> TYPE: PRT
<213> ORGANISM: Flavivirus sp.

<400> SEQUENCE: 6

Lys Gly Met Ser Tyr Ser Met Cys Thr Gly Lys Phe Lys Val Val Glu
  1               5                  10                  15

Glu Ile Ala Glu Thr Gln His Gly Thr Ile Val Ile Arg Val Gln Tyr
            20                  25                  30

Glu Gly Asp Gly Ser Pro Cys Lys Ile Pro Leu Glu Ile Met Asp Leu
        35                  40                  45

Asp Asn Arg His Val Leu Gly Arg Leu Ile Thr Val Asn Pro Ile Val
     50                  55                  60

Thr Glu Lys Asp Ser Pro Val Asn Val Glu Ala Glu Pro Pro Leu Gly
 65                  70                  75                  80

Asp Ser Tyr Ile Ile Ile Gly Val Glu Pro Gly Gln Leu Lys Leu Asn
                 85                  90                  95

Trp Phe Lys Lys
            100


<210> SEQ ID NO 7
<211> LENGTH: 99
<212> TYPE: PRT
<213> ORGANISM: Flavivirus sp.

<400> SEQUENCE: 7

Lys Gly Met Ser Tyr Thr Met Cys Ser Gly Lys Phe Ser Ile Asp Lys
  1               5                  10                  15

Glu Met Ala Glu Thr Gln His Gly Thr Thr Val Val Lys Val Lys Tyr
```

-continued

```
            20                  25                  30

Glu Gly Ala Gly Ala Pro Cys Lys Val Pro Ile Glu Ile Arg Asp Val
        35                  40                  45

Asn Lys Glu Lys Val Val Gly Arg Ile Ile Ser Ser Thr Pro Leu Ala
    50                  55                  60

Glu Asn Thr Asn Ser Val Thr Asn Ile Glu Leu Glu Arg Pro Leu Asp
65                  70                  75                  80

Ser Tyr Ile Val Ile Gly Val Gly Asn Ser Ala Leu Thr Leu His Trp
                85                  90                  95

Phe Arg Lys


<210> SEQ ID NO 8
<211> LENGTH: 103
<212> TYPE: PRT
<213> ORGANISM: Flavivirus sp.

<400> SEQUENCE: 8

Lys Gly Thr Thr Tyr Gly Met Cys Thr Glu Lys Phe Ser Phe Ala Lys
1               5                   10                  15

Asn Pro Ala Asp Thr Gly His Gly Thr Val Val Ile Glu Leu Ser Tyr
            20                  25                  30

Ser Gly Ser Asp Gly Pro Cys Lys Ile Pro Ile Val Ser Val Ala Ser
        35                  40                  45

Leu Asn Asp Met Thr Pro Val Gly Arg Leu Val Thr Val Asn Pro Phe
    50                  55                  60

Val Ala Thr Ser Ser Ala Asn Ser Lys Val Leu Val Glu Met Glu Pro
65                  70                  75                  80

Pro Phe Gly Asp Ser Tyr Ile Val Val Gly Arg Gly Asp Lys Gln Ile
                85                  90                  95

Asn His His Trp His Lys Ala
            100


<210> SEQ ID NO 9
<211> LENGTH: 103
<212> TYPE: PRT
<213> ORGANISM: Flavivirus sp.

<400> SEQUENCE: 9

Lys Gly Thr Thr Tyr Gly Met Cys Thr Glu Lys Phe Thr Phe Ser Lys
1               5                   10                  15

Asn Pro Ala Asp Thr Gly His Gly Thr Val Val Leu Glu Leu Gln Tyr
            20                  25                  30

Thr Gly Ser Asp Gly Pro Cys Lys Ile Pro Ile Ser Ser Val Ala Ser
        35                  40                  45

Leu Asn Asp Met Thr Pro Val Gly Arg Met Val Thr Ala Asn Pro Tyr
    50                  55                  60

Val Ala Ser Ser Thr Ala Asn Ala Lys Val Leu Val Glu Ile Glu Pro
65                  70                  75                  80

Pro Phe Gly Asp Ser Tyr Ile Val Val Gly Arg Gly Asp Lys Gln Ile
                85                  90                  95

Asn His His Trp His Lys Glu
            100


<210> SEQ ID NO 10
<211> LENGTH: 103
<212> TYPE: PRT
<213> ORGANISM: Flavivirus sp.
```

-continued

<400> SEQUENCE: 10

```
Lys Gly Thr Thr Tyr Gly Val Cys Ser Lys Ala Phe Arg Phe Leu Gly
1               5                   10                  15

Thr Pro Ala Asp Thr Gly His Gly Thr Val Val Leu Glu Leu Gln Tyr
            20                  25                  30

Thr Gly Thr Asp Gly Pro Cys Lys Ile Pro Ile Ser Ser Val Ala Ser
        35                  40                  45

Leu Asn Asp Leu Thr Pro Val Gly Arg Leu Val Thr Val Asn Pro Phe
    50                  55                  60

Val Ser Val Ser Thr Ala Asn Ala Lys Val Leu Ile Glu Leu Glu Pro
65                  70                  75                  80

Pro Phe Gly Asp Ser Tyr Ile Val Val Gly Arg Gly Glu Gln Gln Ile
                85                  90                  95

Asn His His Trp His Lys Ser
            100
```

<210> SEQ ID NO 11
<211> LENGTH: 103
<212> TYPE: PRT
<213> ORGANISM: West Nile virus

<400> SEQUENCE: 11

```
Lys Gly Thr Thr Tyr Gly Val Cys Ser Lys Ala Phe Lys Phe Leu Gly
1               5                   10                  15

Thr Pro Ala Asp Thr Gly His Gly Thr Val Val Leu Glu Leu Gln Tyr
            20                  25                  30

Thr Gly Thr Asp Gly Pro Cys Lys Val Pro Ile Ser Ser Val Ala Ser
        35                  40                  45

Leu Asn Asp Leu Thr Pro Val Gly Arg Leu Val Thr Val Asn Pro Phe
    50                  55                  60

Val Ser Val Ala Thr Ala Asn Ala Lys Val Leu Ile Glu Leu Glu Pro
65                  70                  75                  80

Pro Phe Gly Asp Ser Tyr Ile Val Val Gly Arg Gly Glu Gln Gln Ile
                85                  90                  95

Asn His His Trp His Lys Ser
            100
```

<210> SEQ ID NO 12
<211> LENGTH: 103
<212> TYPE: PRT
<213> ORGANISM: Flavivirus sp.

<400> SEQUENCE: 12

```
Lys Gly Thr Thr Tyr Gly Met Cys Asp Ser Ala Phe Thr Phe Ser Lys
1               5                   10                  15

Asn Pro Thr Asp Thr Gly His Gly Thr Val Ile Val Glu Leu Gln Tyr
            20                  25                  30

Thr Gly Ser Asn Gly Pro Cys Arg Val Pro Ile Ser Val Thr Ala Asn
        35                  40                  45

Leu Met Asp Leu Thr Pro Val Gly Arg Leu Val Thr Val Asn Pro Phe
    50                  55                  60

Ile Ser Thr Gly Gly Ala Asn Asn Lys Val Met Ile Glu Val Glu Pro
65                  70                  75                  80

Pro Phe Gly Asp Ser Tyr Ile Val Val Gly Arg Gly Thr Thr Gln Ile
                85                  90                  95
```

-continued

```
Asn Tyr His Trp His Lys Glu
            100


<210> SEQ ID NO 13
<211> LENGTH: 100
<212> TYPE: PRT
<213> ORGANISM: Flavivirus sp.

<400> SEQUENCE: 13

Lys Gly Thr Ser Tyr Lys Met Cys Thr Asp Lys Met Ser Phe Val Lys
  1               5                  10                  15

Asn Pro Thr Asp Thr Gly His Gly Thr Ala Val Met Gln Val Lys Val
            20                  25                  30

Pro Lys Gly Ala Pro Cys Arg Ile Pro Val Met Val Ala Asp Asp Leu
        35                  40                  45

Thr Ala Ser Val Asn Lys Gly Ile Leu Val Thr Val Asn Pro Ile Ala
     50                  55                  60

Ser Thr Asn Glu Asp Glu Val Leu Ile Glu Val Asn Pro Pro Phe Gly
 65                  70                  75                  80

Asp Ser Tyr Ile Ile Val Gly Thr Gly Asp Ser Arg Leu Thr Tyr Gln
                 85                  90                  95

Trp His Lys Glu
            100


<210> SEQ ID NO 14
<211> LENGTH: 96
<212> TYPE: PRT
<213> ORGANISM: Flavivirus sp.

<400> SEQUENCE: 14

Lys Gly Leu Thr Tyr Thr Met Cys Asp Lys Thr Lys Phe Thr Trp Lys
  1               5                  10                  15

Arg Ala Pro Thr Asp Ser Gly His Asp Thr Val Val Met Glu Val Thr
            20                  25                  30

Phe Ser Gly Thr Lys Pro Cys Arg Ile Pro Val Arg Ala Val Ala His
        35                  40                  45

Gly Ser Pro Asp Val Asn Val Ala Met Leu Ile Thr Pro Asn Pro Thr
     50                  55                  60

Ile Glu Asn Asn Gly Gly Gly Phe Ile Glu Met Gln Leu Pro Pro Gly
 65                  70                  75                  80

Asp Asn Ile Ile Tyr Val Gly Glu Leu Ser Tyr Gln Trp Phe Gln Lys
                 85                  90                  95


<210> SEQ ID NO 15
<211> LENGTH: 96
<212> TYPE: PRT
<213> ORGANISM: Flavivirus sp.

<400> SEQUENCE: 15

Lys Gly Met Thr Tyr Thr Val Cys Glu Gly Ser Lys Phe Ala Trp Lys
  1               5                  10                  15

Arg Pro Pro Thr Asp Ser Gly His Asp Thr Val Val Met Glu Val Thr
            20                  25                  30

Tyr Thr Gly Ser Lys Pro Cys Arg Ile Pro Val Arg Ala Val Ala His
        35                  40                  45

Gly Glu Pro Asn Val Asn Val Ala Ser Leu Ile Thr Pro Asn Pro Ser
     50                  55                  60

Met Glu Asn Thr Gly Gly Gly Phe Val Glu Leu Gln Leu Pro Pro Gly
```

```
 65                  70                  75                  80

Asp Asn Ile Ile Tyr Val Gly Glu Leu Ser His Gln Trp Phe Gln Lys
                 85                  90                  95


<210> SEQ ID NO 16
<211> LENGTH: 96
<212> TYPE: PRT
<213> ORGANISM: Flavivirus sp.

<400> SEQUENCE: 16

Lys Gly Leu Thr Tyr Thr Met Cys Asp Lys Thr Lys Phe Thr Trp Lys
  1               5                  10                  15

Arg Ala Pro Thr Asp Ser Gly His Asp Thr Val Val Met Glu Val Thr
             20                  25                  30

Phe Ser Gly Thr Lys Pro Cys Arg Ile Pro Val Arg Ala Val Ala His
         35                  40                  45

Gly Ser Pro Asp Val Asn Val Ala Met Leu Ile Thr Pro Asn Pro Thr
     50                  55                  60

Ile Glu Asn Asn Gly Gly Gly Phe Ile Glu Met Gln Leu Pro Pro Gly
 65                  70                  75                  80

Asp Asn Ile Ile Tyr Val Gly Glu Leu Ser His Gln Trp Phe Gln Lys
                 85                  90                  95


<210> SEQ ID NO 17
<211> LENGTH: 96
<212> TYPE: PRT
<213> ORGANISM: Flavivirus sp.

<400> SEQUENCE: 17

Lys Gly Leu Thr Tyr Thr Met Cys Asp Lys Ser Lys Phe Ala Trp Lys
  1               5                  10                  15

Arg Thr Pro Thr Asp Ser Gly His Asp Thr Val Val Met Glu Val Thr
             20                  25                  30

Phe Ser Gly Ser Lys Pro Cys Arg Ile Pro Val Arg Ala Val Ala His
         35                  40                  45

Gly Ser Pro Asp Val Asn Val Ala Met Leu Ile Thr Pro Asn Pro Thr
     50                  55                  60

Ile Glu Asn Asp Gly Gly Gly Phe Ile Glu Met Gln Leu Pro Pro Gly
 65                  70                  75                  80

Asp Asn Ile Ile Tyr Val Gly Glu Leu Ser His Gln Trp Phe Gln Thr
                 85                  90                  95


<210> SEQ ID NO 18
<211> LENGTH: 96
<212> TYPE: PRT
<213> ORGANISM: Flavivirus sp.

<400> SEQUENCE: 18

Lys Gly Leu Thr Tyr Thr Val Cys Asp Lys Thr Lys Phe Thr Trp Lys
  1               5                  10                  15

Arg Ala Pro Thr Asp Ser Gly His Asp Thr Val Val Met Glu Val Gly
             20                  25                  30

Phe Ser Gly Thr Arg Pro Cys Arg Ile Pro Val Arg Ala Val Ala His
         35                  40                  45

Gly Val Pro Glu Val Asn Val Ala Met Leu Ile Thr Pro Asn Pro Thr
     50                  55                  60

Met Glu Asn Asn Gly Gly Gly Phe Ile Glu Met Gln Leu Pro Pro Gly
 65                  70                  75                  80
```

-continued

Asp Asn Ile Ile Tyr Val Gly Asp Leu Asn Tyr Gln Trp Phe Gln Lys
85 90 95

<210> SEQ ID NO 19
<211> LENGTH: 96
<212> TYPE: PRT
<213> ORGANISM: Flavivirus sp.

<400> SEQUENCE: 19

Lys Gly Leu Thr Tyr Thr Met Cys Asp Lys Ala Lys Phe Thr Trp Lys
1 5 10 15

Arg Ala Pro Thr Asp Ser Gly His Asp Thr Val Val Met Glu Val Ala
20 25 30

Phe Ser Gly Thr Lys Pro Cys Arg Ile Pro Val Arg Ala Val Ala His
35 40 45

Gly Ser Pro Asp Val Asp Val Ala Met Leu Ile Thr Pro Asn Pro Thr
50 55 60

Ile Glu Asn Asn Gly Gly Gly Phe Ile Glu Met Gln Leu Pro Pro Gly
65 70 75 80

Asp Asn Ile Ile Tyr Val Gly Glu Leu Lys His Gln Trp Phe Gln Lys
85 90 95

<210> SEQ ID NO 20
<211> LENGTH: 97
<212> TYPE: PRT
<213> ORGANISM: Flavivirus sp.

<400> SEQUENCE: 20

Lys Gly Thr Thr Tyr Ser Met Cys Asp Lys Ala Lys Phe Lys Trp Lys
1 5 10 15

Arg Val Pro Val Asp Ser Gly His Asp Thr Val Val Met Glu Val Ser
20 25 30

Tyr Thr Gly Ser Asp Lys Pro Cys Arg Ile Pro Val Arg Ala Val Ala
35 40 45

His Gly Val Pro Ala Val Asn Val Ala Met Leu Ile Thr Pro Asn Pro
50 55 60

Thr Ile Glu Thr Asn Gly Gly Gly Phe Ile Glu Met Gln Leu Pro Pro
65 70 75 80

Gly Asp Asn Ile Ile Tyr Val Gly Asp Leu Ser Gln Gln Trp Phe Gln
85 90 95

Lys

<210> SEQ ID NO 21
<211> LENGTH: 111
<212> TYPE: PRT
<213> ORGANISM: West Nile virus

<400> SEQUENCE: 21

Gln Leu Lys Gly Thr Thr Tyr Gly Val Cys Ser Lys Ala Phe Lys Phe
1 5 10 15

Leu Gly Thr Pro Ala Asp Thr Gly His Gly Thr Val Val Leu Glu Leu
20 25 30

Gln Tyr Thr Gly Thr Asp Gly Pro Cys Lys Val Pro Ile Ser Ser Val
35 40 45

Ala Ser Leu Asn Asp Leu Thr Pro Val Gly Arg Leu Val Thr Val Asn
50 55 60

Pro Phe Val Ser Val Ala Thr Ala Asn Ala Lys Val Leu Ile Glu Leu

-continued

```
 65                  70                  75                  80

Glu Pro Pro Phe Gly Asp Ser Tyr Ile Val Val Gly Arg Gly Glu Gln
                 85                  90                  95

Gln Ile Asn His His Trp His Lys Ser Gly Ser Ser Ile Gly Lys
            100                 105                 110


<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 22

tgcatcaagc tttggctgga                                                20


<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 23

tcttgccggc tgatgtctat                                                20


<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 24

tgcaccaagc tctggccgga                                                20


<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 25

cggagctctt gcctgccaat                                                20


<210> SEQ ID NO 26
<211> LENGTH: 96
<212> TYPE: PRT
<213> ORGANISM: Flavivirus sp

<400> SEQUENCE: 26

Lys Gly Leu Thr Tyr Thr Met Cys Asp Lys Thr Lys Phe Thr Trp Lys
  1               5                  10                  15

Arg Ala Pro Thr Asp Ser Gly His Asp Thr Val Val Met Glu Val Thr
             20                  25                  30

Phe Ser Gly Thr Lys Pro Cys Arg Ile Pro Val Arg Ala Val Ala His
         35                  40                  45

Gly Ser Pro Asp Val Asn Val Ala Met Leu Ile Thr Pro Asn Pro Thr
     50                  55                  60
```

-continued

```
Ile Glu Asn Asn Gly Gly Gly Phe Ile Glu Met Gln Leu Pro Pro Gly
 65                 70                  75                  80

Asp Asn Ile Ile Tyr Val Gly Glu Leu Ser Tyr Gln Trp Phe Gln Lys
                85                  90                  95


<210> SEQ ID NO 27
<211> LENGTH: 96
<212> TYPE: PRT
<213> ORGANISM: Flavivirus sp

<400> SEQUENCE: 27

Lys Gly Leu Thr Tyr Thr Met Cys Asp Lys Thr Lys Phe Thr Trp Lys
  1               5                  10                  15

Arg Ala Pro Thr Asp Ser Gly His Asp Thr Val Val Met Glu Val Thr
            20                  25                  30

Phe Ser Gly Thr Lys Pro Cys Arg Ile Pro Val Arg Ala Val Ala Gly
        35                  40                  45

His Ser Pro Asp Val Asn Val Ala Met Leu Ile Thr Pro Asn Pro Thr
     50                  55                  60

Ile Glu Asn Asn Gly Gly Gly Phe Ile Glu Met Gln Leu Pro Pro Gly
 65                 70                  75                  80

Asp Asn Ile Ile Tyr Val Gly Glu Leu Ser His Gln Trp Phe Gln Lys
                85                  90                  95
```

COMPOSITIONS AND METHODS RELATED TO FLAVIVIRUS ENVELOPE PROTEIN DOMAIN III ANTIGENS

This application is a national phase application under 35 U.S.C. §371 of International Application No. PCT/US2003/25681 filed 18 Aug. 2003, which claims priority to U.S. Provisional Patent Applications Ser. No. 60/403,893 filed on Aug. 16, 2002 and 60/445,581 filed Feb. 6, 2003, each of which is incorporated in its entirety herein by reference.

The government may own rights in the present invention pursuant to contract number U90/CCU618754-01 from U.S. Department of Health and Human Services Centers for Disease Control.

BACKGROUND OF THE INVENTION

1. Field of the Invention

The present invention relates generally to the fields of virology, immunology and diagnostics. More particularly, it concerns antibodies directed to and antigens derived from *flavivirus* envelope protein domain III in compositions and methods for detection of various members of the genus *flavivirus*.

2. Description of Related Art

West Nile virus (WN) is a member of the Japanese encephalitis (JE) serocomplex of the genus *Flavivirus* (Family Flaviviridae). This virus was first isolated from a febrile woman in the West Nile province of Uganda in 1937, and now has an almost worldwide distribution including parts of Africa, Asia, Europe and, most recently, North America. Kunjin virus, now re-classified as a subtype of West Nile virus, is found in Australasia.

Since 1999, the United States has experienced annual epidemics of WN disease in humans and animals over an expanding geographical range. WN virus has been isolated in 44 states, and more than 4,100 cases of human disease resulting in 284 deaths had been reported during 2002 (MMWR, 2002a). Several of these cases are suspected to have originated from virus transmitted during blood transfusion and/or organ transplantation (MMWR, 2002b). Outbreaks of WN disease with neurological manifestations have also been reported in Eastern Europe, North Africa and Israel since the mid-1990s (reviewed by Murgue et al., 2002).

Other members of the JE serocomplex include JE virus, found throughout Asia, St. Louis encephalitis (SLE) virus, found in the Americas, and Murray Valley encephalitis (MVE) virus, found in Australia and New Guinea. These viruses are antigenically similar to WN virus, and their co-circulation in several regions of the world has complicated the specific diagnosis of infections by these viruses in humans and other hosts (Fonseca et al., 1991; Martin et al., 2002). Current protocols for the serological diagnosis of WN virus infection in the United States rely primarily on preliminary screening for WN virus-reactive IgM/IgG antibody by capture ELISA and confirmation by plaque reduction neutralization test (PRNT) (CDC, 2001), a process which results in considerable delays in the reliable reporting of accurate case numbers, and requires the confirmatory testing to be performed in specialized laboratories.

Current diagnostic assays utilize either ELISA or dipstick formats for identification of *flavivirus* infection (PanBio, Integrated Diagnostics (Dobler et al., 1996, Niedrig et al., 2001, Yoshii et al., 2003)). A number of assays are available for the detection of dengue virus infection. These assays utilize antigen capture and antibody-based ELISAs and dipsticks for detection of virus specific IgG or IgM. Diagnosis of TBE infection depends on IgG-based ELISA assays that are available in Europe (Dobler et al., 1996, Niedrig et al., 2001, Yoshii et al., 2003). However, these tests have limitations with both sensitivity and cross-reactivity with other *flaviviruses* (Niedrig et al., 2001).

The recent utilization of subviral particles (SVP) in an ELISA-based diagnostic test for tick borne encephalitis TBE infection shows promise (Yoshii et al., 2003). Since this assay uses intact viral M and E proteins it is likely that the pitfalls that affect the use of complete viral antigen (e.g., cross-reactivity) may impede the employment of this assay in diagnostic settings.

The use of RT-PCR is also a potential method for diagnosis of *flavivirus* infection. However, RT-PCR assays have the significant limitation of requiring advanced techniques, equipment and reagents that require a cold-chain for stability. In addition, RT-PCR detects the presence of virus in patient serum, a condition that is not usually met when patients came to a hospital as the virus is frequently cleared from the bloodstream by the onset of symptoms. Clearly, there is a need to improve the current reagents used for diagnosis of West Nile and TBE virus infections.

SUMMARY OF THE INVENTION

Embodiments of the invention include the use of recombinant envelope protein domain III (rDIII or rD3) derived from West Nile virus (WN), tick borne encephalitis serocomplex viruses (TBE), and/or other *flaviviruses* as a reagent(s) to detect the presence of anti-WN or anti-TBE antibodies in a subject, e.g., naturally infected primates, including humans. Certain embodiments include polypeptides derived from WN rDIII that are sensitive and very specific for WN virus infection and can also differentiate between closely related mosquito-borne *flaviviruses*. Some embodiments of the invention include the use of poly-peptides derived form TBE rDIII (rD3) as a diagnostic antigen to the TBE serocomplex of *flaviviruses*. While differentiation between the very similar TBE viruses could not be achieved, some of the polypeptide reagents were highly specific for the tick-borne *flaviviruses* and were much more specific than mouse brain-derived viral antigen in differentiating *flavivirus* positive sera in the ELISA format.

The development of a specific and sensitive diagnostic assay for detection of *flavivirus* infection will greatly enhance the ability to identify, track, and treat diseases caused by these viruses. The present invention takes advantage of the observation that a *flavivirus* envelope protein domain III (DIII) antigen can be used to specifically detect serocomplexes of *flavivirus* and antibodies against certain serocomplexes or certain *flaviviruses*, e.g., West Nile virus. In addition, the present invention takes advantage of the observation that certain West Nile virus envelope protein domain III (WN-DIII) antigens can be used to specifically detect West Nile virus and antibodies against West Nile virus. Various embodiments of the invention are directed to compositions and methods related to detecting West Nile virus or TBE serocomplex viruses or antibodies in a subject, patient, animal, biological or other type of sample.

The present invention includes compositions and methods for the detection or diagnosis of *flavivirus*, TBE viruses or West Nile virus. Recombinant West Nile virus envelope protein domain III (WN-rDIII) or a recombinant TBE serocomplex virus envelope protein domain III (TBE-rDIII) can be expressed in *E. coli* as a fusion protein to produce a soluble protein that can be purified. Rabbit antisera raised against WN-rDIII or TBE-rDIII shows virus or serocomplex specificity, respectively, in physical and biological assays. Removal of a non-Viral fusion component typically improves the specificity and signal intensity for WN-rDIII or TBE-rDIII.

In certain embodiments of the invention, methods for screening for a *flavivirus* in a subject include a) contacting a sample from the subject with a composition comprising a *flavivirus* envelope protein domain III polypeptide under conditions that permit formation of specific immunocomplex between any antibody in the sample and the envelope protein domain III polypeptide; and b) detecting whether a specific immunocomplex is formed. An envelope protein domain III polypeptide refers to a polypeptide including the amino acids that define domain III, a structural element of the *flavivirus* envelope protein, for example amino acid sequences 292 to 402 of SEQ ID NO:3, amino acid sequences set forth in SEQ ID NO:4-21 or homologous sequences from other *flaviviruses*. Homologous envelope protein domain III sequences from other *flavivirus* typically have an identity of at least 70, 75, 80, 85, 90, 95 percent or greater to the amino acid sequence 292-402 set forth in SEQ ID NO: 3 or the amino acid sequences set forth in SEQ ID NO:4-21. Additionally, a specific immunocomplex refers to a complex between a polypeptide containing an epitope recognized by an antibody and the antibody that recognizes the epitope where the complex can be detected and distinguish above any non-specific or background interactions. The envelope protein domain III polypeptide may be a dengue virus envelope protein domain III polypeptide, yellow fever virus envelope protein domain III polypeptide, West Nile virus envelope protein domain III polypeptide, St. Louis encephalitis virus envelope protein domain III polypeptide, Murray valley encephalitis virus envelope protein domain III polypeptide, a Central European encephalitis (CEE) virus envelope protein domain III polypeptide, a Russian spring-summer encephalitis (RSSE) virus envelope protein domain III polypeptide, a Langat (LGT) virus envelope protein domain III polypeptide, a Powassan virus (POW) envelope protein domain III polypeptide, an Alkhurma (ALK) envelope protein domain III polypeptide, a Kyasanur Forest disease (KFD) virus envelope protein domain III polypeptide, an Omsk hemorrhagic fever (OHF) virus envelope protein domain III polypeptide or a combination or variant thereof. In particular embodiments, the envelope protein domain III polypeptide is a West Nile virus envelope protein domain III polypeptide or a variant thereof. In other embodiments, the envelope protein domain III polypeptide is derived from a CEE or a RSSE envelope protein domain III polypeptide or a variant thereof. The envelope protein domain III polypeptide may include 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 91, 92, 93, 94, 95, 96, 97, 98, 99, 100, 101, 102, 103, 104, 105, 106, 107, 108, 109, or 110 contiguous amino acids of a *flavivirus* envelope protein domain III polypeptide or a variant thereof. It is contemplated that 1, 2, 3, 4, 5, 6, 7, 8, 9, 10, 11, 12, 13, 14, 15 or more carboxy and/or amino terminal amino acids flanking the envelope protein domain III may also be included in arm envelope protein domain III polypeptide. In certain embodiments, an amino acid sequence that is about or at least 50%, 55%, 65%, 70%, 75%, 80%, 85%, 90%, 95%, 99%, or any value therebetween, identical to amino acid 292-402 of SEQ ID NO:3 and/or SEQ ID NO:8-21 is contemplated. A domain III polypeptide may include the amino acids 292-402 as set forth in SEQ ID NO:3, the amino acids 1-111 as set forth in SEQ ID NO:21, the amino acids as set forth in SEQ ID NO:4-20, or variants thereof. Some embodiments of the invention further comprise at least a second envelope protein domain III polypeptide. A second envelope protein domain III polypeptide may be selected from SEQ ID NO:3-21 or a similar sequence from other *flaviviruses* or closely related viruses. The envelope protein domain III polypeptide may be prepared by isolating a recombinant or non-recombinant envelope protein domain III polypeptide. The envelope protein domain III polypeptide may be denatured or non-denatured. In particular embodiments the envelope protein domain III polypeptide is prepared by isolating a recombinant envelope protein domain III polypeptide fusion protein. In certain embodiments, a recombinant envelope protein domain III polypeptide may be cleaved by an appropriate protease to separate the envelope protein domain III polypeptide from its viral or non-viral fusion partner (e.g., GST, his-tag or MBP). A envelope protein domain III polypeptide may be obtained from bacteria comprising an expression vector encoding the envelope protein domain III polypeptide or envelope protein domain III polypeptide fusion protein. The envelope protein domain III polypeptide or fusion protein may be obtained from a mammalian or insect cell comprising an expression vector encoding the envelope protein domain III polypeptide or fusion protein.

In certain embodiments it is contemplated an envelope protein domain III polypeptide may be used in conjunction with 1, 2, 3, 4, 5, 6, or more additional antigens derived the same or other members of the *flavivirus* genus family. These polypeptides may be used in a variety of formats including, but not limited to ELISA and peptide array formats.

In various embodiments, samples may be derived from a variety of subjects infected with or suspected to be infected with a *flavivirus*, including WN or a TBE serocomplex virus. The subjects include, but are not limited to an animal, a bird, a human, a mosquito, a tick or other host organism for a *flavivirus*.

The step of determining whether an immunocomplex is formed may be accomplished by a number of ways well known to those of ordinary skill in the art. The immunocomplex may be detected by ELISA, Western blotting, dipstick or peptide array. In other embodiments, an immunocomplex is detected using anti-antibody secondary reagents. Anti-antibody secondary reagents refer to agents that specifically bind or detect an antibody. Compounds of the invention may be labeled with a detecting agent, which may be colorimetric, enzymatic, radioactive, chromatographic or fluorescent. The antigen may be affixed to a solid non-reactive support, which refers to a compound that will not react with antigens of the invention or antibodies in any sample. The support may be a plate or assay dish, and be made of any non-reactive material, including, glass, plastic, silicon or the like. An antibody may include, but is not limited to an IgA, an IgG or an IgM antibody.

Various embodiments include methods of identifying a *flavivirus* in a subject comprising a) contacting a sample from the subject with a composition comprising at least one *flavivirus* envelope protein domain III polypeptide under conditions that permit formation of specific immunocomplex between any antibody in the sample and the envelope protein domain III polypeptide; and b) detecting whether a specific immunocomplex is formed.

Certain embodiments of the invention include compositions for testing a sample for *flavivirus* or antibodies to *flavivirus* comprising an isolated *flavivirus* envelope protein domain III polypeptide. In particular embodiments, the *flavivirus* envelope protein domain III polypeptide is a West Nile virus or a TBE serocomplex virus envelope protein domain III polypeptide or variants thereof. A West Nile virus envelope protein domain III polypeptide may be derived from West Nile strains 382-99, EthAn4766, 385-99, Kunjin MRM16, Golblum, TL44, DakAnMg, 804994 or a variant thereof, which may be obtained through the World Arbovirus Reference Collection at the University of Texas Medical Branch at Galveston or similar depositories such as the American Type Culture Collection. A TBE serocomplex virus may include a Central European encephalitis (CEE) virus, a Russian spring-summer encephalitis (RSSE) virus, a Langat (LGT) virus, a Powassan virus (POW), an Alkhurma (ALK), a Kyasanur Forest disease (KFD) virus, or an Omsk hemorrhagic fever (OHF) virus, which may be obtained through the World Arbovirus Reference Collection at the University of Texas Medical Branch at Galveston or similar depositories such as the American Type Culture Collection. The composition may include a *flavivirus* envelope protein domain III polypeptide, which may comprise 10, 11, 12, 13, 14, 15, 16, 17, 18, 19, 20, 25, 30, 35, 40, 45, 50, 55, 60, 65, 70, 75, 80, 85, 90, 95, 100, 110, or more, as well as values there between, of consecutive amino acids of the envelope protein domain III polypeptide or variants thereof. In particular embodiments, the composition may comprise the amino acid sequence as set forth in, or is about or at least 50%, 55%, 65%, 70%, 75%, 80%, 85%, 90%, 95%, 99%, or any value therebetween, identical to, one or more of SEQ ID NO:3-21. The envelope protein domain III polypeptide may be operatively linked to a substrate such as a plate, a microtiter plate, a bead, or a microarray.

Embodiments of the invention also include compositions for testing a sample for West Nile virus or a TBE serocomplex virus comprising an isolated *flavivirus* or *flavivirus* envelope protein domain III polypeptide as described above and incorporated here by reference.

Embodiments of the invention also include kits comprising any of the components of the invention described above, in a suitable container means. Kits may include one or more *flavivirus*, TBE serocomplex virus or West Nile virus envelope protein domain III antigens. In still further embodiments, antigens are from the same or different strains. Such antigens may be in the same or in separate compositions. Kits may further include non-reactive supports in which antigens of the invention are affixed or attached. Kits may also include secondary antibody reagents and/or other detection reagents. Antigens or antibodies in the kits may be labeled. Labels may be colorimetric, enzymatic, radioactive, or fluorescent. The envelope protein domain III polypeptide may be a dengue fever virus envelope protein domain III polypeptide, yellow fever virus envelope protein domain III polypeptide, West Nile virus envelope protein domain III polypeptide, St. Louis encephalitis virus envelope protein domain III polypeptide, Murray Valley encephalitis virus envelope protein domain III polypeptide, a Central European encephalitis (CEE) virus envelope protein domain III polypeptide, a Russian spring-summer encephalitis (RSSE) virus envelope protein domain III polypeptide, a Langat (LGT) virus envelope protein domain III polypeptide, a Powassan virus (POW) envelope protein domain III polypeptide, an Alkhurma (ALK) envelope protein domain III polypeptide, a Kyasanur Forest disease (KFD) virus envelope protein domain III polypeptide, an Omsk hemorrhagic fever (OHF) virus envelope protein domain III polypeptide or a combination thereof. In particular embodiments, the envelope protein domain III polypeptide is a West Nile virus envelope protein domain III polypeptide. A kit may include compositions for screening for West Nile or TBE serocomplex virus antibodies in a subject comprising: a) an assay plate comprising a multiplicity of microtiter wells comprising a composition comprising at least one envelope protein domain III polypeptide capable of binding a *flavivirus* antibody in the sample that can specifically bind to at least one envelope protein domain III polypeptide; and b) a container means comprising a labeled secondary antibody having specific binding affinity for a *flavivirus* antibody in the sample that can specifically bind to at least one envelope protein domain III polypeptide.

Embodiments of the invention also include methods of screening for *flavivirus* in a subject comprising: a) contacting a sample from the subject with a composition from the kit under binding conditions; and, b) detecting whether a specific immunocomplex is formed between an antibody and the at least one envelope protein domain III polypeptide.

Various embodiments of the invention include vaccine compositions comprising a *flavivirus*, TBE serocomplex or West Nile envelope protein domain III polypeptide as described herein. The vaccine composition may further comprise an adjuvant(s) and an excipient(s) known in the art.

Other embodiments of the invention include an antibody or antibodies that selectively bind to an epitope in a envelope protein domain III of a *flavivirus*, TBE serocomplex or West Nile virus envelope protein. The epitope may be present in a West Nile or a TBE serocomplex envelope protein domain III polypeptide or a variant thereof.

It is contemplated that any embodiment of a method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 illustrates an exemplary amino acid alignment of envelope protein domain IIIs from various *flaviviruses*.

FIG. 5 illustrates the results of an exemplary PRNT assay showing the neutralization activity of rabbit anti-envelope protein domain III sera.

FIG. 6 illustrates an envelope protein domain III amino acid sequence variations for ten West Nile virus strains, and representative JE (Genbank accession U21057), SLE (Genbank accession M16614) and MVE (Genbank accession M24220) viruses. Dots (.) indicate conservation with the West Nile virus strain 385-99 sequence. Residues associated with escape from neutralization by Mabs or anti-envelope protein domain III serum for WN virus strains are shaded.

FIG. 16 illustrates an exemplary amino acid alignment of envelope protein domain IIIs from various *flaviviruses.*

DESCRIPTION OF ILLUSTRATIVE EMBODIMENTS

Figure 2:
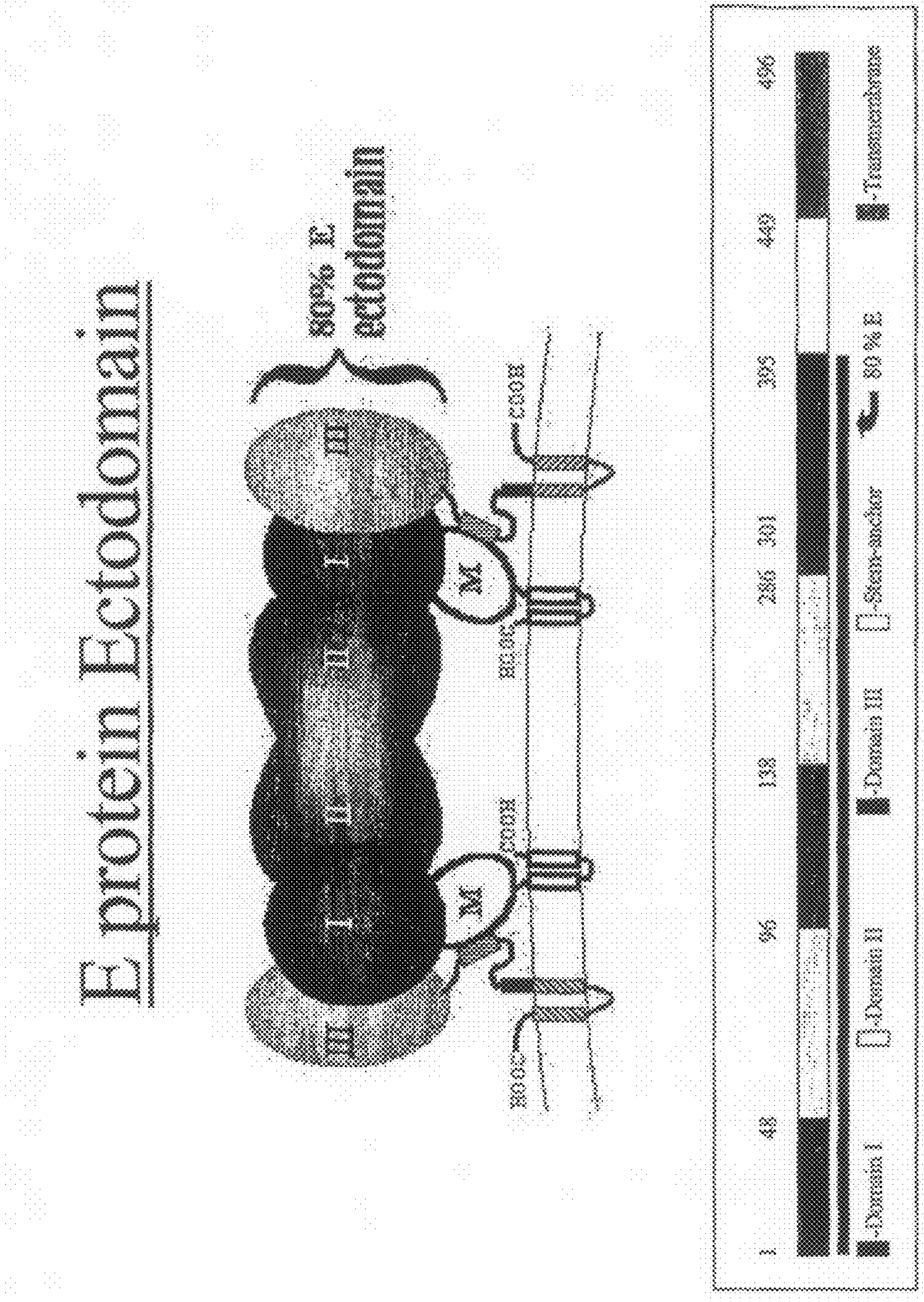
FIG. 2 illustrates a two-dimensional schematic of the topology and structure of a *flavivirus* envelope protein.

Various embodiments of the invention include compositions and methods related to *flavivirus*, TBE serocomplex *flaviviruses* (viruses) (TBE) or West Nile virus (WN) envelope protein domain III (DIII or D3) or recombinant DIII (rDIII or rD3) as an antigen for specific diagnosis or detection of *flavivirus*, TBE serocomplex viruses and/or WN virus. The *flavivirus* envelope protein (E) is the major virion surface protein. It plays an important role in virus attachment and entry into host cells, and is also an important target for virus neutralizing antibodies (Sanchez and Ruiz, 1996; Mandl et al., 2000; Crill and Roehrig, 2001). The inventors describe the identification of residues associated with the neutralization of lineage I WN virus strain 385-99 (isolated in New York City in 1999) by monoclonal antibodies (MAbs) that bound to DIII, the putative receptor-binding domain, of the envelope protein.

Using these DIII-reactive MAbs and a polyclonal serum generated against a recombinant, bacterially-expressed WN virus rDIII fragment, the antigenic relationships between WN virus strains representative of genetic lineages I and II have been investigated and envelope protein domain III residues that constitute subtype specific epitopes have been indentified.

The present invention includes compositions and methods for the detection or diagnosis of a *flavivirus*, including compositions and methods for distinguishing between different *flaviviruses* or groups of *flaviviruses*. In particular embodiments, the *flavivirus* being detected is the West Nile virus or a TBE serocomplex virus. Recombinant *flavivirus*, TBE virus or West Nile virus envelope protein domain III (rDIII) can be expressed in *E. coli* as a fusion protein to produce a soluble protein that can easily be purified. Rabbit antisera raised against a rDIII (rDIII) shows virus specificity in physical and biological assays. Removal of the fusion component improves specificity and signal intensity for a particular rDIII.

The serological diagnosis of infection by *flaviviruses* can be complicated by the presence of *flavivirus* cross-reactive antibodies that produce false-positive results for *flavivirus* infections, especially in regions where more than one virus is endemic. Current diagnostic reagents for tick-borne *flavivirus* infection have been found to cross-react with yellow fever or dengue positive sera. In certain embodiments, recombinant *flavivirus* envelope protein domain III (rDIII or rD3) can be used as a diagnostic reagent to differentiate between infection by mosquito- and tick-borne *flaviviruses*. Embodiments of the invention also include the use of rDIII in an ELISA-based format for differentiation between serum specific for either mosquito- or tick-borne *flaviviruses*, which may or may not differentiate among the members of the tick-borne encephalitis (TBE) serocomplex of *flaviviruses*. Sera derived against several TBE serocomplex rDIII were found to cross-react with heterologous rDIII within the TBE serocomplex, but not with those from mosquito-borne *flaviviruses*, in both Western blots and ELISAs. Mouse hyperimmune serum generated against TBE serocomplex viruses was also found to react specifically with TBE serocomplex rDIII, but not with rDIII from mosquito-borne viruses and vice versa. A similar test using virus-derived antigen was performed and a loss of both specificity and sensitivity was observed. These results indicate that *flavivirus* rDIII would be a useful reagent for the detection of infection by TBE serocomplex *flaviviruses*, several of which are potential biothreat agents, but may not provide the ability to differentiate between infections by separate members of the serocomplex.

I. *Flavivirus*

West Nile virus and TBE viruses are members of the genus *Flavivirus*. The genus *Flavivirus* is a genera of the Flaviviridae family and includes the viral groups of Yellow Fever virus group, Tick-borne encephalitis virus group, Rio Bravo Group, Japanese encephalitis Group, Tyuleniy Group, Ntaya Group, Uganda S Group, Dengue Group, and Modoc Group. Members of the *Flavivirus* genus may produce a wide variety of disease states, such as fever, arthralgia, rash, hemorrhagic fever, and/or encephalitis. The outcome of infection is influenced by both the virus and host-specific factors, such as age, sex, genetic susceptibility, and/or pre-exposure to the same or a related agent. Some of the various diseases associated with members of the genus *Flavivirus* are yellow fever; dengue fever; and West Nile, Japanese, and St. Louis encephalitis. For a review of *flaviviruses* see Burke and Monath (2001), which is incorporated herein by reference.

Virions of the Flaviviridae generally contain one molecule of a linear positive-sense single stranded RNA genome of approximately 10,000-11,000 nucleotides that replicates in the cytoplasm of an infected cell. Typically the 5' end of the genome has a cap and the 3' end that may or may not have a poly (A) tract. Many members of the genus *Flavivirus* are transmitted by a vector such as an insect, in many cases the insect is a mosquito.

The viral genome of the *Flavivirus* genus is translated as a single polyprotein and is subsequently cleaved into mature proteins. The proteins encoded by the Virus typically consist of structural and non-structural proteins. Generally, there are three structural proteins that typically include the envelope protein (E protein) (amino acids 275-787 of GenBank accession number NP_041724, incorporated herein by reference and SEQ ID NO:2), the core or capsid protein (C)(amino acids 1-92 of GenBank accession number NP_04-1724), and the pre-membrane protein (preM) (amino acids 105-223 of GenBank accession number NP_041724) (Yamshchikov et al., 2001, incorporated herein by reference). The envelope protein is approximately 496 amino acids with an approximate molecular weight of 50 kDa and is often glycosylated. The envelope protein typically contains twelve conserved cysteine residues which form six disulfide bridges. The core protein is approximately 13 kDa, and is rich in arginine and lysine residues. The pre-membrane protein is approximately 10 kDa and is cleaved during or after release of the virus from infected cells. A cleavage product of the prM protein remains associated with the virion and is approximately 8 kDa and is termed the membrane protein (M). Typically, it is the carboxy terminus of prM that remains associated with the virus particle as the M protein.

The *flavivirus* E protein is a dimer positioned parallel to virus surface. The ectodomain includes three domains I—Central domain (EI), II—Dimerization domain (EII), III—Immunogenic/Receptor binding domain (DIII) (FIG. 2). The amino acid sequence of an exemplary West Nile virus E protein Envelope protein domain III is set forth in SEQ ID NO:3. An amino acid alignment of various *flavivirus* DIIIs is presented in FIG. 1. The E protein envelope protein domain III is approximately 10.5 kDa with a single disulfide bridge. The E protein envelope protein domain III has an Ig-like fold, which is a β-barrel "type" configuration with no α-helices. Some *flavivirus* E protein domain IIIs contain a RGD integrin-binding motif.

Serological comparisons of West Nile virus strains have distinguished four major antigenic subtypes: a group of strains from Africa; strains from Europe and some Asian strains; strains from India; and strains of Kunjin virus from Australasia (Doherty et al., 1968; Hammam et al., 1966; Blackburn et al., 1987; Calisher et al., 1989; Morvan et al., 1990). Subsequently, analyses of nucleotide sequences identified two major genetic lineages, designated I and II, which included some subtypes and which correlated well with the antigenic groupings. Genetic lineage I included European and some African strains, Kunjin virus strains, and Indian strains; lineage II comprised only African strains (Lanctiotti et al., 1999; Jia et al., 1999; Scherret et al., 2001).

The TBE virus group that is associated with human disease is distinct genetically and antigenically from the mosquito-borne viruses and are hence referred to as the TBE serocomplex. In addition to viruses that cause TBE, there are several other viruses within this serocomplex. Among these are the Langat (LGT) virus that is not known to infect humans in a natural environment, louping ill (LI) virus that causes encephaltitic disease normally in sheep, Powassan virus (POW) that also causes encephalitis, and the hemorrhagic fever associated viruses Alkhurma (ALK), Kyasanur Forest disease (KFD) and Omsk hemorrhagic fever (OHF) (Burke and Monath, 2001). Tick-borne encephalitis (TBE) is a disease endemic to vast areas from western Europe across Asia and into Japan and China. This disease is characterized by rapid onset of fever with subsequent development of potentially fatal encephalitis (Gritsun et al., 2003). TBE found in Europe is typically less severe than that found in central and eastern Asia and the viruses that cause the different forms of the disease can be distinguished genetically and also by their tick vectors. Three subtypes of TBE have been described based on both serology and genetic data: central European encephalitis (CEE) (or western subtype), Siberian subtype TBE and Far-eastern subtype TBE (Heinz et al., 2000). The disease caused by the latter two subtypes are often commonly referred to as Russian spring-summer encephalitis (RSSE). In addition, OHF, KFD and RSSE viruses are listed as potential biothreat agents by the National Institutes for Health and Centers for Disease Control. The possible introduction of these viruses by natural or artificial means into non-endemic areas, as well as the present extensive endemic regions, make the diagnosis of infection by these viruses a major public health objective. The lack of simple and accurate diagnostic assays makes the development of a TBE serocomplex diagnostic kit very important to rapid recognition of the causative agent of disease.

Various members of the Flaviviridae family are available through the American Type Culture Collection (Manassas Va.) under the following ATCC numbers: Dengue type 1 (VR-71), Ilheus (VR-73), Japanese encephalitis (VR-74), Murray Valley encephalitis (VR-77), Ntaya (VR 78), St. Louis encephalitis (VR-80), Uganda S (VR-81), West Nile (VR-82), Zika (VR-84), Dengue type 4 (VR-217), Dengue type 2 (VR-222), Japanese encephalitis (VR-343), Dengue type 1 (VR-344), Dengue type 2 (VR-345), Edge hill (VR-377), Entebbe bat (VR-378), Kokobera (VR-379), Stratford (VR-380), Tembusu (VR-381), Dakar bat (VR-382), Ntaya (VR-78), Banzi (VR-414), Modoc (VR-415), Rio Bravo virus (VR-416), Cowbone ridge (VR-417), Bukalasa (VR-418), Montana myotis leukoencephalitis (VR-537), Bussuquara (VR-557), Sepik (VR-906), Cowbone ridge (VR-1253), Dengue type 2 (VR-1255), Dengue type 3 (VR-1256), Dengue type 4 (VR-1257), Ilheus (VR-1258), Rio Bravo virus (VR-1263), St. Louis encephalitis (VR-1265), West Nile (VR- 1267), Dengue type 4 (VR-1490), West Nile (VR-1507), and West Nile (VR-1510), each of which is incorporated herein by reference.

II. Proteinaceous Compositions

In various embodiments of the invention *Flavivirus*, TBE virus or West Nile virus polypeptides or proteins may be comprised in various proteinaceous compositions. These proteinaceous composition may be used in the detection of *flavivirus* members, vaccination against *flavivirus* members, as well as other methods and compositions described herein.

A. Proteinaceous Compositions

In certain embodiments, the present invention concerns novel compositions comprising at least one proteinaceous molecule, such as a rDIII polypeptide (antigen) alone or in combination with other *flavivirus* envelope proteins, envelope protein domain III or fragments thereof. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein. The term "antigen" refers to any substance or material that is specifically recognized by an antibody or T cell receptor. The term "epitope" refers to a specific antigenic determinant that is recognized by an antibody or T cell receptor. Thus, it is contemplated that the antigens of the invention may be truncations or only portions of a full-length polypeptide. For example, a "rDIII antigen" refers to a peptide or polypeptide containing contiguous amino acids of envelope protein domain III, including at least one envelope protein domain III epitope, but it may be fewer than a full-length amino acid sequence. Thus, an envelope protein domain III antigen may include a region of contiguous amino acids derived from any of SEQ ID NO:3-21.

SEQ ID NO:2 corresponds to protein accession number NP_041724, which is the sequence for a West Nile virus. SEQ ID NO:3 corresponds to amine acids 291-787 of SEQ ID NO:2, which is a full-length processed LE protein envelope protein domain III polypeptide sequence. Immunogenic regions of *flavivirus* envelope proteins have been described, and the present invention includes antigens that include one or more such regions.

In certain embodiments, a proteinaceous molecule comprising a TBE serocomplex virus or a West Nile virus envelope protein domain III antigen may comprise, be at least, or be at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 150, 160, 170, 180, 190, 200 or greater contiguous amino acid residues, and any range derivable therein of SEQ ID NO:2, or SEQ ID NO:3-21.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Encompassed by certain embodiments of the present invention are peptides, such as, for example, a peptide comprising all or part of a *flavivirus* envelope antigen (including at least one epitope) of any subtype or clade. Peptides of the invention may comprise, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111 contiguous amino acids, including all or part of any of SEQ ID NO:2-21.

Accordingly, the term "proteinaceous composition" encompasses amino molecule sequences comprising at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid |
|---|---|
| Aad | 2-Aminoadipic acid |
| Baad | 3- Aminoadipic acid |
| Bala | β-alanine, β-Amino-propionic acid |
| Abu | 2-Aminobutyric acid |
| 4Abu | 4- Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be viral proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (www.ncbi.nlm.nih.gov). The coding regions for these known genes may be amplified and/or expressed using the techniques disclosed herein or as would be low to those of ordinary skill in the art. Alternatively, various commercial preparations of proteins, polypeptides and peptides are known to those of skill in the art.

In certain embodiments a proteinaceous compound may be purified. Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide. In still further embodiments, a proteinaceous compound may be purified to allow it to retain its native or non-denatured conformation. Such compounds may be recombinantly derived or they may be purified from endogenous sources.

In certain embodiments, the proteinaceous composition may comprise at least one antigen of a flaviviral envelope protein domain III that is recognized by an antibody. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is also used to refer to any antibody-like molecule that has an antigen binding region, and includes antibody fragments such as Fab', Fab, $F(ab')_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Harlow et al., 1988; incorporated herein by reference).

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that it will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

1. Variants of *Flavivirus* Envelope Protein Domain III Antigens

Amino acid sequence variants of the polypeptide of the present invention can be substitutional, insertional or deletion variants. Deletion variants lack one or more residues of the native protein that are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine or histidine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "functionally equivalent codon" is used herein to refer to codons that encode the same amino acid, such as the six codons for arginine or serine, and also refers to codons that encode biologically equivalent amino acids (see Table 2, below).

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of immunogenicity or antibody binding. The addition of terminal sequences particularly applies to nucleic acid sequences that may, for example, include various non-coding sequences flanking either of the 5' or 3' portions of the coding region or may include various internal sequences, i.e., introns, which are known to occur within genes.

TABLE 2

Codon Table

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 2, above, shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and/or an immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, and size. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See e.g., Johnson (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outlined above, to engineer second generation molecules having many of the properties of *flavivirus* envelope protein domain III antigens, but with altered and even improved characteristics.

2. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a region to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

3. Protein Purification

It is desirable to purify *flavivirus* envelope protein domain III antigens or variants thereof. These techniques involve, at one level, the crude fractionation of the cellular milieu to polypeptide and non-polypeptide fractions. Certain embodiments of the invention are directed at preserving the conformation of *flavivirus* envelope protein domain III antigens as much as possible so that they are substantially non-denatured.

Antigens of the invention may be purified using gentle, non-denaturing detergents, which include, but are not limited to, NP40 and digitonin. Infected or transfected host cells may be solubilized using a gentle detergent. The following conditions are considered "substantially denaturing" or "denaturing": 10 mM CHAPS, 0.5% SDS, >2% deoxycholate, or 2.0% octylglucoside. Antigens prepared under such conditions would not be considered "non-denatured antigens." Preparations of substantially non-denatured antigens of the invention may be accomplished using techniques described in U.S. Pat. Nos. 6,074,646 and 5,587,285, which are hereby incorporated by reference herein.

Certain aspects of the present invention concern the purification, and in particular embodiments, the substantial purification, of an encoded protein or peptide. The term "purified protein" or "purified peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. Methods exhibiting a lower degree of relative purification may have advantages in total recovery of protein product, or in maintaining the activity of an expressed protein.

4. Antibodies

The present invention concerns the detection of *flavivirus*, TBE serocomplex virus or West Nile virus antibodies using *flavivirus*, TBE virus or West Nile virus antigens. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. As described earlier, an antigen may include one or more epitopes and an antigen refers to any part of a polypeptide that contains at least one epitope.

The term "antibody" is used to refer to any antibody-like molecule that has an antigen binding region. The techniques for preparing and using various antibody-based constructs and fragments are well known in the art. Means for preparing and characterizing antibodies are also well known in the art (See, e.g., Harlow and Lane, 1988; incorporated herein by reference).

In addition to polypeptides, antigens of the invention may be peptides corresponding to one or more antigenic determinants of the *flavivirus* envelope protein domain III polypeptides of the present invention. Thus, it is contemplated that detection of a *flavivirus*, a TBE virus or West Nile virus antibody may be accomplished with a *flavivirus* envelope protein domain III antigen that is a peptide or polypeptide.

Such peptides should generally be at least five or six amino acid residues in length and will preferably be about 10, 11, 12, 13, 14, 15, 16, 17, 18, 19, 20, 25 or about 30 amino acid residues in length, and may contain up to about 35, 40, 45, 50, 55, 60, 65, 70, 75, 80, 85, 90, 95, 100, 105, 110, 111 or more residues and values there between. For example, these peptides may comprise a WN DIII antigen sequence, such as 5, 6, 7, 8, 9, 10, 11, 12, 13, 14, 15, 16, 17, 18, 19, 20, 21, 22, 23, 24, 25, 30, 35, 40, 45, 50, 110 or more contiguous amino acids from any of SEQ ID NO:3 or 11; or a TBE-DIII antigen, such as 5, 6, 7, 8, 9, 10, 11, 12, 13, 14, 15, 16, 17, 18, 19, 20, 21, 22, 23, 24, 25, 30, 35, 40, 45, 50, 110 or more contiguous amino acids from any of SEQ ID NO:14-20. Synthetic peptides will generally be about 35 residues long, which is the approximate upper length limit of automated peptide synthesis machines, such as those available from Applied Biosystems (Foster City, Calif.). Longer peptides also may be prepared, e.g., by recombinant means.

U.S. Pat. No. 4,554,101, incorporated herein by reference, teaches the identification and preparation of epitopes from primary amino acid sequences on the basis of hydrophilicity. Through the methods disclosed, one of skill in the art would be able to identify epitopes and/or antigens from within an amino acid sequence such as a *flavivirus*, TBE virus or West Nile virus sequence disclosed herein in as SEQ ID NO:2, 3, 4, 5, 6, 7, 8, 9, 10, 11, 12, 13, 14, 15, 16, 17, 18, 19, 20, 21.

Numerous scientific publications have also been devoted to the prediction of secondary structure, and to the identification of epitopes, from analyses of amino acid sequences (Chou and Fasman, 1974a, b; 1978a, b; 1979). Any of these may be used, if desired, to supplement the teachings of Hopp in U.S. Pat. No. 4,554,101.

Moreover, computer programs are currently available to assist with predicting antigenic portions and epitopic core regions of proteins. Examples include those programs based upon the Jameson-Wolf analysis (Jameson and Wolf, 1988; Wolf et al., 1988), the program PepPlot® (Brutlag et al., 1990; Weinberger et al., 1985), and other new programs for protein tertiary structure prediction (Fetrow and Bryant, 1993). Another commercially available software program capable of carrying out such analyses is MacVector (IBI, New Haven, Conn.).

In further embodiments, major antigenic determinants of *flavivirus*, TBE or West Nile envelope protein domain III polypeptide may be identified by an empirical approach in which portions of the gene encoding a *flavivirus*, TBE or West Nile envelope protein(s) are expressed in a recombinant host, and the resulting proteins tested for their ability to elicit an immune response. Alternatively all or past of *flavivirus* envelope proteins from different subtypes or clades of different *flaviviruses* may be tested. A range of peptides lacking successively longer fragments of the C-terminus of the protein can be assayed as long as the peptides are prepared to retain their structure as it would be in a native polypeptide. The immunoactivity of each of these peptides is determined to identify those fragments or domains of the polypeptide that are immunodominant. Further studies in which only a small number of amino acids are removed at each iteration then allows the location of the antigenic determinants of the polypeptide to be more precisely determined.

Once one or more such analyses are completed, polypeptides are prepared that contain at least the essential features of one or more antigenic determinants. The peptides are then employed in the generation of antisera against the polypeptide. Minigenes or gene fusions encoding these determinants also can be constructed and inserted into expression vectors by standard methods, for example, using PCR™ cloning methodology.

5. Immunodetection Methods

As discussed, in some embodiments, the present invention concerns immunodetection methods for binding, purifying, removing, quantifying and/or otherwise detecting *flavivirus* antibodies in a sample, particularly TBE virus or West Nile virus antibodies, using DIII antigens. The samples may be any biological fluid or tissue from a patient or subject or animal host. The sample may be placed on a non-reactive surface such as a plate, slide, tube, or other structure that facilitates in any way the screening of the sample for *flavivirus* antibodies. While samples may be individually screened, large numbers of samples may be screened, such as for detecting contamination in blood bank samples.

Immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature, such as, e.g., Doolittle et al., 1999; Gulbis et al., 1993; De Jager et al., 1993; and Nakamura et al., 1987, each incorporated herein by reference.

In general, the immunobinding methods include obtaining a sample suspected of containing a *flavivirus*, in particular a TBE virus or a West Nile virus antibody with a composition comprising a *flavivirus*, TBE virus or West Nile DIII antigen in accordance with the present invention under conditions effective to allow the formation of immunocomplexes.

These methods include methods for purifying am antibody from bodily fluids, tissue or organismal samples. In these instances, the antigen removes the antibody component from a sample. The antigen will preferably be linked to a solid support, such as in the form of a column matrix, and the sample suspected of containing the antibody will be applied to the immobilized antigen. The unwanted components will be washed from the column, leaving the antibody immunocomplexed to the immobilized antigen to be eluted. Alternatively, sandwich versions of this assay may be employed.

The immunobinding methods also include methods for detecting and quantifying the amount of an antibody component in a sample and the detection and quantification of any immune complexes formed during the binding process. Here, one would obtain a sample suspected of containing an antibody and contact the sample with an antigen, and then detect and, quantify the amount of immune complexes formed under the specific conditions.

In terms of antigen detection, the biological sample analyzed may be any sample that is suspected of containing an antibody, such as, for example, a tissue section or specimen, a homogenized tissue extract, a cell, an organelle, separated and/or purified forms of any of the above antibody-containing compositions, or even any biological fluid that comes into contact with the cell or tissue, including blood and/or serum.

Contacting the chosen biological sample with the antigen under effective conditions and for a period of time sufficient to allow the formation of immune complexes (primary immune complexes) is generally a matter of simply adding the antigen composition to the sample and incubating the mixture for a period of time long enough for any antibodies present to form immune complexes with, i.e., to bind to, antigens. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antigen employed in the detection may itself be linked to a detectable label, wherein one would then simply detect this label, thereby allowing the amount of the primary immune complexes in the composition to be determined. Alternatively, the first antigen that becomes bound within the primary immune complexes may be detected by means of a second binding ligand that has binding affinity for the antigen. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

a. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques. Western blotting, dot blotting, FACS analyses, peptide arrays may also be used to detect antigen/antibody interaction.

Turning first to immunoassays, in their most simple and direct sense, preferred immunoassays of the invention include the various types of enzyme linked immunosorbent assays (ELISAs) known to the art. However, it will be readily appreciated that the utility of the DIII preparations described herein are not limited to such assays, and that other useful embodiments include RIAs and other non-enzyme linked antibody binding assays or procedures.

In some embodiments of the ELISA assay, *flavivirus*, TBE virus or West Nile virus envelope proteins or appropriate peptides incorporating DE antigen sequences are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA), casein, solutions of milk powder, gelatin, PVP, superblock, or horse albumin onto the well that is known to be antigenically neutral with regard to the test antisera. This allows for blocking of nonspecific adsorption sites on the immobilizing surface and thus reduces the background caused by nonspecific binding of antisera onto the surface. Following an appropriate coating period (for example, 3 hours), the coated wells will be blocked with a suitable protein, such as bovine serum albumin (BSA), casein, solutions of milk powder, gelatin, PVP, superblock, or horse albumin, and rinsed several times (e.g., 4 or 5 times) with a suitable buffer, such as PBS. The wells of the plates may then be allowed to dry, or may instead be used while they are still wet.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 1 to 4 hours, at temperatures preferably on the order of 20° to 25° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing, the occurrence and even amount of immunocomplex formation may be determined by subjecting same to a second antibody having specificity for the first. Of course, in that the test sample will typically be of human origin, the second antibody will preferably be an antibody having specificity in general for human IgG, IgM or IgA. To provide a detecting means, the second antibody will preferably have an associated enzyme that will generate a color development upon incubating with an appropriate chromogenic substrate. Thus, for example, one will desire to contact and incubate the antisera-bound surface with a urease, alkaline phosphatase, or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethylbenzthiazoline-6-sulfonic acid (ABTS) and $H_2O_2$, in the case of peroxidase as the enzyme label. Quantification is then achieved by measuring the degree of color generation, e.g., using a visible spectra spectrophotometer.

In an exemplary embodiment, in each of the microtiter wells will be placed about 10 μl of the test patient sample along with about 90 μl of reaction buffer (e.g., PBS with about 1% digitonin or other mild protein solubilizing agent). Control wells of the ELISA plate will include normal sera (human sera without *flavivirus* antibody), and anti-*flavivirus* antibody collected from subjects.

Irrespective of the format employed, ELISAs have certain features in common, such as coating, incubating and binding, washing to remove non-specifically bound species, and detecting the bound immune complexes. These are described below.

In coating a plate with either antigen on antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of every minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

b. Assay Plates

In some embodiments, the wells of the assay plates may first be coated with an anti-DIII, antiTBE-DIII and/or anti-WN-DIII antibody. This would immobilize DIII antigen to the plastic in the presence of a mild solubilizing buffer, such as from about 0.1% to about 10% digitonin (particularly about 1% digitonin). Such an approach is particularly efficacious in preparing assay plates with wells made of plastic.

The assay plates in other embodiments of the invention comprise a multiplicity of microtiter wells, and in some embodiments, polystyrene microtiter wells. These wells would be coated with about 500 ng/well of the rDIII, TBE-rDIII or WN-rDIII antigen.

c. Immunohistochemistry

The antigens of the present invention may also be used in conjunction with both fresh-frozen and/or paraffin-embedded tissue blocks prepared for study by immunohistochemistry (IHC). *Flavivirus*, TBE virus and West Nile virus antibodies may be identified in this manner. The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

III. Nucleic Acid Molecules

In some embodiments, the present invention concerns envelope protein domain III antigens prepared from genomic or recombinant nucleic acids. Some of the teachings herein pertain to the construction, manipulation, and use of nucleic acids to produce a recombinant envelope protein domain III antigen.

A. Polynucleotides Encoding E Protein Domain III Envelope Antigens

The present invention concerns polynucleotides, isolatable from cells or viruses, that are free from cellular or viral genomic DNA or RNA and are capable of expressing all or part of a protein or polypeptide. The polynucleotide may encode a peptide or polypeptide containing all or part of an envelope protein domain III amino acid sequence or may encode a peptide or polypeptide having an envelope protein domain III antigen sequence. Recombinant proteins can be purified from expressing cells to yield denatured or non-denatured proteins or peptides.

As used herein, the term "DNA segment" refers to a DNA molecule that has been isolated free of total genomic DNA of a particular species or genomic RNA of a virus. Therefore, a DNA segment encoding a polypeptide refers to a DNA segment that contains wild-type, polymorphic, or mutant polypeptide-coding sequences yet is isolated away from, or purified free from, total viral RNA or, mammalian, or human genomic DNA. Included within the term "DNA segment" are recombinant vectors, including, for example, plasmids, cosmids, phage, viruses, and the like.

As used in this application, the term "envelope protein domain III (DIII) polynucleotide" refers to an envelope protein domain III polypeptide-encoding nucleic acid molecule that has been isolated free of total genomic nucleic acid. Therefore, a "polynucleotide encoding an envelope protein domain III antigen" refers to a DNA segment that contains all or part of envelope protein domain III polypeptide-coding sequences isolated away from, or purified free from, total viral genomic nucleic acid.

It also is contemplated that a particular polypeptide from a given species or strain may be represented by natural variants that have slightly different nucleic acid sequences but, nonetheless, encode the same protein (see above).

Similarly, a polynucleotide comprising an isolated or purified gene refers to a DNA segment including, in certain aspects, regulatory sequences, isolated substantially away from other naturally occurring genes or protein encoding sequences. In this respect, the term "gene" is used for simplicity to refer to a functional protein, polypeptide, or peptide-encoding unit. As will be understood by those in the art this functional term includes genomic sequences, cDNA sequences, RNA sequences and smaller engineered gene segments that express, of may be adapted to express, proteins, polypeptides, domains, peptides, fusion proteins, and mutants. A nucleic acid encoding all or part of a native or modified polypeptide may contain a contiguous nucleic acid sequence encoding all or a portion of such a polypeptide of the following lengths: about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760; 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, which may be contiguous nucleotides encoding any length of contiguous amino acids of SEQ ID NO:2, or any of SEQ ID NO:3-21.

In particular embodiments, the invention concerns isolated DNA segments and recombinant vectors incorporating DNA sequences that encode a DIII antigen polypeptide or peptide, such as all or part of DIII, which includes within its amino acid sequence a contiguous amino acid sequence in accordance with, or essentially corresponding to a native polypeptide. Thus, an isolated DNA segment or vector containing a DNA segment may encode, for example, a DIII antigen that is capable of binding to an anti-*flavivirus* antibody. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

Encompassed by certain embodiments of the present invention are DNA segments encoding relatively small peptides, such as, for example, a peptide comprising all or part of an envelope protein DIII antigen (including at least one epitope) of any subtype or clade of *flavivirus*.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode full-length envelope protein from any *flavivirus* or encode a truncated version of the polypeptide, for example a truncated envelope protein domain III polypeptide, such that the transcript of the coding region represents the truncated version. The truncated transcript may then be translated into a truncated protein. Alternatively, a nucleic acid sequence may encode a full-length polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In a non-limiting example, one or more nucleic acid constructs may be prepared that include a contiguous stretch of nucleotides identical to or complementary to a particular gene, such as a envelope protein gene of a particular *flavivirus* or subtype or strain of a *flavivirus*. A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

The DNA segments used in the present invention encompass immunologically or biologically functional equivalent modified polypeptides and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

The sequence of a *flavivirus* envelope protein III polypeptide will substantially correspond to a contiguous portion of that shown in amino acids 292-402 of SEQ ID NO:3 or any of SEQ ID NO:4-21 and have relatively few amino acids that are not identical to, or an immunological or a biologically functional equivalent of, the amino acids shown in amino acids 292-402 of SEQ ID NO:3 or any of SEQ ID NO:4-21. The term "immunologically functional equivalent" or "biologically functional equivalent" is well understood in the art and is further defined in detail herein to include an ability to bind or be recognized by a specific *flavivirus* antibody.

Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:3-21 will be sequences that are "essentially as set forth in SEQ ID NO:3-21."

In certain other embodiments, the invention concerns isolated DNA segments and recombinant vectors that include within their sequence a contiguous nucleic acid sequence from that shown in SEQ ID NO:1. This definition is used in the same sense as described above and means that the nucleic acid sequence substantially corresponds to a contiguous portion of that shown in SEQ ID NO:1 and has relatively few codons that are not identical, or functionally equivalent, to the codons of SEQ ID NO:1. The term "functionally equivalent codon" is used herein to refer to codons that encode the same amino acid, such as the six codons for arginine or serine, and also refers to codons that encode biologically equivalent amino acids. See Table 2 above, which lists the codons preferred for use in humans, with the codons listed in decreasing order of preference from left to right in the table (Wada et al., 1990). Codon preferences for other organisms also are well known to those of skill in the art (Wada et al., 1990, included herein in its entirety by reference).

The various probes and primers designed around the nucleotide sequences of the present invention may be of any length. By assigning numeric values to a sequences, for example, the first residue is 1, the second residue is 2, etc., an algorithm defining all primers can be proposed:

$$n \text{ to } n+y$$

where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

It also will be understood that this invention is not limited to the particular nucleic acid encoding amino acid sequences of SEQ ID NO:2, or any of SEQ ID NO:3-21. Recombinant vectors and isolated DNA segments may therefore variously include the envelope protein DIII antigen-coding regions themselves, coding regions bearing selected alterations or modifications in the basic coding region, or they may encode larger polypeptides that nevertheless include envelope protein DIII antigen-coding regions or may encode biologically functional equivalent proteins or peptides that have variant amino acids sequences.

1. Vectors

Native and modified polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (2001) and Ausubel et al., 1996, both incorporated herein by reference. In addition to encoding a modified polypeptide such as modified envelope protein DIII, a vector may encode non-modified polypeptide sequences such as a tag or targeting molecule. Useful vectors encoding such fusion proteins include pIN vectors (Inouye et al., 1985), vectors encoding a stretch of histidines, and pGEX or pMAL vectors, for use in generating glutathione S-transferase (GST) or maltose binding protein (MBP) soluble fusion proteins for later purification and separation or cleavage. A targeting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

Vectors may include a "promoter," which is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements cant be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,919, herein incorporated by reference).

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

2. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris.*

Examples of eukaryotic host cells for replication and/or expression of a vector include Vero, HeLa, NIH3T3, Jurkat, 293, COS, CHO, Saos, and PC12. Many host cells from various cell types and organisms are available and would be known to one of skill in the art. Similarly, a viral, vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MaxBac® 2.0 from Invitrogen® and BacPack™ Baculovirus Expression System From Clontech®.

In addition to the disclosed expression systems of the invention, other examples of expression systems include Stratagene®'s Complete Control™ Inducible Mammalian Expression System, which involves a synthetic ecdysone-inducible receptor, or its pET Expression System, an *E. coli* expression system. Another example of an inducible expression system is available from Invitrogen®, which carries the T-Rex™ (tetracycline-regulated expression) System, an inducible mammalian expression system that uses the full-length CMV promoter. Invitrogen® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

IV. Kits and Diagnostics

The exemplary studies described herein show that rDIII is an excellent tool for differentiating infections caused by TBE serogroup versus mosquito-borne *flaviviruses*. This reagent would be particularly useful in regions where tick-borne and/or mosquito-borne *flaviviruses* are endemic, such as Asia, Europe and North America as well as economically depressed countries as it is relatively simple and inexpensive to produce.

The studies described herein extend and improve upon the use of recombinant *flavivirus* envelope protein DIII for the detection of TBE and/or WN virus infection. Recombinant DIII derived from the WN virus was found to be very specific and highly sensitive for identifying infection in naturally infected primates. Embodiments of the invention use rDIII as a diagnostic reagent for detecting TBE serocomplex virus infections. Assays using rDIII specific homologous and heterologous antiserum demonstrated a very high degree of sensitivity and specificity and tests using mouse hyperimmune serum supported these results. A potential drawback of the rDIII-based diagnostic assay may be the inability to differentiate between the TBE serocomplex viruses. It is contemplated that the minimization of potential binding epitopes may be accomplished by using peptide based diagnostic assays. Peptide based assays may be used to produce a greater degree of specificity to differentiate the TBE serocomplex of viruses immunologically. In other embodiments of the invention, the use of the rDIII-based ELISAs as a rapid preliminary test for TBE virus infection can be followed by further clinical and laboratory tests such as virus isolation or neutralization assays to conclusively identify the virus causing disease. In certain embodiments, rDIII can be used in a "dipstick" format by cross-linking the C-terminus of the protein to a solid substrate. This format would allow complete exposure of all rDIII antibody epitopes to test sera. The rDIII is an extremely stable protein as was shown by retention of the structure of TBE rDIII in up to 4M urea, 2M guanidinium hydrochloride and at low pH. The physical properties of the rDIII would lend themselves to the use of the rDIII reagent in unfavorable environmental conditions such as extreme heat or cold, or after extended storage. Recombinant protein technology for making these diagnostics reagents will also minimize the cost of diagnosis, which in turn will make the use of such reagents feasible in economically depressed countries.

In yet another aspect of the invention, a kit is envisioned for anti-*flavivirus*, anti-TBE virus or anti-West Nile virus antibody detection. In some embodiments, the present invention contemplates a diagnostic kit for detecting anti-TBE or anti-West Nile virus anti-bodies and human TBE or West Nile virus infection. The kit comprises reagents capable of detecting the anti-TBE or anti-West Nile antibody immunoreactive with the native or recombinant DIII antigens described here. Reagents of the kit include at least one DIII antigen, such as all or part of a TBE DIII and/or West Nile DIII, and any of the following: another DIII antigen, buffers, secondary antibodies or antigens, or detection reagents, or a combination thereof.

In some embodiments, the kit may also comprise a suitable container means, which is a container that will not react with components of the kit, such as an eppendorf tube, an assay plate, a syringe, or a tube. In specific embodiments, the kit comprises an array or chip on which one or more DIII antigen(s) is placed or fixed, such as those described in Reneke et al., 1998, which is herein incorporated by reference.

In other embodiments of the invention, in addition to comprising a DIII antigen, it comprises a secondary antibody capable of detecting the anti-*flavivirus*, anti-TBE virus or anti-West Nile virus antibody that is immunoreactive with the recombinant DIII antigen.

The *flavivirus* antigen reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, peptide array plate, plastic beads or plates, or a microscope slide. When the reagent provided is a dry powder, the powder can be reconstituted by the addition of a suitable solvent. In yet other embodiments, the kit may further comprise a container means comprising an appropriate solvent.

In some embodiments, the kit comprises a container means that includes a volume of a second antibody, such as goat anti-human IgG or IgM conjugated with alkaline phosphatase or other anti-human Ig secondary antibody, and a second container means that includes a volume of a buffer comprising a non-denaturing solubilizing agent, such as about 1% digitonin.

The kit may in other embodiments further comprise a third container means that includes an appropriate substrate, such as PNPP for alkaline phosphatase, or 9-dianisidine for peroxidase. A fourth container means that includes an appropriate "stop" buffer, such as 0.5 m NaOH, may also be included with various embodiments of the kit.

The kit may further include an instruction sheet that outlines the procedural steps of the assay, and will follow substantially the same steps as the typical EIA format known to those of skill in the art.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Virus Strains and Antigens

Strains of WN, JE, and St. Louis encephalitis (SLE) viruses used in this study are listed in Table 3. All viruses were obtained from the World Arbovirus Reference Collection at the University of Texas Medical Branch at Galveston (UTMB). The WN strains were chosen to represent subtypes of both genetic lineages I and II; genotypes of these viruses had previously been determined by sequencing of a region corresponding to the NS5/3'-non-coding region junction. The protocols for propagation and nucleotide sequencing of these viruses have been described elsewhere (Beasley et al., 2002).

Whole virus suckling mouse brain-derived antigen preparations for WN (strain 385-99), JE (strain Nakayama), SLE (strain Parsons) and MVE viruses were also obtained from the World Arbovirus Reference Collection.

TABLE 3

Origins and genotypes of West Nile virus strains.

| Strain | Origin | Year of Isolation | Lineage* | Designation |
|---|---|---|---|---|
| 385-99 | United States | 1999 | I | USA99b |
| EthAn4766 | Ethiopia | 1976 | I | ETH76 |
| TL443 | Israel | 1952 | I | ISR52 |
| Goldblum | Israel | 1953 | I | ISR53 |
| MRM16 | Australia | 1960 | I (Kunjin) | AUS60 |
| 804994 | India | 1980 | I (Indian) | IND80 |
| DakAnMg798 | Madagascar | 1978 | II | MAD78 |
| SPU116-89 | South Africa | 1989 | II | SA89 |
| DakArMg-979 | Madagascar | 1988 | II | MAD88 |
| H-442 | South Africa | 1958 | II | SA58 |

Recombinant WN Strain 385-99 Envelope Protein Domain III

A fragment corresponding to structural domain III of the WN virus strain 385-99 envelope protein (amino acids 296-415) was RT-PCR amplified for cloning and expression as a glutathione S-transferase (GST) fusion using the pGEX-2T system (Amersham Pharmacia Biotech, Piscataway N.J.). Protocols for expression and purification of the WN recombinant structural domain III of the envelope protein GST fusion protein (rDIII GST), followed by cleavage of the fusion protein and purification of WN rDIII away from the GST fusion partner, were based on those described by Bhardwaj et al. (2001). Briefly, RNA was extracted from culture supernatant of virus-infected Vero cells using the QiaAmp kit (Qiagen Inc., Valencia Calif.) and reverse transcribed using the AMV Reverse Transcriptase with random hexamer primers (Roche). Specific fragments representing envelope protein structural domain III with 5' and 3' restriction sites suitable for cloning were amplified using Taq polymerase (Roche). PCR products were gel purified, cloned into pGEM-TEasy (Promega Corp., Madison Wis.), digested using the appropriate restriction enzymes and subcloned into appropriately digested pGEX-2T vector. Inserts were sequenced in both directions to ensure fidelity of the products. Recombinant expression plasmids were transformed into DH5α *E. coli* for propagation and protein expression. Following induction, the fusion protein was purified on a glutathione sepharose column, and rDIII was subsequently cleaved from GST using thrombin (Novagen, Madison Wis.) and purified on a DEAE anion exchange column. Homogeneity of rDIII was confirmed by mass spectroscopy (data not shown).

Antisera and Monoclonal Antibodies

WN rDIII expressed and purified using the GST system was sent to Harlan Bioproducts for Science (Indianapolis, Ind.) to be used as an antigen for the preparation of a polyclonal rabbit serum. The antiserum was prepared using Harlan's standard immunization protocol in New Zealand White Rabbits (details available at "www.hbps.com"). Three WN Envelope protein reactive MAbs (5H10, 5C5 and 7H2) were obtained from Bioreliance Cop. (Rockville Md.). The binding of these MAbs to domain III, differences in their specificities, and the identification of putative binding sites for 5C5; and 5H10 are described elsewhere (Beasley and Barrett, 2002). Additional polyclonal mouse hyper-immune ascitic fluids (HIAF) against WN, JE, SLE, MVE, dengue type 2 (DEN2) and yellow fever (YF) viruses were obtained from the World Arbovirus Reference Collection.

Plaque Reduction Neutralization Tests (PRNT)

Ten-fold dilutions of virus ($10^{-1}$ to $10^{-6}$) were prepared in MEM tissue culture medium (Sigma) containing 2% fetal bovine serum (FBS) and mixed with equal volumes of anti-WN MAb or polyclonal anti-WN-rDIII serum, diluted 1/200 or 1/20 respectively, or MEM media only. Virus-antibody mixtures were incubated at room temperature for 60 minutes before inoculation into monolayers of Vero cells in 6-well tissue culture plates (Corning Inc., Corning N.Y.). Plates were incubated at room temperature for 30 minutes to allow virus adsorption, then overlayed with 5 mL per well of MEM medium containing 1% agarose (MEM/agarose). After incubation at 37° C./5% $CO_2$ for a suitable period (two or three days for WN virus strains; four or five days for JE/SLE viruses) wells were overlayed with an additional 2 mL of MEM/agarose containing 2% v/v neutral red solution (Sigma, St Louis Mo.). Plaques were counted the following day and neutralization indices determined as the $\log_{10}$ reduction in virus titer in the presence of MAb/polyclonal serum compared with the medium only control.

Indirect ELISA Assays

The wells of 96-well microtiter plates (Corning Inc.) were coated overnight at 4° C. with either WN, JE, MVE, or SLE virus antigen (equivalent to one pH 6.2 HA unit), or WN-rDIII protein (25 ng/well), diluted in borate saline (pH 9.0). These optimal dilutions of whole virus and recombinant antigens had been determined previously by titration against specific antisera (data not shown). Wells were blocked for 60 minutes with a solution of 3% bovine serum albumin in phosphate buffered saline (PBS) containing 5% tween-20 (PBS/tween), and then washed with PBS/tween. Serial doubling dilutions (1:100-1:6400) of anti-WN, -JE, -SLE, -MVE, -DEN2 and -YF mouse HIAFs were prepared in duplicate columns, the plates were incubated at room temperature for 45 minutes, and then washed four times with PBS/tween. Peroxidase-labeled anti-mouse immunoglobulin serum (Sigma) diluted 1:2500 in PBS/tween was added to each well, and plates were again incubated, washed (four times with PBS/tween, twice with PBS) and antibody binding visualized by addition of TMB substrate (Sigma). After incubating for 10 minutes at room temperature, color reactions were stopped by addition of 3M HCl and absorbances read at 490 nm on a Fluoromark plate reader (BioRad, Hercules Calif.).

Nucleotide Sequencing

RNA was extracted from WN virus-infected Vero cell supernatants and reverse transcribed as described earlier. A fragment that included the structural domain III coding sequence was RT-PCR amplified using primers WN1751

(5'-$_{1751}$TGCATCAAGCTTTGGCTGGA$_{1770}$) (SEQ ID. NO:22) and WN2504A (5'-$_{2504}$TCTTGCCGGCTGATGTCTAT$_{2485}$) (SEQ ID NO:23) for lineage I strains, or WN1739 (5'-$_{1751}$TGCACCAAGCTCTGGCCGGA$_{1770}$) (SEQ ID NO:24) and WN2498A (5,-$_{2510}$CCGAGCTCTTGCCTGCCAAT$_{2491}$) (SEQ ID NO:25) for lineage II strains. Primer pairs were designed based on Genbank sequences AF196835 and M12294 (each of which is incorporated herein by reference), respectively, and are numbered according to residues in the AF196835 sequence. PCR products of the appropriate sizes were gel purified and directly sequenced using the ABI PRISM Big Dye v3.0 cycle sequencing kit (Applied Biosystems) on an ABI PRISM 3100 genetic analyzer (Applied Biosystems) according to the manufacturer's protocols. Sequence analysis was performed using the Vector NTI Suite package (Informax Inc.).

Results

Specificity of Polyvalent Anti-WN Domain III Serum

Figure 3:
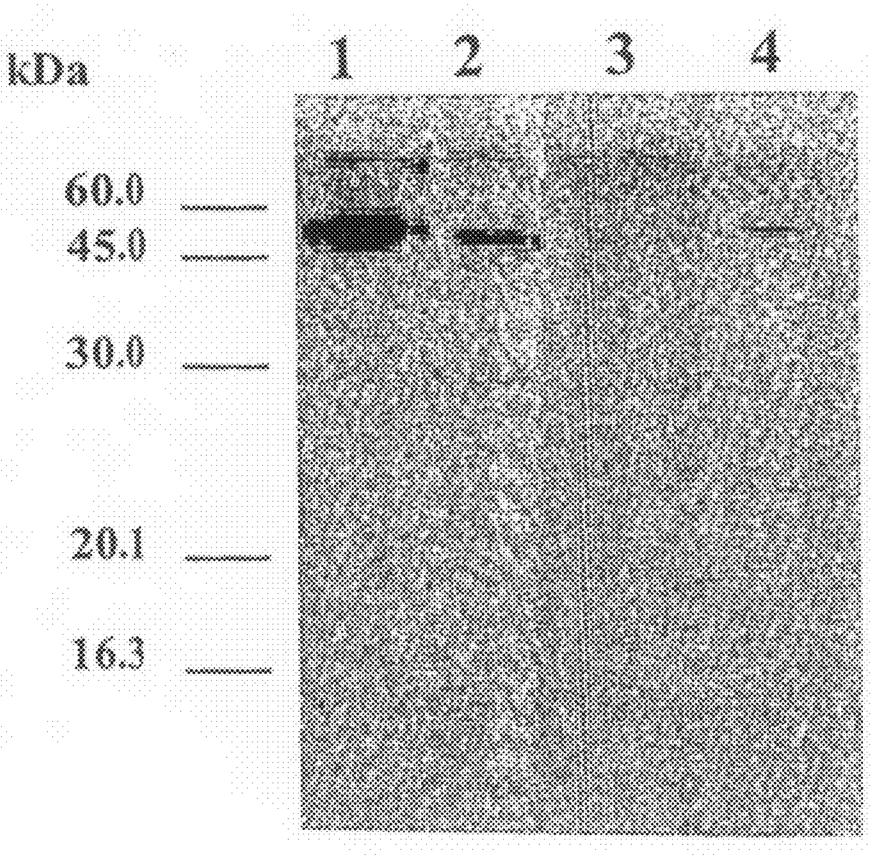
FIG. 3 illustrates the binding of rabbit antiserum raised against WN recombinant envelope protein domain III antigen to *flavivirus* envelope proteins in western blot assays with whole virus antigens of (1) WN, (2) JE, (3) SLE, and (4) MVE viruses.
Figure 4:
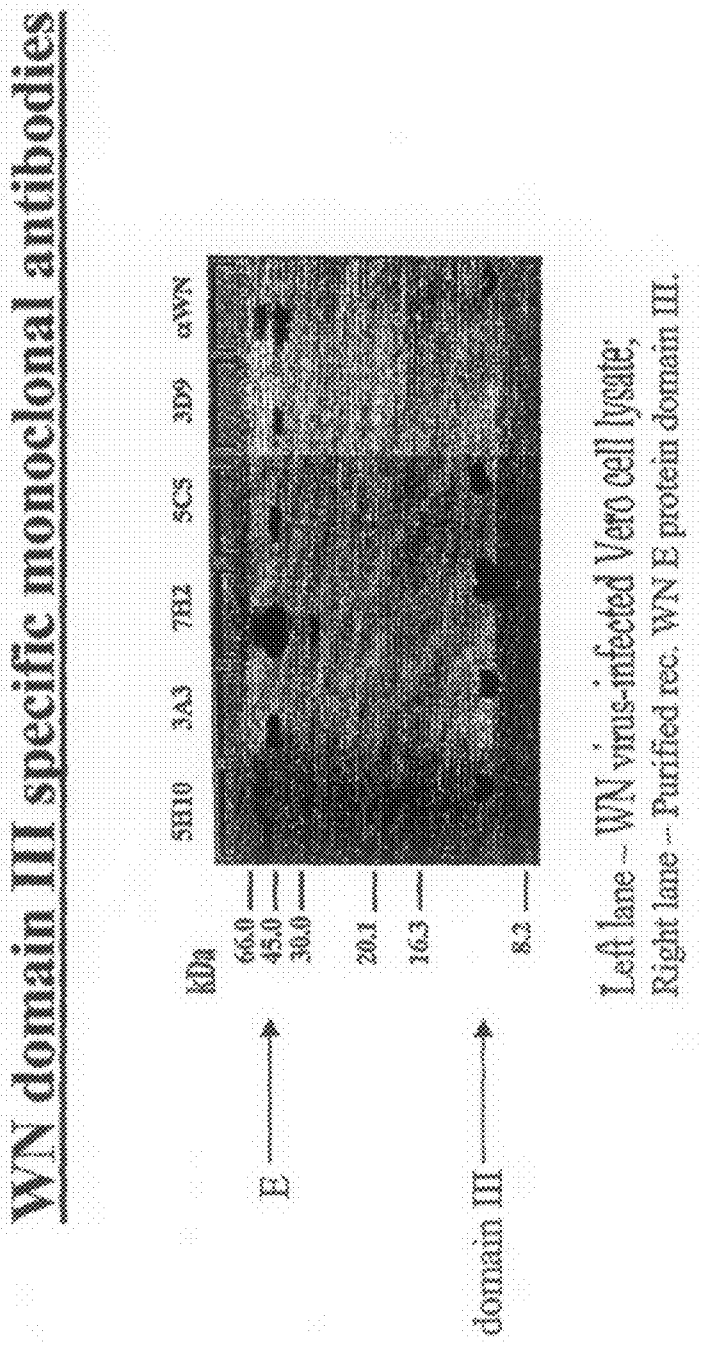
FIG. 4 illustrates Western blot analysis or WN envelope protein domain III specific monoclonal antibodies 5H10, 3A3, 7H2, 5C5, 3D9, and a polyclonal antiserum to WN envelope protein domain III.

To determine the specificity of polyvalent anti-domain III rabbit serum PRNT assays and Western blot with related JE serocomplex and other mosquito-borne *flaviviruses* were performed. In PRNT assays, the anti-domain III serum neutralized WN strain 385-99 by more than 5000-fold (Table 4), while less than 10-fold reductions in titre were observed in assays with JE, SLE, DEN or YF viruses. In Western blot assays with JE, MVE and SLE virus antigen preparations the inventors observed some weak cross-reactivity with the envelope proteins of those viruses (FIG. 3). In other western blot analysis the WN domain III specific monoclonal antibodies were characterized (FIG. 4).

TABLE 4

Variable neutralization of West Nile virus strains representative of genetic lineages I and II by Envelope protein domain III-specific monoclonal antibodies and a polyclonal antiserum
NEUTRALIZATION INDEX* AGAINST WN VIRUS STRAINS
Serum

| WN strain | 5H10 | 7H2 | 5C5 | Anti-D III |
|---|---|---|---|---|
| USA99b | 2.3 | 3.6 | 2.5 | 3.8 |
| ETH76 | 2.7 | 4.2 | 2.4 | 3.9 |
| ISR52 | 2.2 | 3.4 | 2.4 | 3.9 |
| ISR53 | 0.9 | 2.1 | 1.9 | 3.9 |
| AUS60 | 1.1 | 1.6 | 1.1 | 2.0 |
| IND80 | 1.7 | 2.6 | 2.5 | ≧5.6 |
| MAD78 | 2.5 | 3.1 | 2.5 | ≧4.8 |
| SA89 | 1.3 | 1.7 | 1.2 | 2.7 |
| MAD88 | 0.2 | 0.1 | −0.2 | 0.3 |
| SA58 | 0.2 | 0.1 | 0.1 | 0.6 |

*neutralization index is $\log_{10}$ reduction in virus titre in the presence of Mab/polyclonal serum compared with culture medium only control Variable Neutralization of WN Virus Strains by Anti-Domain III Serum and MAbs Having observed the specificity of the anti-domain III serum for WN virus in PRNT assays (FIG. 5), the inventors then tested whether this reagent could distinguish between subtypes of WN virus. In addition, the subtype specificity of the neutralizing domain III reactive MAbs was examined. Although differences in neutralization did not clearly delineate viruses of different genetic lineages, some variable neutralization of WN subtypes was observed (Table 4). In general, viruses of genetic lineage I were efficiently neutralized by both the polyclonal serum and the MAbs (~500- to 5000-fold reductions in titre), although neutralization of strain AUS60 (lineage I, Kunjin) was approximately 10 to 100-fold lower than that of other lineage I strains. Similarly, strain ISR53 was less efficiently neutralized by the MAbs than other lineage I strains, although this strain was still strongly neutralized by the polyclonal anti-domain III serum. Lineage II virus strain MAD78 was also strongly neutralized by MAbs and polyclonal serum, while strains MAD88 and SA58 completely escaped neutralization (less than 10-fold reductions in titer in the presence of either MAbs or serum). Neutralization of strain SA89 was incomplete (10- to 100-fold reductions in titer only) and was comparable to that of AUS60.

Correlation of Domain III Amino Acid Sequence with Neutralization Phenotype

Analysis of derived Envelope protein domain III amino acid sequences for each WN strain studied allowed the identification of residues that appeared to influence their neutralization phenotype (FIG. 6). Strains USA99b and ETH76 were identical throughout the region examined, while other lineage I strains differed at only one (ISR52 and ISR53) or three (AUS60, IND80) residues. Strain ISR53, which partially escaped neutralization by the MAbs but not the polyclonal serum (Table 4), contained a Thr→Ala substitution at E332 (amino acid 332 of the envelope protein). Strain AUS60, which partially escaped neutralization by MAbs and antiserum, differed at residues E310 (Lys→Thr), E339 (Val→Ile) and E366 (Ala→Ser) although the substitution at E339 was also observed in strain IND80, which did not escape neutralization. Additional substitutions in IND80 were identified at E312 (Leu→Val) and E390 (Glu→Asp). A His→Tyr substitution at E398 of strain ISR52 did not affect the neutralization of this strain. The lineage II strains studied all differed from USA99b at between two and four residues in domain III (FIG. 6). Strain SA89, which displayed partial escape from neutralization by MAbs and antiserum, contained the smallest number of substitutions, with changes at E312 (Leu→Ala) and E369 (Ala→Ser). Strains MAD88 and SA58, which escaped neutralization by MAbs and anti-domain III serum, shared the substitutions at E312 and E369, and contained an additional substitution at E332 (Thr→Lys). Strain MAD78, which was efficiently neutralized by both MAbs and antiserum, contained the greatest number of variable amino acids. This strain contained the E369 (Ala→Ser) substitution observed in the other lineage II strains examined, a Leu→Val change at E312 (also present in IND80), and additional unique substitutions at E371 (Val→Ile) and E375 (Leu→Ile).

Comparison with representative amino acid sequences of the comparable region of JE, SLE and MVE viruses revealed much greater variation, and substitutions were present at each of the critical residues for neutralization that were identified in the WN virus strains, and also at clusters of residues around these loci (FIG. 6).

Enhanced Specificity of WN r-DIII in Indirect Elisa Compared with Whole Virus Antigens The apparent type-specificity of functional epitopes in domain III (as evidenced by the limited neutralizing activity of the anti-domain III serum against other JE serocomplex viruses and some strains of WN lineage II) led us to investigate the utility of rDIII as an antigen for serological assays. Indirect ELISAs were performed using a panel of MIAF raised against several mosquito-borne *flaviviruses* (see Materials and Methods).

Figure 7:
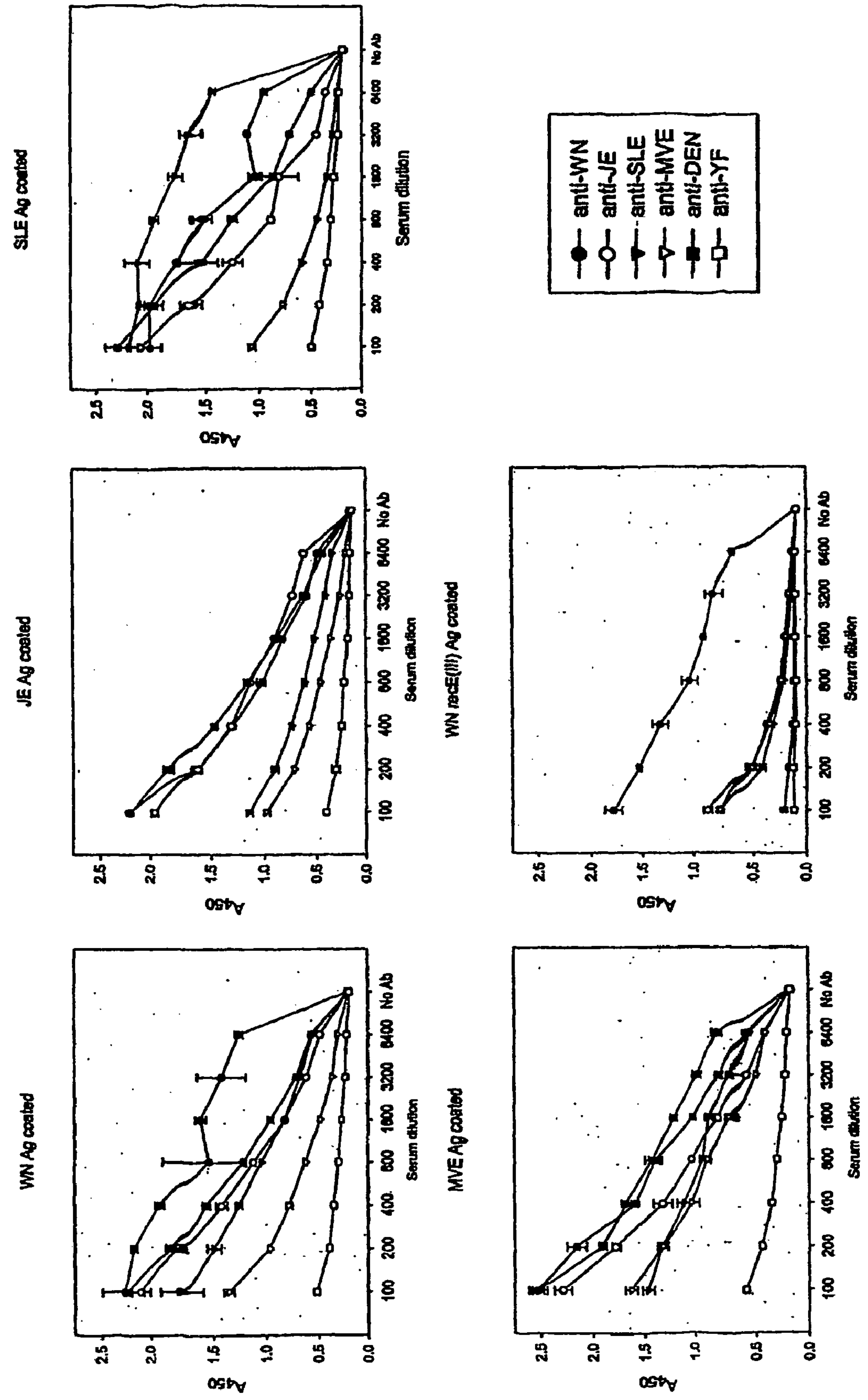
FIG. 7 illustrates the binding of selected anti-*flavivirus* mouse immune ascitic fluids in an indirect ELISA protocol utilizing whole-virus JE serocomplex antigens (WN, JE, SLE, or MVE viruses) or recombinant WN envelope protein domain III. Error bars 1 standard deviation from the mean.

In assays where plates were coated with whole virus antigens (inactivated WN, JE, MVE or SLE viruses) extensive cross-reactivity was observed with most MIAF antisera (FIG. 7). In general, the strongest reactions were observed between specific antigen/antiserum combinations (e.g. anti-WN serum with WN antigen). However, in each case, as least two other antisera reacted to at least 75% of the homologous serum at dilutions between 1:100 and 1:800. The binding activity of the anti-MVE MIAF was lower than the other JE serocomplex antisera in each assay, however its cross-reactive binding to WN, JE or SLE antigens was at least 60% of its binding to the MVE antigen.

In contrast, the binding of anti-WN MIAF to WN rDIII antigen cleaved from a MBP fusion was clearly discriminated from the other antisera; values at dilutions between 1:200 and 1:6400 were at least three-fold higher than those of sera raised against other *flavivirus* antigens (FIG. 7). The peak values obtained using the rDIII antigen were approximately 75% of those with whole virus WN antigen indicating some loss of sensitivity, as would be expected with the removal of binding sites contained in the remainder of the envelope protein.

Figure 8:
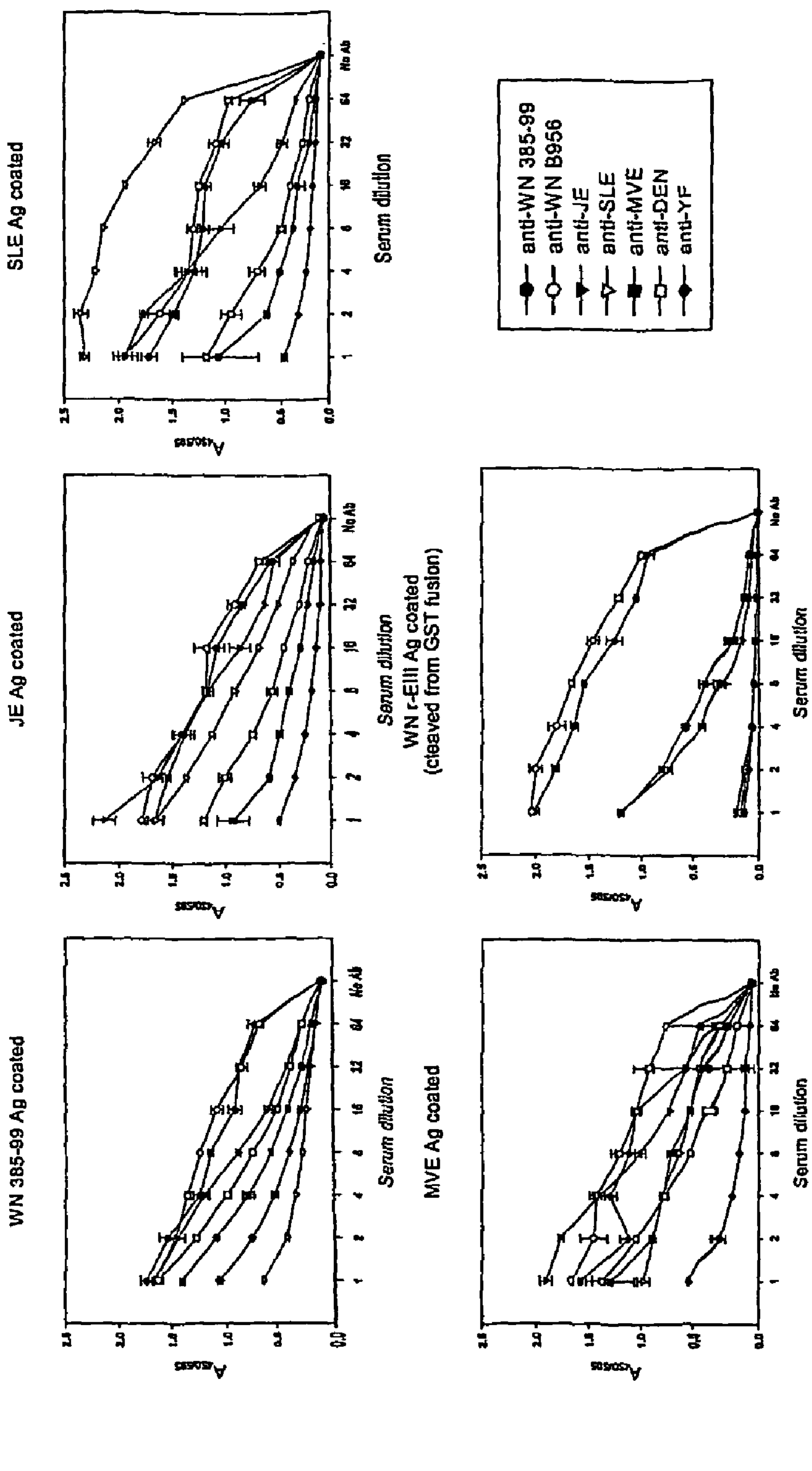
FIG. 8 illustrates the binding of selected anti-*flavivirus* mouse immune ascitic fluids in an indirect ELISA protocol utilizing whole-virus JE serocomplex antigens (WN, JE, SLE, or MVE viruses) or recombinant WN envelope protein domain III cleaved from a GST fusion protein.

Further studies have shown that WN rDIII antigen cleaved from a GST fusion protein yields greater specificity in indirect ELISA assays compared with whole virus antigen preparations (FIG. 8). Ninety-six-well ELISA plates were coated with sucrose-acetone extracted virus antigens (WN, JE, SLE or MVE equivalent to 4 HA units at pH6.2) or WN rDIII antigen. Serial dilutions of polyclonal mouse antisera raised against WN, JE, SLE, DEN or YF viruses were added to wells of plates (optimal antigen and antiserum dilutions had been determined by block titration of homologous antigen(Ag)/antibody(Ab) pairs); 2° Ab was HRP anti-mouse Ig; substrate was TMB.

Figures 9A, 9B, 9C:
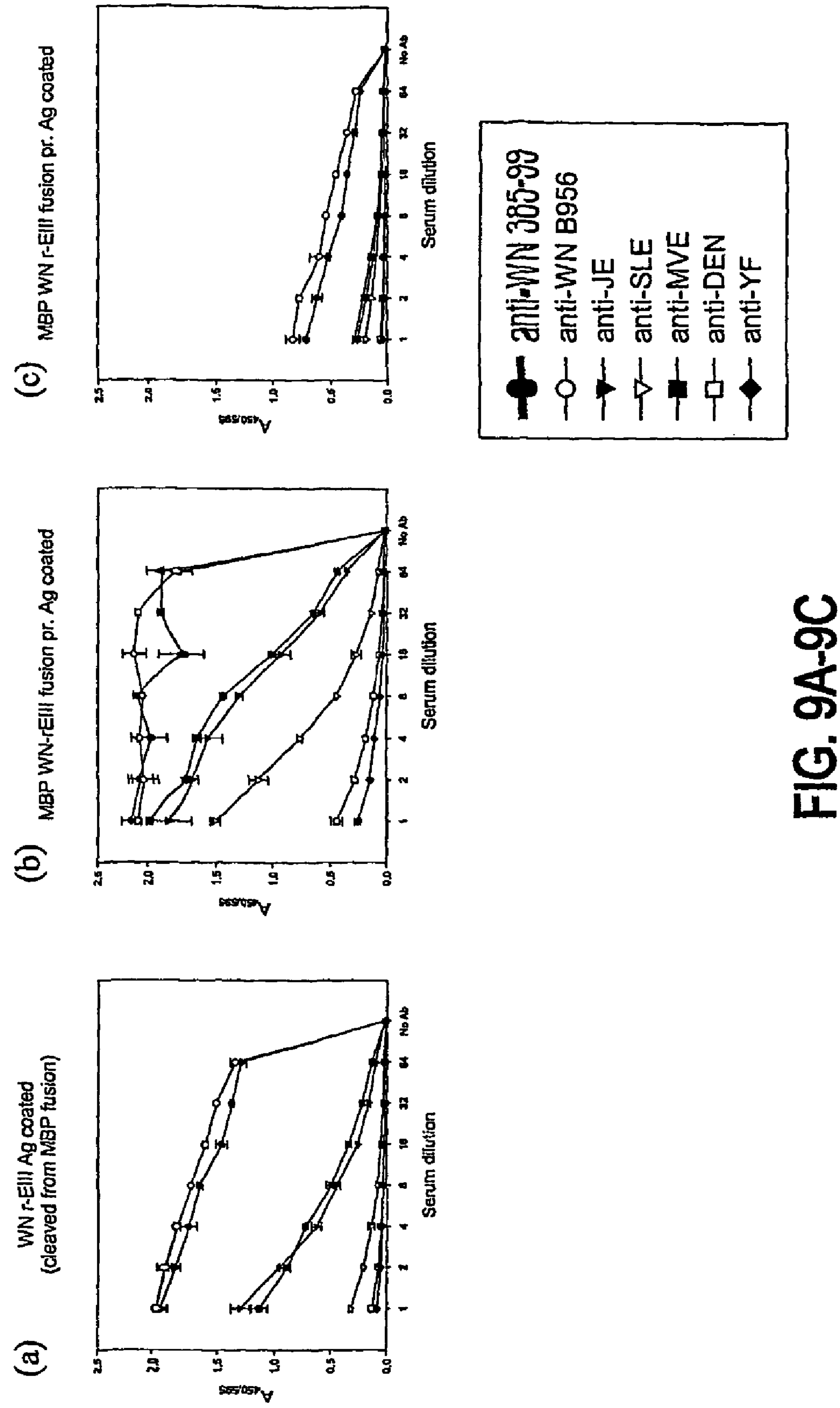
FIG. 9A-9C illustrates the binding of selected anti-*flavivirus* mouse immune ascitic fluids in an indirect ELISA protocol utilizing WN rDIII cleaved from an maltose binding protein (MBP) fusion protein, MBP WN rDIII fusion protein at 35 mg/well, and MBP WN rDIII fusion protein at 17.5 ng/well.

Additional studies showed that the use of cleaved, purified WN rDIII antigen yields greater specificity in indirect ELISA assays than use of purified MBP-DIII fusion protein antigen (FIG. 9). In brief, 96-well ELISA plates were coated with either (a) WN rDIII Ag (~15 ng/well) or WN rDIII as an MBP fusion (~35 ng/well and ~1.75 ng/well total protein in (b) and (c) respectively, which represents ~7 ng/well or 0.35 ng/well WN rDIII). Assays were performed using serial dilutions of polyclonal mouse sera as described previously. Note greater cross-reactive (possibly non-specific) binding in panel (b). Further dilution of MBP rDIII fusion protein antigen reduces apparent cross reactivity but with marked reduction in sensitivity.

Example 2

Materials and Methods

Generation of Recombinant Domain III:

Recombinant domain III (rDIII) protein was expressed in *E. coli* as a fusion protein using maltose-binding protein (MBP) as the fusion partner. Expression and purification was essentially following the manufacturer's instructions and was previously described. Briefly, the coding sequence for domain III of the viral envelope protein was cloned into the pMAL-c2x expression vector (New England Biolabs). The individual DIII molecules encompassed approximately residues 300-395 of the viral envelope protein. Cloning into the pMAL system added an additional serine to the N-terminus of the recombinant proteins. The fusion protein was expressed by induction with IPTG. Purification was achieved via lysing the cells by sonication followed by affinity purification over an amylose resin column (New England Biolabs). The fusion protein was cleaved with Factor Xa (Novagen) and the MBP and rDIII separated by size exclusion chromatography on a Superdex 75 column (Amersham/Pharmacia). Domain III was concentrated and stored at 4° C. until use. The TBE rDIII protein has been found to extremely stable under very stringent conditions (Bhardwaj et al. 2001, White et al., 2003) and is stable when stored at 4° C. for extended periods.

Antiserum Production:

Purified rDIII was provided to Harlan Bioproducts for Science (Indianapolis, Ind.) for production of rabbit antisera. Antiserum against each rDIII protein was produced in two New Zealand white rabbits. Testing of the antisera in ELISA and western blot assays found little difference between antisera generated in different rabbits against the same antigen (M. Holbrook, unpublished observations).

Antigens and Mouse Immune Ascitic Fluids:

Suckling mouse brain-derived viral antigens from dengue-2 (DEN2), dengue-4 (DEN4), yellow fever (YF) vaccine strain 17D, Japanese encephalitis (JE) strain Nakayama, Langat (LGT) strain TP21 and Powassan (POW) sprain LB were obtained from the World Arbovirus Reference Collection housed at the University of Texas Medical Branch. In addition, mouse hyperimmune ascitic fluid (MIAF) against DEN2, DEN4, JE, YF, West Nile (WN), LGT, POW, KFD and RSSE were also obtained from the World Arbovirus Reference Collection.

Western Blots:

Ten nanograms (ng) of purified rDIII was run on 12% SDS-PAGE gels and transferred to a nitrocellulose membrane for blotting. The blots were blocked with TBS-tween (20 mM Tris-pH 7.5, 150 mM NaCl, 0.05% tween 20) containing 3% dry milk powder (Blotto) for at least 30 min. at room temperature. The membranes were probed for 1 hr at room temperature with the appropriate antiserum diluted in Blotto at dilutions of 1:800-1:1000 dependent upon the antiserum. Blots were washed 3 times with Blotto and probed with a goat anti-rabbit-horseradish peroxidase (HRP) conjugated secondary antibody (Sigma) at a 1:2000 dilution in Blotto for 1 hr at room temperature. The blots were subsequently washed twice with Blotto and three times with TBS-tween. The presence of rDIII was detected using the ECL chemiluminescence substrate (Amersham/Pharmacia).

Indirect ELISAs:

Purified rDIII or mouse brain-derived viral antigen (Ag) was coated onto 96-well round bottom microtiter plates (Falcon) overnight at 4° C. in borate saline buffer (120 mM NaCl, 50 mM boric acid, pH 9.0). Preliminary experiments examining sensitivity of the assay found that wells coated with 10-20 ng of rDIII provided optimum sensitivity while Ag was coated in plates at 1 hemagglutination (HA) unit per well. Wells were blocked with PBS-tween (PBS with 0_5% tween-20) containing 3% bovine serum albumin (BSA) for 30 min. at room temperature then washed once with PBS-tween prior to incubation with antisera. Two-fold serial dilutions of antisera were made in duplicate wells. All dilutions were made fix PBS-tween. Following a 1 hr room temperature incubation with primary antibody, the plates were washed with PBS-tween and then incubated with either goat anti-mouse or goat anti-rabbit HRP conjugated secondary antibody at a 1:2000 dilution for 1 hr at room temperature. The plates were washed and then incubated with 50 μl 3,3',5,5'-Tetramethylbenzidine (TMB) (Sigma) colorometric detection reagent for 5 min at room temperature. The reaction was stopped with 50 μl 3M HCl and the plates were read at 450 nm with a reference wavelength of 595 nm.

Results

Figure 10:
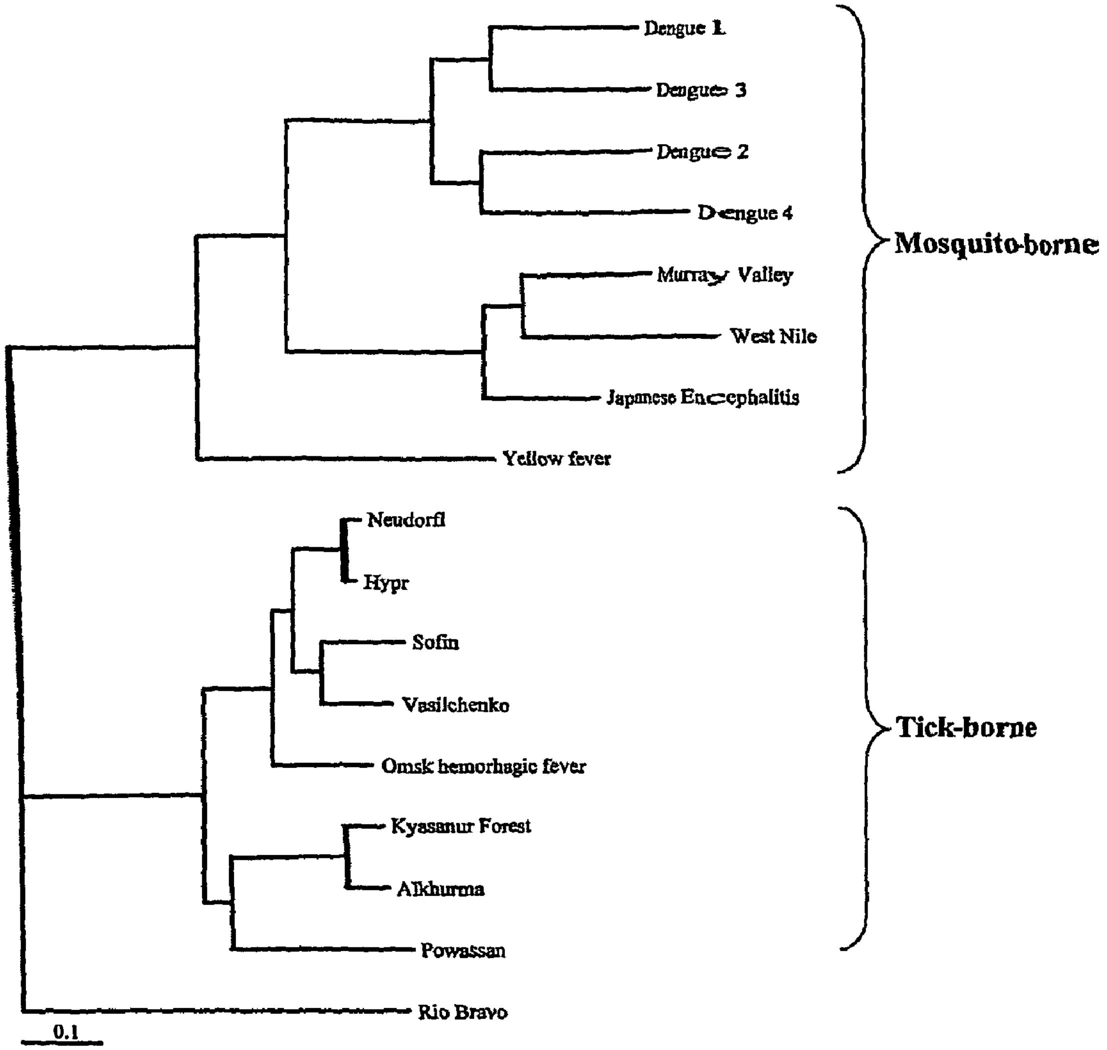
FIG. 10 Phylogentic analysis of the *flavivirus* envelope protein domain III amino acid sequence. Analysis was performed using maximum parsimony analysis. The tree was rooted using the non-vector borne Rio Bravo virus.

Cloning of Viral DIII:

The rDIII used in these assays were cloned from viruses representing several mosquito-borne *flaviviruses* and the major clades of the TBE serocomplex with the exception of the Siberian and Far-eastern subtypes of viruses (FIG. 10). Viral RNA for the Siberian and Far-eastern subtypes was not available as they are BSL-4 agents with restricted availability. Kumlinge (KUM) virus is a strain of CEE while OHF and KFD viruses are viruses that cause hemorrhagic fever rather than an exclusively encephalitic disease and form distinct subgroups within the serocomplex. LGT and POW viruses also represent distinct subgroups of the TBE serocomplex (FIG. 10). LGT is a naturally attenuated virus originally isolated in Malaysia and POW may represent an older lineage of TBE viruses in North America and Asia (Gould et al., 2001, Zanotto et al., 1995). In addition to members of the TBE serocomplex, rDIII from the mosquito-borne WN, YF vaccine strain 17D and YF wild-type strain Asibi were also produced. The amino acid sequence within the DIII of all *flaviviruses* is similar, but the level of identity within the TBE serocomplex is quite high (FIG. 16). This high degree of similarity makes these viruses difficult to distinguish serologically.

Figure 11:
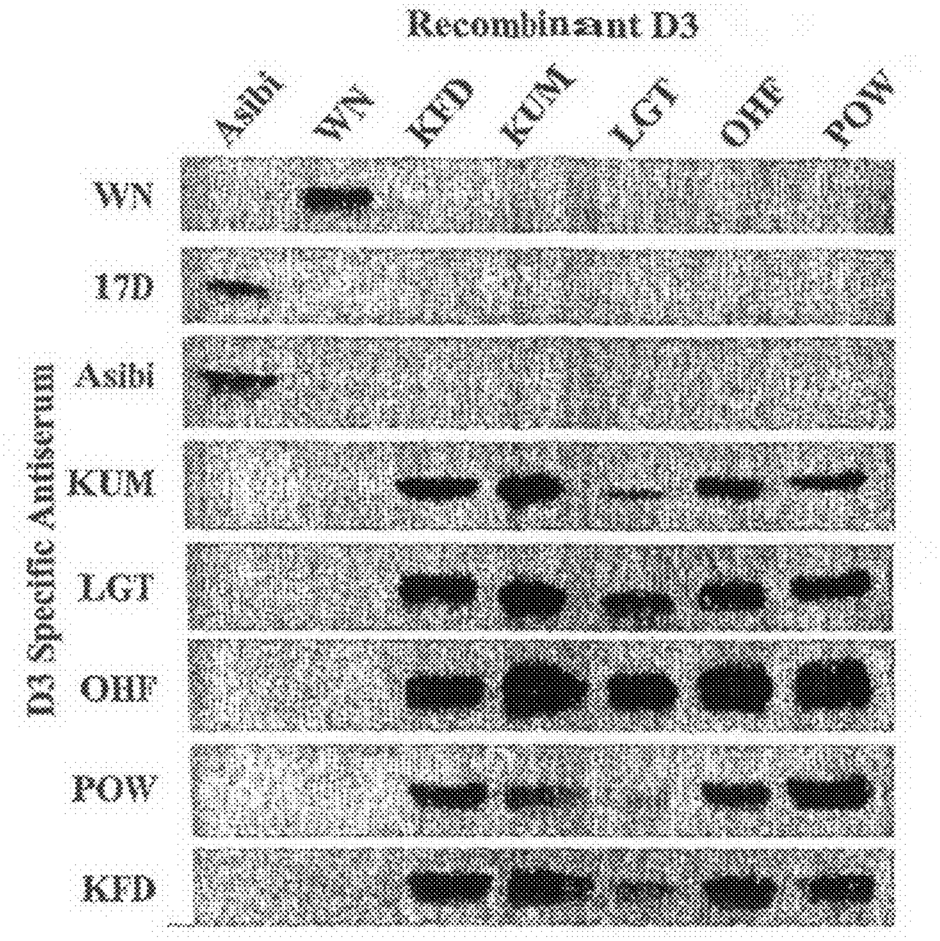
FIG. 11 Western blot of recombinant DIII. Ten ng of purified recombinant DIII was run on 12% SDS-PAGE gels and transferred to nitrocellulose. Blots were probed with homologous or heterologous anti-DIII serum. Asibi, yellow fever type strain; 17D, yellow fever vaccine strain; WN, West Nile virus; KFD, Kyasanur Forrest disease virus; KUM, central European TBE strain Kumlinge; LGT, Langat; OHF, Omsk hemorrhagic disease virus; POW, Powassan virus.

Western Blots:

Purified rDIII derived from several mosquito- and tick-borne *flaviviruses* were run on SDS-PAGE gels and transferred to nitrocellulose for blotting with homologous and heterologous rabbit anti-rDIII specific antiserum. These assays found a significant degree of cross-reactivity between rDIII derived from members of the tick-borne *flavivirus* serocomplex (FIG. 11). All five TBE serocomplex antisera recognized the five TBE serocomplex rDIII, though the sera tended to cross-react less well with LGT rDIII, and the rabbit anti-POW rDIII antiserum appeared to have less cross-reactivity than other sera. This result is not surprising as LGT and POW viruses are phylogenetically less related than KUM, OHF and KFD viruses (FIG. 10). None of the rabbit anti-TBE serocomplex antisera recognized rDIII derived from the mosquito-borne *flaviviruses* WN or YF, nor did rabbit anti-YF or anti-WN antisera recognize any of the TBE rDIII (FIG. 11).

Figures 12A, 12B, 12C, 12D, 12E, 12F:
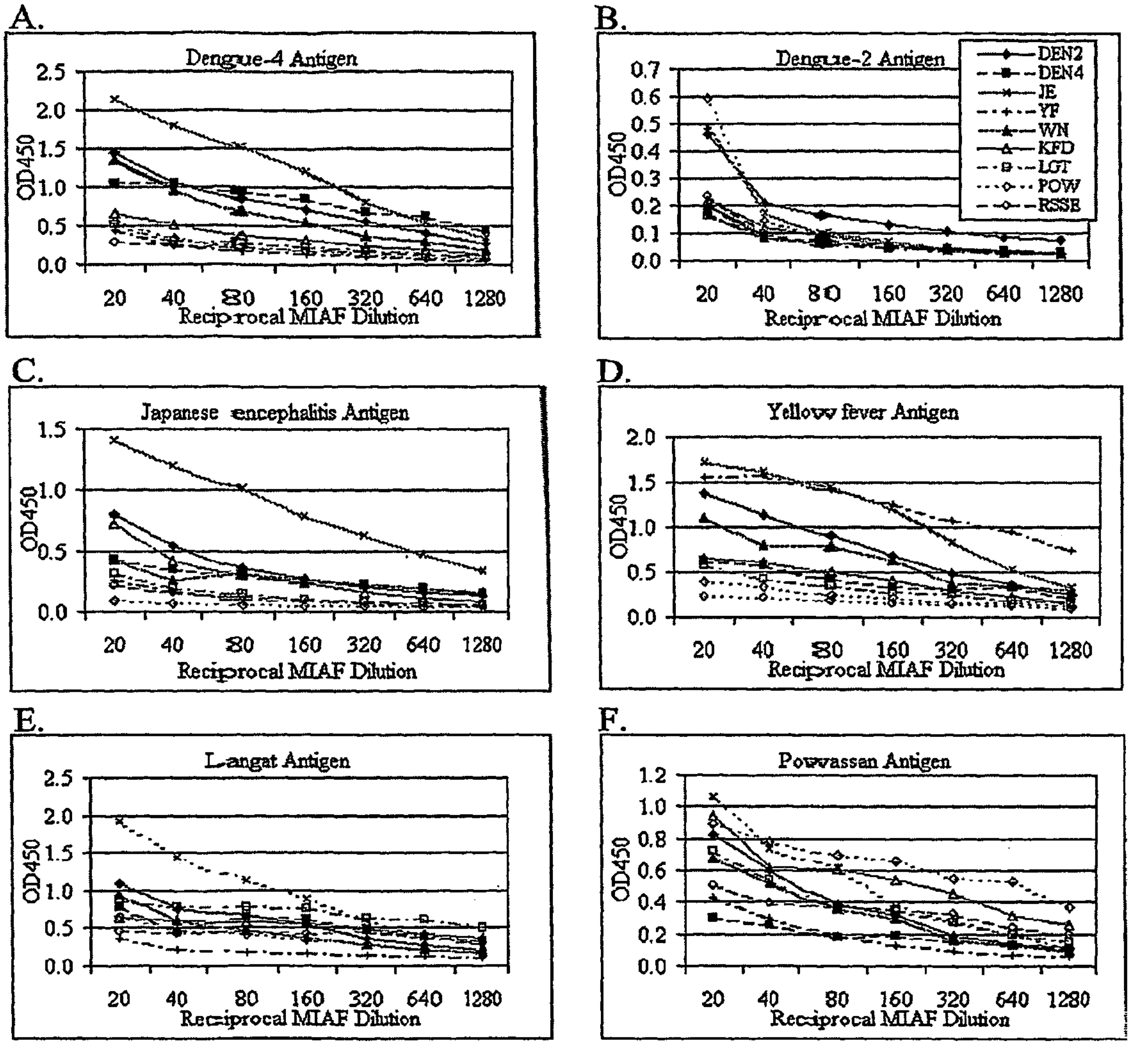
FIG. 12A-12F ELISAs using MIAF to detect virus derived antigen. Mouse brain virus-derived antigen was coated into 96 well plates at 1 HA unit per well and MIAF were tested in two-fold serial dilutions. Each value represents the meant of duplicate wells. The legend in panel B is for all six panels. The tick-borne *flaviviruses* are represented by open symbols.

Viral Antigen Based ELISAs:

Mouse brain-derived viral antigens were coated in 96-well plates at one hemagglutination (HA) unit per well. DIII specific sera and MIAF were diluted at two-fold serial dilutions and sensitivity and specificity of the assay determined. As seen in FIG. 12 there is a lack of specificity for TBE serogroup viral antigens using MIAF. MIAF generated against tick-borne *flaviviruses* are shown in open symbols while the remaining symbols comprise mosquito-borne *flaviviruses*. In all assays JE MIAF cross-reacted strongly with all of the antigens tested. The assay that demonstrated clear specificity was that against JE mouse-derived antigen where the JE MIAF clearly reacted well with the antigen. In the remaining panels, little specificity was found for MIAF binding to mouse-brain derived viral antigen clearly demonstrating that this antigen is not suitable for a diagnostic assay. In these experiments, the MIAF were not normalized against homologous rDIII or virus-derived antigens prior to performing the studies. Instead, the MIAF were tested as received from the World Arbovirus Reference Collection. Due to the lack of availability of sera from natural infections, this method was undertaken to mimic the testing of a potentially infected individual in a true diagnostic setting. In some cases, such as is apparent with JE virus MIAF, the reactive antibody titer may be higher than other MIAF and give a higher level of cross-reactivity. Normalization of the MIAF might reduce the cross-reactivity, but it would also bias the study.

Figures 13A, 13B, 13C, 13D, 13E, 13F:
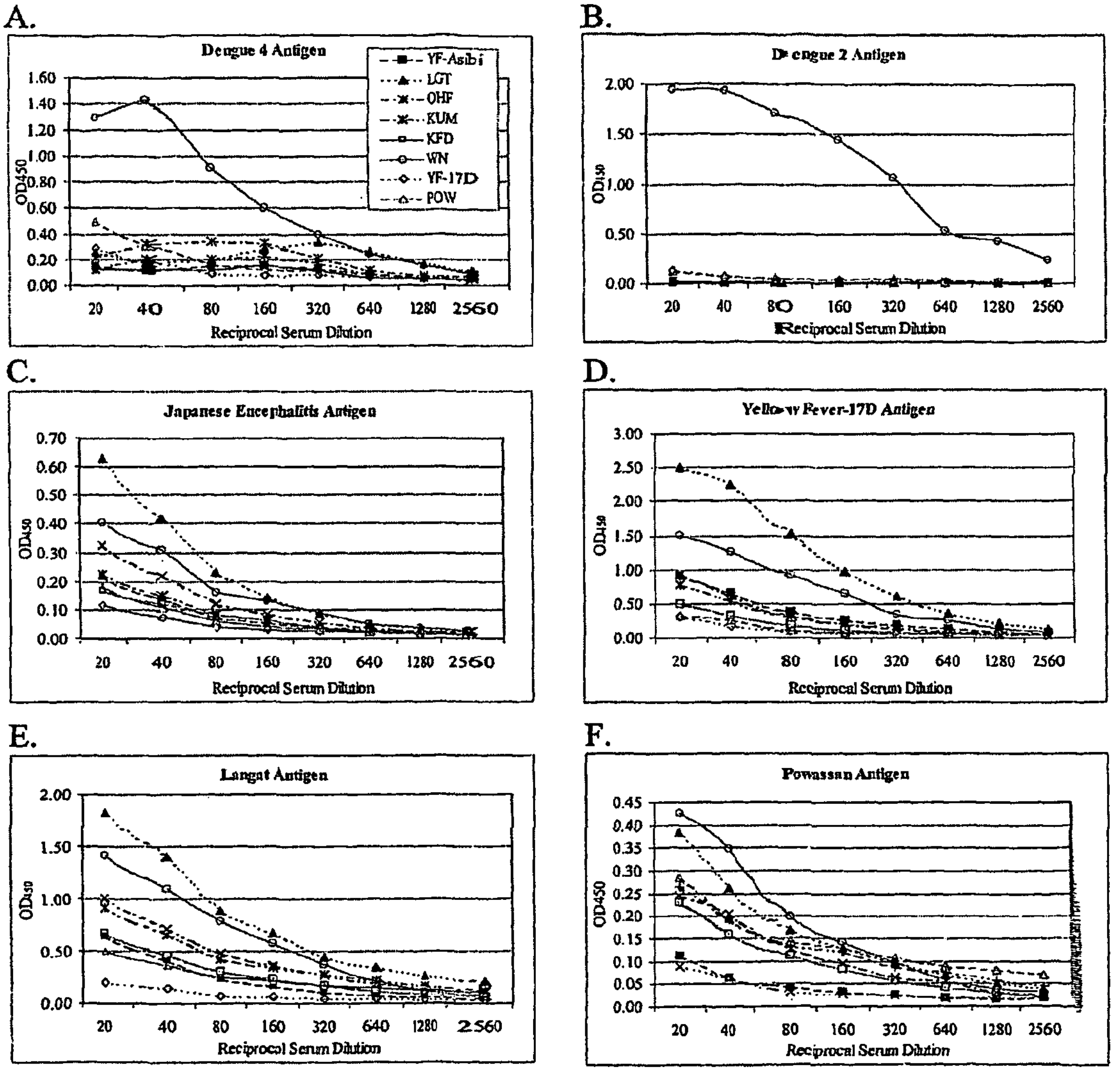
FIG. 13A-13F ELISAs using virus derived antigen to detect IgG in rabbit anti-DIII specific antiserum. Antigens were coated in the plates as 1 HA unit per well and anti-DIII specific sera were tested in two-fold serial dilutions. Each value is the mean of duplicate wells. The legend refers to rabbit anti-DIII specific sera and the legend in panel A is for all panels. Tick-borne *flaviviruses* are represented by open symbols. Note scale differences in the Y-axis.

In similar studies using rabbit anti-rDIII specific antiserum to screen against virus-derived antigen, cross-reactivity was also observed. As seen in FIG. 13, though the degree of cross-reactivity is not as great as was seen in FIG. 12, both rabbit rDIII antiserum specific for the DIII of LGT and WN viruses reacted with several viral antigens. Even though specific antiserum was used in the assay, based on results from western blots (FIG. 11), significant cross reactivity between mosquito-borne virus antigens and antisera specific for tick-borne viruses was found. Again, the antisera were not normalized prior to use in these studies. These results, in conjunction with those shown in FIG. 11, demonstrate that the use of mouse brain-derived viral antigen in a diagnostic assay does not provide the specificity required to conclusively identify to agent responsible during *flavivirus* infection.

The majority of the mouse brain-derived viral antigens tested in these experiments were representative of the mosquito-borne *flaviviruses*. Unfortunately, the assay could not be performed using more TBE serocomplex antigens as some were not available from the World Arbovirus Reference Collection and others that were available in the collection could not be tested due to concerns about the complete inactivation of the virus during antigen preparation (i.e., live virus might be in the antigen preparations) and inadequate facilities for tested potentially infectious antigens (e.g., BSL-4 for OHF and KFD antigens).

Domain III Based ELISAs

Figures 14A, 14B, 14C, 14D, 14E, 14F, 14G, 14H:
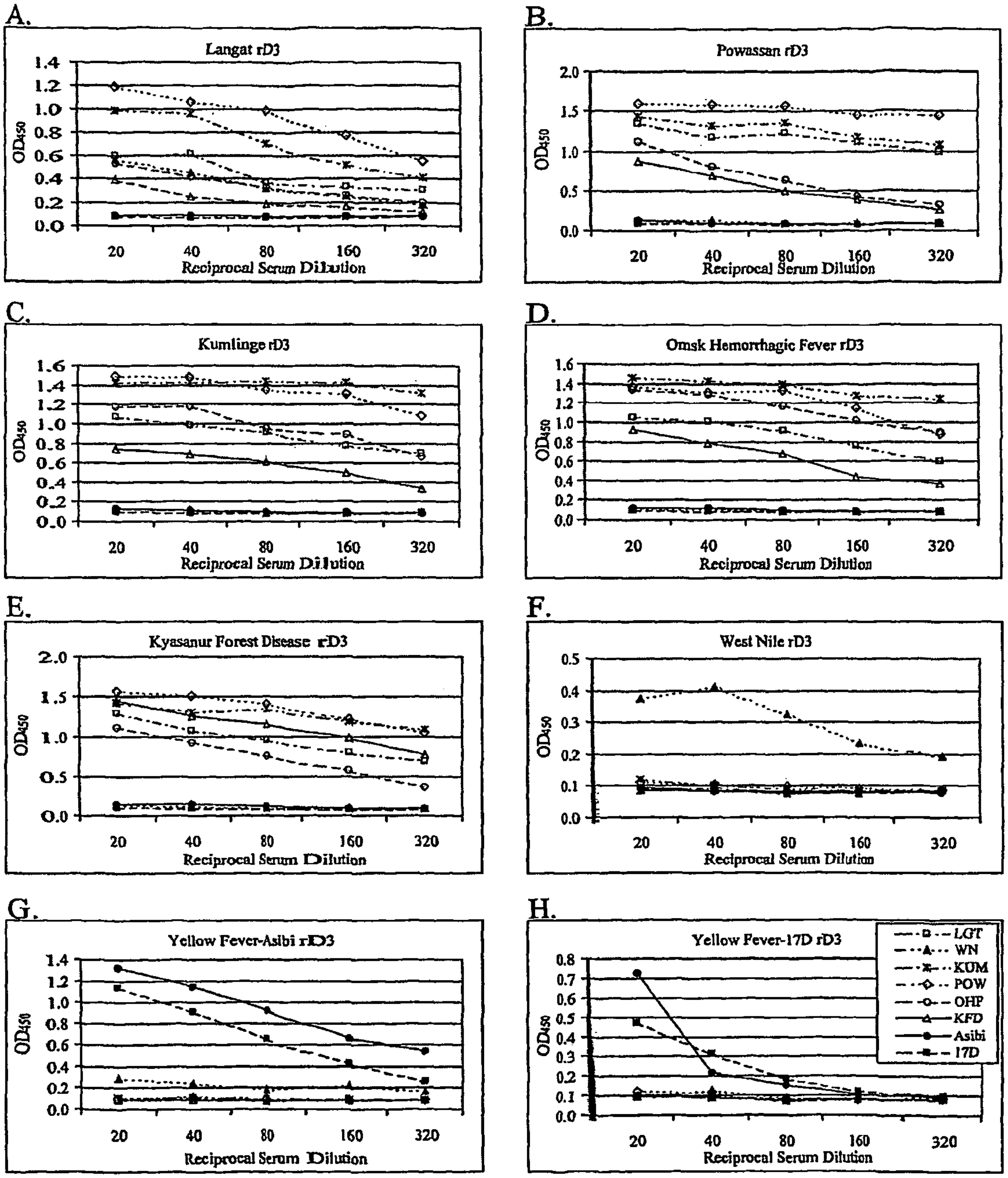
FIG. 14A-14H ELISAs using rDIII to detect IgG in rabbit anti-DIII specific antiserum. Recombinant rDIII was coated into plates at 20 ng per well and DIII specific sera were tested in two-fold serial dilutions. Each value is the mean of duplicate wells. The legend for all panels refers to DIII specific sera and is presented in panel H. Tick-borne *flaviviruses* are represented by open symbols. Note scale differences in Y-axis.

ELISAs using rDIII as the antigen, rather than mouse brain-derived viral antigen, demonstrated a much more specific reaction against homologous rDIII-specific antiserum. Both WN and YF rDIII reacted only with homologous serum (true for both YF wild-type Asibi strain and vaccine 17D strain rDIII) (FIG. 14F-14H). The YF-Asibi rDIII rabbit antiserum cross-reacted with rDIII derived from YF vaccine strain 17D, an expected result as these envelope proteins are nearly identical (FIG. 14G). A similar result was seen in YF-17D rDIII coated plates (FIG. 14H). Recombinant DIII derived from the TBE serocomplex of viruses, however, were not specific for individual virus rDIII specific rabbit antisera, but were cross-reactive with rDIII derived from viruses only within the TBE serocomplex (FIG. 14A-14E, open symbols represent tick-borne *flaviviruses*). This result supports the western blot data presented in FIG. 11 where cross-reactivity was seen between the rabbit antisera generated against the recombinant proteins of the TBE serocomplex. These assays found that TBE sero complex derived rDIII cross-reacted with all of the TBE serocomplex specific rabbit anti-rDIII antisera, but not those derived from the mosquito-borne WN or YF viruses. This assay was also quite sensitive as serum diluted to 1:320 could easily be detected above a 0.2 OD450 cut-off for a positive test. The cross-reactivity among the TBE serocomplex viruses was somewhat expected as the level of amino acid identity among the envelope protein DIII from these viruses is very high (FIG. 16).

Figures 15A, 15B, 15C, 15D, 15E, 15F, 15G, 15H:
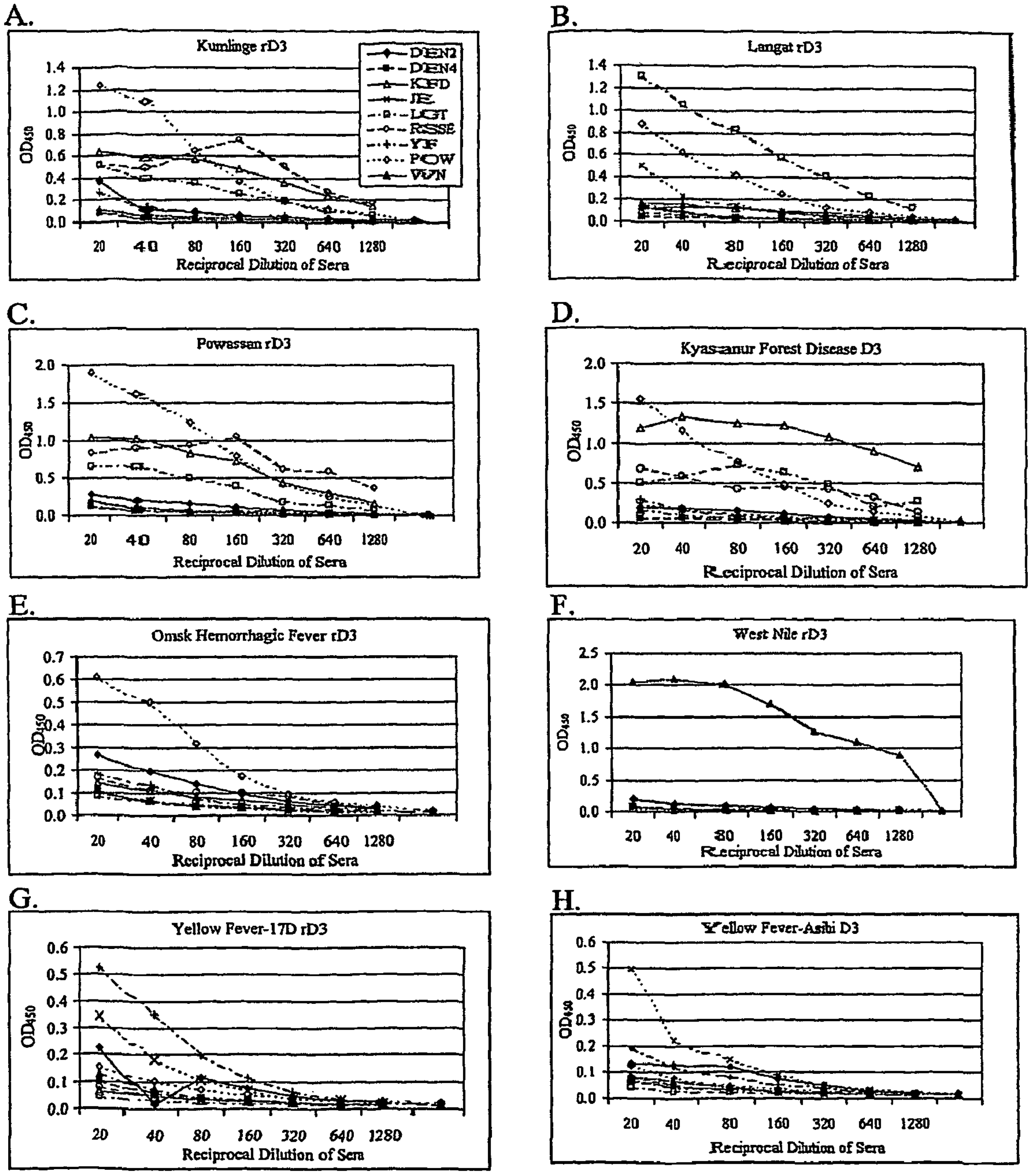
FIG. 15A-15H ELISAs using rDIII to detect virus specific IgG in MIAF Recombinant DIII was coated into plates at 20 ng per well and MIAF were tested in two-fold serial dilutions. Each value represents the mean of duplicate wells. The legend for all panels refers to MIAF and is presented in panel A. Tick-borne *flaviviruses* are represented by open symbols. Note scale differences in the Y-axis.

To examine the ability of rDIII to detect the presence of IgG in a model for analysis of test serum from a potentially infected individual, MIAF were assayed in plates coated with rDIII in experiments similar to those shown above using mouse brain-derived viral antigen. In these experiments, it was found that the rDIII coated plates were able to clearly differentiate MIAF derived from TBE serocomplex infected animals from those of mosquito-borne viruses (FIG. 15). As seen in panels A-E of FIG. 15, TBE serocomplex rDIII cross-reacted with the majority of the TBE serocomplex tested. As with previous figures, TBE serocomplex specific MIAF are shown in open symbols. POW MIAF seemed to cross-react with all of the TBE rDIII whereas the RSSE MIAF was somewhat less reactive. POW MIAF was also the only MIAF to react with OHF rDIII and with considerably less sensitivity than the other rDIII coated plates (FIG. 15E). Unfortunately, OHF specific MIAF was not available from the World Arbovirus Reference Collection. Recombinant DIII for mosquito-borne *flaviviruses* was also highly specific as the WN MIAF reacted only with WN rDIII, as was previously shown (FIG. 15F) and the YF-17D rD3 reacted with YF MIAF (FIG. 15G) though the sensitivity of this assay was not as high as with the TBE serocomplex rDIII or WN rDIII. Both of the YF rDIII cross-reacted with JE MIAF indicating potentially similar surface amino acid residues.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,554,101
U.S. Pat. No. 4,879,236
U.S. Pat. No. 5,587,285
U.S. Pat. No. 5,871,986
U.S. Pat. No. 5,925,565
U.S. Pat. No. 5,935,819
U.S. Pat. No. 6,074,646
Abbondanzo et al., *Breast Cancer Res. Treat.,* 16:182(#151), 1990.
Allred et al., *Breast Cancer Res. Treat.,* 16:182(#149), 1990.
Ausubel et al., In: *Current Protocols in Molecular Biology*, (John Wiley and Sons, Inc., New York, N.Y., 1996.
Beasley and Barrett, *J. Virol.,* 76(24):13097-13100, 2002.
Beasley et al., *Virology,* 296(1):17-23, 2002.
Bhardwaj et al., *J. Virol.* 75:402-407, 2001.
Blackburn et al., *Epidemiol. Infect.,* 99(2):551-557, 1987.
Brown et al. *Breast Cancer Res. Treat.,* 16:1 92(#191), 1990.
Brutlag et al., *CABIOS,* 6:237-245, 1990.
Burke and Monath, In: *Flaviviruses*, Knipe and Howley (Eds.), Fields Virology, $4^{th}$ Ed, Lippincott Williams and Wilkins, P A, 2001
Calisher et al., *J. Gen. Virol.,* 70(Pt 1):37-43, 1989.
Carbonelli et al. *FEMS Microbiol. Lett.,* 177(1):75-82, 1999.
Chou and Fasman, *Adv. Enzymol. Relat. Areas Mol. Biol.,* 47:45-148, 1978a.
Chou and Fasman, *Ann. Rev. Biochem.,* 47:251-276, 1978b.
Chou and Fasman, *Biochemistry,* 13(2):211-222, 1974b.
Chou and Fasman, *Biochemistry,* 13(2):222-245, 1974a.
Chou and Fasman, *Biophys. J.,* 26:367-384, 1979.
Crill and Roehrig, *J. Virol.,* 75(16):7769-7773, 2001.
De Jager et al., *Semin. Nucl. Med.,* 23(2):165-179, 1993.
Dobler et al., *Infection,* 24:405-6, 1996.
Doherty et al., *Trans. R Soc. Trop. Med. Hyg.,* 62(3):430-438, 1968.
Doolittle et al., *Methods Mol. Biol.,* 109:215-37, 1999.
Fetrow and Bryant, *Biotech.,* 11:479-483, 1993.
Fonseca et al., *Am. J. Trop. Med. Hyg.,* 44(5):500-508, 1991.
Gould et al., *Adv. Virus Res.,* 57:71-103, 2001.
Gritsun et al., *Virus Res.,* 27:201-209, 1993.
Gulbis et al., *Hum. Pathol.,* 24:1271-85, 1993.
Hahn et al., *Proc. Natl. Acad. Sci. USA,* 84:2019-2023, 1987.
Hammam et al., *Am. J. Epidemiol.,* 83(1):113-122, 1966.
Harlow and Lane, In: *Antibodies: A Laboratory Manuel*, Cold Spring Harbor Laboratory Press, Cold Spring Harbor, N.Y., 1988.
Heinz et al., In: *Virus Taxonomy,* 859-878, Regenmortel et al., (Eds.), 7th International Committee for the Taxonomy of Viruses, Academic Press, San Diego, 2000.
Inouye et al., *Nucleic Acids Res.,* 13:3101-3109, 1985.
Jameson and Wolf, *Comput. Appl. Biosci.,* 4(1):181-186, 1988.
Jia et al., *Lancet.,* 354(9194):1971-1972, 1999.
Johnson et al., *J. Virol.,* 67:438-445, 1993.
Kyte and Doolittle, *J. Mol. Biol.,* 157(1):105-132, 1982.
Lanctiotti et al., *Science,* 286(5448):2333-2337, 1999.
Levenson et al., *Hum. Gene Ther.,* 9(8):1233-1236, 1998.
Macejak and Samow, *Nature,* 353:90-94, 1991.
Mandl et al., *J. Virol.,* 74(20):9601-9609, 2000.
Martin et al., *Structure,* 10:933-942, 2002.
Morbidity and Mortality Weekly Report, 51(38):862-864, 2002a.
Morbidity and Mortality Weekly Report, 51(36):805-824, 2002b.
Morvan et al., *Ann. Soc. Belg. Med. Trop.,* 70(1):55-63, 1990.
Murgue et al., *Curr. Top Microbiol. Immunol.,* 267:195-221, 2002.
Nakamura et al., In: *Enzyme Immunoassays: Heterogeneous and Homogeneous Systems*, Chapter 27, 1987.
Niedrig et al., *J. Clinical Virology,* 20:1 79-82, 2001.
Pelletier and Sonenberg, *Nature,* 334:320-325; 1988.
Petersen et al., *Emerg. Infect. Dis.,* 7(4):611-614, 2001.
Reneke et al., *Am. J. Clin. Pathol.,* 109(6):754-757, 1998.
Sambrook et al., In: *Molecular cloning*, Cold Spring Harbor Laboratory Press, Cold Spring Harbor, N.Y., 2001.
Sanchez and Ruiz, *J. Gen. Virol.,* 77(Pt 10):2541-2545, 1996.
Scherret et al., *Ann. NY Acad. Sci.,* 951:361-363, 2001.
Wada et al., *Nucleic Acids Res.,* 18:2367-2411, 1990.
Weinberger et al., *Science,* 228:740-742, 1985.
White et al., *Acta Crystallogr. D. Biol. Crystallogr.,* 59:1049-51, 2003.
Wolf et al., *Comput. Appl. Biosci.,* 4(1):187-191, 1988.
Yoshii et al., *J. Virol. Methods,* 108:171-9, 2003.
Zanotto et al., *Virology* 210:152-9, 1995.

The invention claimed is:

1. A method of screening for West Nile Virus in a subject or animal host comprising:

a) contacting a sample from the subject or animal with a composition comprising a flavivirus envelope protein domain III polypeptide under conditions that permit formation of specific immunocomplex between an antibody in the sample and the envelope protein domain III peptide, wherein the envelope protein domain III peptide is a West Nile virus envelope protein domain III peptide and has a length of 103 to 118 amino acids and comprises the amino acid sequence of SEQ ID NO: 11; and b) detecting whether a specific immunocomplex is formed.

2. The method of claim 1, wherein the envelope protein domain III polypeptide is not a fusion protein.

3. The method of claim 1, further comprising at least a second envelope protein domain III polypeptide.

4. The method of claim 1, wherein the immunocomplex is detected using anti-antibody secondary reagents.

5. The method of claim 1, wherein the envelope protein domain III peptide is obtained from a bacteria, a mammalian or an insect cell comprising an expression vector encoding the envelope protein domain III peptide.

6. A composition comprising an isolated West Nile virus envelope protein domain III peptide, wherein the peptide has a length of 103 to 118 amino acids and comprises the amino acid sequence of SEQ ID NO: 11.

7. The composition of claim 6, wherein the envelope protein domain III polypeptide is operatively linked to a substrate.

8. The composition of claim 7, wherein the substrate is a microtiter plate, a bead or a microarray.

9. A kit for screening for West Nile virus antibodies, in a suitable container, comprising at least one envelope protein domain III polypeptide, wherein the at least one envelope protein domain III polypeptide is a West Nile virus envelope protein domain III peptide, wherein the peptide has a length of 103 to 118 amino acids and comprises the amino acid sequence of SEQ ID NO: 11.

10. A kit for screening for West Nile virus antibodies in a subject comprising:

a) an assay plate comprising a multiplicity of microtiter wells comprising a composition comprising an envelope protein domain III polypeptide capable of binding a West Nile virus antibody in the sample that can specifically bind to the envelope protein domain III polypeptide wherein at least one domain III polypeptide is a West Nile virus envelope protein domain III peptide, wherein the peptide has a length of 103 to 118 amino acids and comprises the amino acid sequence of SEQ ID NO: 11; and b) a container comprising a labeled secondary antibody having specific binding affinity for a West Nile virus antibody in the sample that can specifically bind to the envelope protein domain III polypeptide.

11. A method of screening for West Nile virus in a subject comprising:

a) contacting a sample from the subject with a composition from the kit of claim 9; and, b) detecting whether an immunocomplex is formed between an antibody and the envelope protein domain III polypeptide.

12. The composition of claim 7, further comprising an envelope domain III peptide comprising at most 100 contiguous amino acid sequence of SEQ ID NO:4, an envelope domain III peptide comprising at most 100 contiguous amino acid sequence of SEQ ID NO:4, an envelope domain III peptide comprising at most 100 contiguous amino acid sequence of SEQ ID NO:5, an envelope domain III peptide comprising at most 100 contiguous amino acid sequence of SEQ ID NO:6, an envelope domain III peptide comprising at most 99 contiguous amino acid sequence of SEQ ID NO:7, an envelope domain III peptide comprising at most 103 contiguous amino acid sequence of SEQ ID NO:8, an envelope domain III peptide comprising at most 103 contiguous amino acid sequence of SEQ ID NO:9, an envelope domain III peptide comprising at most 103 contiguous amino acid sequence of SEQ ID NO:10, an envelope domain III peptide comprising at most 103 contiguous amino acid sequence of SEQ ID NO:12, an envelope domain III peptide comprising at most 100 contiguous amino acid sequence of SEQ ID NO:13, an envelope domain III peptide comprising at most 96 contiguous amino acid sequence of SEQ ID NO:14, an envelope domain III peptide comprising at most 96 contiguous amino acid sequence of SEQ ID NO:15, an envelope domain III peptide comprising at most 96 contiguous amino acid sequence of SEQ ID NO:16, an envelope domain III peptide comprising at most 96 contiguous amino acid sequence of SEQ ID NO:17, an envelope domain III peptide comprising at most 96 contiguous amino acid sequence of SEQ ID NO:18, an envelope domain III peptide comprising at most 96 contiguous amino acid sequence of SEQ ID NO:19, an envelope domain III peptide comprising at most 97 contiguous amino acid sequence of SEQ ID NO:20, and/or an envelope domain III peptide comprising at most 111 contiguous amino acid sequence of SEQ ID NO:21.

13. The kit of claim 9, further comprising an envelope domain III peptide comprising at most 100 contiguous amino acid sequence of SEQ ID NO:4, an envelope domain III peptide comprising at most 100 contiguous amino acid sequence of SEQ ID NO:4, an envelope domain III peptide comprising at most 100 contiguous amino acid sequence of SEQ ID NO:5, an envelope domain III peptide comprising at most 100 contiguous amino acid sequence of SEQ ID NO:6, an envelope domain III peptide comprising at most 99 contiguous amino acid sequence of SEQ ID NO:7, an envelope domain III peptide comprising at most 103 contiguous amino acid sequence of SEQ ID NO:8, an envelope domain III peptide comprising at most 103 contiguous amino acid sequence of SEQ ID NO:9, an envelope domain III peptide comprising at most 103 contiguous amino acid sequence of SEQ ID NO:10, an envelope domain III peptide comprising at most 103 contiguous amino acid sequence of SEQ ID NO:12, an envelope domain III peptide comprising at most 100 contiguous amino acid sequence of SEQ ID NO:13, an envelope domain III peptide comprising at most 96 contiguous amino acid sequence of SEQ ID NO:14, an envelope domain III peptide comprising at most 96 contiguous amino acid sequence of SEQ ID NO:15, an envelope domain III peptide comprising at most 96 contiguous amino acid sequence of SEQ ID NO:16, an envelope domain III peptide comprising at most 96 contiguous amino acid sequence of SEQ ID NO:17, an envelope domain III peptide comprising at most 96 contiguous amino acid sequence of SEQ ID NO:18, an envelope domain III peptide comprising at most 96 contiguous amino acid sequence of SEQ ID NO:19, an envelope domain III peptide comprising at most 97 contiguous amino acid sequence of SEQ ID NO:20, and/or an envelope domain III peptide comprising at most 111 contiguous amino acid sequence of SEQ ID NO:21.

* * * * *

UNITED STATES PATENT AND TRADEMARK OFFICE

CERTIFICATE OF CORRECTION

PATENT NO. : 7,785,799 B2
APPLICATION NO. : 10/524939
DATED : August 31, 2010
INVENTOR(S) : Alan Barrett et al.

It is certified that error appears in the above-identified patent and that said Letters Patent is hereby corrected as shown below:

In column 1, lines 11-14, delete paragraph and insert
--This invention was made with government support under contract number U90/CCU618754-01 awarded by the United States Department of Health and Human Services Centers for Disease Control. The government has certain rights in the invention.-- therefor.

Signed and Sealed this

Sixteenth Day of November, 2010

David J. Kappos
*Director of the United States Patent and Trademark Office*